US012340907B2

(12) United States Patent
Zhou et al.

(10) Patent No.: US 12,340,907 B2
(45) Date of Patent: Jun. 24, 2025

(54) SYSTEMS, METHODS, AND APPARATUSES FOR IMPLEMENTING ADVANCEMENTS TOWARDS ANNOTATION EFFICIENT DEEP LEARNING IN COMPUTER-AIDED DIAGNOSIS

(71) Applicant: Arizona Board of Regents on behalf of Arizona State University, Scottsdale, AZ (US)

(72) Inventors: Zongwei Zhou, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 710 days.

(21) Appl. No.: 17/716,929

(22) Filed: Apr. 8, 2022

(65) Prior Publication Data
US 2022/0328189 A1 Oct. 13, 2022

Related U.S. Application Data

(60) Provisional application No. 63/173,250, filed on Apr. 9, 2021, provisional application No. 63/188,981, filed on May 14, 2021.

(51) Int. Cl.
*G06F 18/21* (2023.01)
*G06V 10/26* (2022.01)
(Continued)

(52) U.S. Cl.
CPC ......... *G16H 50/20* (2018.01); *G06V 10/7753* (2022.01)

(58) Field of Classification Search
None
See application file for complete search history.

(56) References Cited

U.S. PATENT DOCUMENTS

| 9,760,990 B2 | 9/2017 | Abedini et al. |
| 10,210,609 B2 | 2/2019 | DeVries |

(Continued)

FOREIGN PATENT DOCUMENTS

| CN | 111210024 A | * | 5/2020 | ............. G06N 20/00 |
| WO | WO-2020247810 A1 | * | 12/2020 | ......... G06F 18/2148 |
| WO | WO-2022171996 A1 | * | 8/2022 | ......... G06F 16/3344 |

OTHER PUBLICATIONS

Doersch, C. et al., "Multi-task Self-Supervised Visual Learning," Proceedings of the IEEE International Conference on Computer Vision, 2017, pp. 2070-2079.
(Continued)

*Primary Examiner* — Mohammed Rachedine
(74) *Attorney, Agent, or Firm* — Elliott, Ostrander & Preston, P.C.

(57) ABSTRACT

Embodiments described herein include systems for implementing annotation-efficient deep learning in computer-aided diagnosis. Exemplary embodiments include systems having a processor and a memory specially configured with instructions for learning annotation-efficient deep learning from non-labeled medical images to generate a trained deep-learning model by applying a multi-phase model training process via specially configured instructions for pre-training a model by executing a one-time learning procedure using an initial annotated image dataset; iteratively re-training the model by executing a fine-tuning learning procedure using newly available annotated images without re-using any images from the initial annotated image dataset; selecting a plurality of most representative samples related to images of the initial annotated image dataset and the newly available annotated images by executing an active selection procedure based on the which of a collection of un-annotated images exhibit either a greatest uncertainty or a greatest entropy; extracting generic image features; updat- (Continued)

ing the model using the generic image features extracted; and outputting the model as the trained deep-learning model for use in analyzing a patient medical image. Other related embodiments are disclosed.

20 Claims, 32 Drawing Sheets

(51) Int. Cl.
*G06V 10/44* (2022.01)
*G06V 10/774* (2022.01)
*G06V 10/82* (2022.01)
*G16H 30/40* (2018.01)
*G16H 40/67* (2018.01)
*G16H 50/20* (2018.01)
*G16H 50/70* (2018.01)

(56) References Cited

U.S. PATENT DOCUMENTS

| | | | |
|---|---|---|---|
| 2018/0060487 | A1 | 3/2018 | Barkan et al. |
| 2020/0387755 | A1* | 12/2020 | Hagen ............... G06F 18/2155 |
| 2021/0265043 | A1* | 8/2021 | Haghighi ............... G16H 50/20 |
| 2022/0037018 | A1* | 2/2022 | Goede ............... G06F 18/251 |
| 2022/0044070 | A1* | 2/2022 | Koh ............... G06N 3/08 |
| 2023/0116897 | A1 | 4/2023 | Hosseinzadeh Taher et al. |
| 2023/0326598 | A1* | 10/2023 | Sommer ............... G16H 30/40 705/2 |
| 2024/0362775 | A1 | 10/2024 | Liang |

OTHER PUBLICATIONS

Doersch, C. et al., "Unsupervised Visual Representation Learning by Context Prediction," Proceedings of the IEEE International Conference on Computer Vision, 2015, pp. 1422-1430.

Dosovitskiy, A. et al., "An Image is Worth 16×16 Words: Transformers for Image Recognition at Scale," arXiv preprint arXiv:2010.11929v1 [cs.CV] Oct. 22, 2020, 21 pages.

Dosovitskiy, A. et al., "Discriminative Unsupervised Feature Learning with Convolutional Neural Networks," IEEE Transactions on Pattern Analysis and Machine Intelligence, vol. 38, No. 9, 2016, pp. 1734-1747.

Dou, Q. et al., "3D deeply supervised network for automated segmentation of volumetric medical images," Medical Image Analysis, vol. 41, 2017, pp. 40-54.

Dou, Q. et al., "3D Deeply Supervised Network for Automatic Liver Segmentation from CT Volumes," in International Conference on Medical Image Computing and Computer-Assisted Intervention, 2016, Springer, Cham, pp. 149-157.

Drozdzal, M. et al., "The Importance of Skip Connections in Biomedical Image Segmentation," in Deep Learning and Data Labeling for Medical Applications. 2016, Springer, Cham, pp. 179-187.

Esteva, A. et al., "A guide to deep learning in healthcare," Nature Medicine, vol. 25, No. 1, 2019, pp. 24-29.

Esteva, A. et al., "Dermatologist-level classification of skin cancer with deep neural networks," Nature, vol. 542, 2017, pp. 115-118.

Fairfield, J., "Toboggan Contrast Enhancement for Contrast Segmentation," Proceedings., 10th International Conference on Pattern Recognition, IEEE, 1990, pp. 712-716.

Falk, T. et al, "U-Net: deep learning for cell counting, detection, and morphometry," Nature Methods, vol. 16, 2018, pp. 67-70.

Feng, R. et al., "Parts2whole: Self-supervised Contrastive Learning via Reconstruction," Domain Adaptation and Representation Transfer, and Distributed and Collaborative Learning: Second MICCAI Workshop, DART 2020, Springer International Publishing, pp. 85-95.

Fotedar, G. et al., "Extreme Consistency: Overcoming Annotation Scarcity and Domain Shifts," Medical Image Computing and Computer Assisted Intervention—MICCAI 2020: 23rd International Conference, Lima, Peru, Oct. 4- 8, 2020, Proceedings, Part I 23, 2020, Springer International Publishing, pp. 699-709.

Fourure, D. et al, "Residual Conv-Deconv Grid Network for Semantic Segmentation," in Proceedings of the British Machine Vision Conference, 2017, 12 pages.

Gal, Y. et al., "Deep Bayesian Active Learning with Image Data," International Conference on Machine Learning, PMLR, 2017, pp. 1183-1192.

Gal, Y. et al., "Dropout as a Bayesian Approximation: Representing Model Uncertainty in Deep Learning," International Conference on Machine Learning, PMLR, 2016, pp. 1050-1059.

Gan, Z., R., et al. "Learning Deep Sigmoid Belief Networks with Data Augmentation", in "Artificial Intelligence and Statistics", (2015), pp. 268-276.

Gepner, A. et al., "Comparison of Coronary Artery Calcium Presence, Carotid Plaque Presence, and Carotid Intima-Media Thickness for Cardiovascular Disease Prediction in the Multi-Ethnic Study of Atherosclerosis", Circulation: Cardiovascular Imaging vol. 8, No. 1, Jan. 2015, pp. 1-8.

Gibson, E. et al., "Automatic Multi-Organ Segmentation on Abdominal CT with Dense V-Networks," IEEE Transactions on Medical Imaging, vol. 37, No. 8, Aug. 2018, pp. 1822-1834.

Gibson, E. et al., "NiftyNet: a deep-learning platform for medical imaging," Computer Methods and Programs in Biomedicine, vol. 158, 2018, pp. 113-122.

Glorot, X. et al., "Understanding the difficulty of training deep feedforward neural networks," Proceedings of the Thirteenth International Conference on Artificial Intelligence and Statistics, Journal of Machine Learning Research, 2010, pp. 249-256.

González, G., et al, "Computer Aided Detection for Pulmonary Embolism Challenge (CAD-PE)," arXiv preprint arXiv:2003.13440, 2020, 8 pages.

Goyal, P. et al., "Scaling and Benchmarking Self-Supervised Visual Representation Learnin.g," Proceedings of the IEEE/CVF International Conference on Computer Vision, 2019, pp. 6390-6399.

Graham, B., "Fractional Max-Pooling," arXiv:1412.6071v1 [cs.CV], 2014, 10 pages.

Greenspan, H. et al., "Guest Editorial Deep Learning in Medical Imaging: Overview and Future Promise of an Exciting New Technique", IEEE Transactions on Medical Imaging, vol. 35, No. 5, May 2016, pp. 1153-1159.

Grill, J.B. et al., "Bootstrap Your Own Latent: A New Approach to Self-Supervised Learning," arXiv preprint arXiv:2006.07733v1 [cs.CV] (2020), 28 pages.

Guan, Q., et al, "Multi-label chest X-ray image classification via category-wise residual attention learning," Pattern Recognition Letters, 130, 2020, pp. 259-266.

Guendel, S., et al, "Learning to Recognize Abnormalities in Chest X-Rays with Location-Aware Dense Networks," in Iberoamerican Congress on Pattern Recognition (Springer 2018), pp. 757-765.

Gulshan, V., et al., "Development and Validation of a Deep Learning Algorithm for Detection of Diabetic Retinopathy in Retinal Fundus Photographs", JAMA, vol. 316, No. 22, 2016, pp. 2402-2410.

Guyon, I. et al., "Results of the Active Learning Challenge", Active Learning and Experimental Design workshop In conjunction with AISTATS 2010, JMLR: Workshop and Conference Proceedings, 2011, vol. 16, pp. 19-45.

Haenssle, H. A., et al., "Man against machine: diagnostic performance of a deep learning convolutional neural network for dermoscopic melanoma recognition in comparison to 58 dermatologists", Annals of Oncology, 29, 8, (2018), pp. 1836-1842.

Haghighi, F. et al., "Learning Semantics-Enriched Representation via Self-discovery, Self-classification, and Self-restoration," Medical Image Computing and Computer Assisted Intervention—MICCAI 2020, Lecture Notes in Computer Science, vol. 12261, Springer International Publishing Cham (2020), pp. 137-147.

Hara, K., et al., "Can Spatiotemporal 3D CNNs Retrace the History of 2D CNNs and ImageNet?", in "Proceedings of the IEEE Conference on ComputerVision and Pattern Recognition", (2018), pp. 6546-6555.

(56) References Cited

OTHER PUBLICATIONS

Hariharan, B. et al., "Hypercolumns for Object Segmentation and Fine-grained Localization," in Proceedings of the IEEE Conference on Computer Vision and Pattern Recognition, 2015, pp. 447-456.

He, H. et al., "Learning from Imbalanced Data", IEEE Transactions on Knowledge and Data Engineering, Sep. 2009 (date of publication Jun. 2009), vol. 21, No. 9, pp. 1263-1284.

He, K. et al, "Identity Mappings in Deep Residual Networks," in Proceedings of the European Conference on Computer Vision, 2016, pp. 630-645, Springer, Cham.

He, K. et al, "Mask R-CNN," in Proceedings of the IEEE International Conference on Computer Vision, 2017, pp. 2980-2988.

He, K. et al., "Deep Residual Learning for Image Recognition", Proceedings of the IEEE Conference on Computer Vision and Pattern Recognition (CVPR), Jun. 2016, pp. 770-778.

He, K. et al., "Delving Deep into Rectifiers: Surpassing Human-Level Performance on ImageNet Classification," Proceedings of the IEEE Conference on Computer Vision and Pattern Recognition, 2015, pp. 1026-1034.

He, K. et al., "Momentum Contrast for Unsupervised Visual Representation Learning," Proceedings of the IEEE/CVF Conference on Computer Vision and Pattern Recognition, 2020, pp. 9726-9735.

Hendrycks, D. et al., "Using Self-Supervised Learning Can Improve Model Robustness and Uncertainty," Advances in Neural Information Processing Systems, 32, 2019,12 pages.

Hino, H., "Active learning: Problem Settings and Recent Developments," arXiv preprint arXiv:2012.04225v2 [cs.LG], 2020, 31 pages.

Hinton, G. et al, "Distilling the Knowledge in a Neural Network." arXiv preprint arXiv:1503.02531v1 [stat.ML], 2015, 9 pages.

Hinton, G., "How to represent part-whole hierarchies in a neural network," arXiv preprint arXiv:2102.12627v1 [cs.CV], 2021, 44 pages.

Holub, A. et al., "Entropy-Based Active Learning for object Recognition," 2008 IEEE Computer Society Conference on Computer Vision and Pattern Recognition Workshops, 2008, 8 pages.

Hoo-Chang, S. et al, "Deep Convolutional Neural Networks for Computer-Aided Detection: CNN Architectures, Dataset Characteristics and Transfer Learning," IEEE Transactions on Medical Imaging, vol. 35, No. 5, 2016, pp. 1285-1298.

Horlander, K. T., et al., "Pulmonary Embolism Mortality in the United States, 1979-1998: An Analysis Using Multiple-Cause Mortality Data", Archives of Internal Medicine vol. 163, No. 14, (2003), pp. 1711-1717.

Hu, R. et al, "Learning to Segment Every Thing," in Proceedings of the IEEE Conference on Computer Vision and Pattern Recognition, 2018, pp. 4233-4241.

Huang, G. et al, "Densely Connected Convolutional Networks," in Proceedings of the IEEE Conference on Computer Vision and Pattern Recognition, 2017, pp. 2261-2269.

Huang, S.C. et al., "PENet—a scalable deep-learning model for automated diagnosis of pulmonary embolism using volumetric CT imaging." NPJ Digital Medicine vol. 3, No. 1, Article No. 61, 2020, 9 pages.

Standley, T., et al., "Which Tasks Should be Learned Together in Multi-task Learning," 37th International Conference on Machine Learning (PMLR), vol. 119, 2020, pp. 9120-9132.

Stein, J. et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force Endorsed by the Society for Vascular Medicine", Journal of the American Society of Echocardiography, 2008, vol. 21, No. 2, pp. 93-111.

Sudre, C. H. et al, "Generalised Dice Overlap as a Deep Learning Loss Function for Highly Unbalanced Segmentations," in Deep Learning in Medical Image Analysis and Multimodal Learning for Clinical Decision Support, 2017, Springer, Cham, pp. 240-248.

Sun, C. et al., "Revisiting Unreasonable Effectiveness of Data in Deep Learning Era," Proceedings of the IEEE International Conference on Computer Vision (ICCV), 2017, pp. 843-852.

Sun, C., et al, "Automatic segmentation of liver tumors from multiphase contrast-enhanced CT images based on FCNS," Artificial Intelligence in Medicine, vol. 83, Nov. 2017, pp. 58-66.

Sun, W. et al., "Automatic feature learning using multichannel ROI based on deep structured algorithms for computerized lung cancer diagnosis," Computers in Biology and Medicine, vol. 89, 2017, pp. 530-539.

Szegedy, C. et al., "Going Deeper with Convolutions," Proceedings of the IEEE Conference on Computer Vision and Pattern Recognition, 2015, pp. 1-9.

Tajbakhsh, et al., "Convolutional Neural Networks for Medical Image Analysis: Full Training or Fine Tuning?", IEEE Transactions on Medical Imaging, vol. 35, No. 5, May 2016, pp. 1299-1312.

Tajbakhsh, N. et al, "ErrorNet: Learning Error Representations from Limited Data to Improve Vascular Segmentation," IEEE 17th International Symposium on Biomedical Imaging (2020), pp. 1364-1368.

Tajbakhsh, N. et al., "Computer-aided detection and visualization of pulmonary embolism using a novel, compact, and discriminative image representation," Medical Image Analysis, vol. 58, 2019, article 101541, 13 pages.

Tajbakhsh, N. et al., "Computer-Aided Pulmonary Embolism Detection Using a Novel Vessel-Aligned Multi-planar Image Representation and Convolutional Neural Networks," International Conference on Medical Image Computing and Computer-Assisted Intervention, 2015, Springer, Cham, pp. 62-69.

Tajbakhsh, N. et al., "Embracing imperfect datasets: A review of deep learning solutions for medical image segmentation," Medical Image Analysis, vol. 63, 2020, article 101693, 30 pages.

Tajbakhsh, N. et al., "Surrogate Supervision for Medical Image Analysis: Effective Deep Learning from Limited Quantities of Labeled Data," 2019 IEEE 16th International Symposium on Biomedical Imaging (ISBI 2019), pp. 1251-1255.

Taleb, A. et al., "3D Self-Supervised Methods for Medical Imaging," arXiv preprint arXiv:2006.03829v1, 2020, 17 pages.

Tang, H., et al, "NoduleNet: Decoupled False Positive Reduction for Pulmonary Nodule Detection and Segmentation," International Conference on Medical Image Computing and Computer Assisted Intervention—MICCAI 2019, Lecture Notes on Computer Science Vo. 11769, 2019, Springer International Publishing, pp. 266-274.

Tang, Y. et al., "Attention-Guided Curriculum Learning for Weakly Supervised Classification and Localization of Thoracic Diseases on Chest Radiographs," International Workshop on Machine Learning in Medical Imaging, 2018, Springer, Cham., pp. 249-258.

Touvron, H. et al., "Fixing the train-test resolution discrepancy," arXiv:1906.06423v3 [cs.CV], 2020, 14 pages.

Tsymbalov, E. et al., "Dropout-Based Active Learning for Regression," Analysis of Images, Social Networks and Texts: 7th International Conference, AIST 2018, Springer International Publishing, pp. 247-258.

Venturini, L. et al., "Uncertainty Estimates as Data Selection Criteria to Boost Omni-Supervised Learning," Medical Image Computing and Computer Assisted Intervention—MICCAI 2020, Springer International Publishing, pp. 689-698.

Vincent, P., et al, "Stacked Denoising Autoencoders: Learning Ueful Representations in a Deep Network with a Local Denoising Criterion," Journal of Machine Learning Research, vol. 11, No. 12, 2010, pp. 3371-3408.

Voulodimos, A., et al, "Deep Learning for Computer Vision: A Brief Review," Computational Intelligence and Neuroscience, vol. 2018, Article 7068349, 13 pages.

Wang, H. et al., "Comparison of machine learning methods for classifying mediastinal lymph node metastasis of non-small cell lung cancer from 18 F-FDG PET/CT images," EJNMMI Research, vol. 7, 2017, pp. 1-11.

Wang, W. et al., "Deep Active Self-paced Learning for Accurate Pulmonary Nodule Segmentation," International Conference on Medical Image Computing and Computer Assisted Intervention—MICCAI 2018, Springer International Publishing, pp. 723-731.

Wang, X. et al., "ChestX-ray8: Hospital-scale Chest X-ray Database and Benchmarks on Weakly-Supervised Classification and Local-

(56) References Cited

OTHER PUBLICATIONS ization of Common Thorax Diseases," Proceedings of the IEEE Conference on Computer Vision and Pattern Recognition, 2017, pp. 3462-3471.

Wang, Z., et al., "Image Quality Assessment: From Error Visibility to Structural Similarity," IEEE Transactions on Image Processing, vol. 13, No. 4 (Apr. 2004), pp. 600-612.

Weikert, T., et al., "Automated detection of pulmonary embolism in CT pulmonary angiograms using an AI-powered algorithm", European Radiology 30, 12, (2020), pp. 6545-6553.

Weiss, K., et al, "A survey of transfer learning," Journal of Big Data, vol. 3, Article No. 9, 2016, 40 pages.

Wittenberg, R., et al., "Computed Tomography Pulmonary Angiography in Acute Pulmonary Embolism the Effect of a Computer-assisted Detection Prototype Used as a Concurrent Reader", Journal of Thoracic Imaging 28, 5, (2013), pp. 315-321.

Wittenberg, R., et al., "Impact of Image Quality on the Performance of Computer-Aided Detection of Pulmonary Embolism", American Journal of Roentgenology, vol. 196, No. 1, (2011), pp. 95-101.

Wong, S.C., et al., "Understanding data augmentation for classification: when to warp?", in 2016 International Conference on Digital Image Computing: Techniques and Applications (DICTA), 2016, pp. 1-6.

Wu, S., et al. "On the Generalization Effects of Linear Transformations in Data Augmentation", arXiv preprint arXiv:2005.00695v1 [cs.LG], (2020), 20 pages.

Xie, S. et al, "Holistically-Nested Edge Detection," in Proceedings of the IEEE International Conference on Computer Vision, 2015, pp. 1395-1403.

Yamamoto, Y. et al., "Automated acquisition of explainable knowledge from unannotated histopathology images," Nature communications, vol. 10, Article 5642, 2019, 9 pages.

Yang, L. et al., "Suggestive Annotation: A Deep Active Learning Framework for Biomedical Image Segmentation," International Conference on Medical Image Computing and Computer-Assisted Intervention(Springer, 2017), pp. 399-407.

Yosinski, J. et al., "How transferable are features in deep neural networks?," Advances in Neural Information Processing Systems, 27, 2014, pp. 3320-3328.

Yu, F. et al, "Deep Layer Aggregation," in Proceedings of the IEEE Conference on Computer Vision and Pattern Recognition, 2018, pp. 2403-2412.

Yu, L. et al., "Uncertainty-Aware Self-ensembling Model for Semi-supervised 3D Left Atrium Segmentation," Medical Image Computing and Computer Assisted Intervention—MICCAI 2019, Springer International Publishing, pp. 605-613.

Yuan, M. et al., "Cold-start Active Learning through Self-supervised Language Modeling," arXiv preprint arXiv:2010.09535v2 [cs.CL], 2020, 14 pages.

Yuan, X.T. et al., "Truncated Power Method for Sparse Eigenvalue Problems," Journal of Machine Learning Research, 14.4, 2013, pp. 899-925.

Zhang, L. et al., "AET vs. AED: Unsupervised Representation Learning by Auto-Encoding Transformations Rather than Data," Proceedings of the IEEE/CVF Conference on Computer Vision and Pattern Recognition, 2019, pp. 2542-2550.

Zhang, R., et al, "Colorful Image Colorization," Proceedings of the European Conference on Computer Vision, 2016, Springer International Publishing, pp. 649-666.

Zhang, R., et al, "Split-Brain Autoencoders: Unsupervised Learning by Cross-Channel Prediction," Proceedings of the IEEE Conference on Computer Vision and Pattern Recognition, 2017, pp. 645-654.

Zhang, T., et al, "Solving Large Scale Linear Prediction Problems Using Stochastic Gradient Descent Algorithms," Proceedings of the 21st International Conference on Machine Learning, 2004, 8 pages.

Zhang, Y et al, "A Survey on Multi-Task Learning," arXiv:1707.08114v1 [cs.LG], 2017, 20 pages.

Zhang, Y. et al, "Customizable Architecture Search for Semantic Segmentation," in Proceedings of the IEEE Conference on Computer Vision and Pattern Recognition, 2019, pp. 11633-11642.

Zhao, H. et al, "ICNet for Real-Time Semantic Segmentation on High-Resolution Images," in Proceedings of the European Conference on Computer Vision, 2018, pp. 418-434.

Zhou, B. et al, "Learning Deep Features for Discriminative Localization," in Proceedings of the IEEE Conference on Computer Vision and Pattern Recognition, 2016, pp. 2921-2929.

Zhou, B. et al., "Places: A 10 Million Image Database for Scene Recognition", IEEE Transactions on Pattern Analysis and Machine Intelligence, Jul. 2017, vol. 40, No. 6, pp. 1452-1464.

Zhou, S.K., et al., "A Review of Deep Learning in Medical Imaging: Imaging Traits, Technology Trends, Case Studies with Progress Highlights, and Future Promises", Proceedings of the IEEE, vol. 109, No. 5, (2021), pp. 820-838.

Zhou, Z. et al., "Fine-Tuning Convolutional Neural Networks for Biomedical Image Analysis: Actively and Incrementally", IEEE Conference on Computer Vision and Pattern Recognition, 2017, pp. 4761-4772.

Hurst, R.T. et al., "Incidence of Subclinical Atherosclerosis as a Marker of Cardiovascular Risk in Retired Professional Football Players," The American Journal of Cardiology, vol. 105, Issue 8, 2010, pp. 1107-1111.

Hutchinson, et al., "Overdiagnosis of Pulmonary Embolism by Pulmonary CT Angiography", American Journal of Roentgenology, vol. 205, No. 2, (2015), pp. 271-277.

Iizuka, S., et al., "Globally and Locally Consistent Image Completion," ACM Transactions on Graphics, vol. 36, No. 4, 2017, Article 107, pp. 107-107:14.

Ioffe, S., et al, "Batch Normalization: Accelerating Deep Network Training by Reducing Internal Covariate Shift," arXiv:1502.03167v3 [cs.LG], 2015, 11 pages.

Irvin, J. et al. "CheXpert: A Large Chest Radiograph Dataset with Uncertainty Labels and Expert Comparison," Proceedings of the AAAI Conference on Artificial Intelligence, vol. 33, No. 01, 2019, pp. 590-597.

Isensee, F. et al., "nnU-Net: a self-configuring method for deep learning-based biomedical image segmentation," Nature Methods vol. 18 No. 2, 2021, pp. 203-211.

Jamaludin, A. et al., "Self-supervised Learning for Spinal MRIs," Deep Learning in Medical Image Analysis and Multimodal Learning for Clinical Decision Support, 2017, Springer, Cham, pp. 294-302.

Japkowicz, N. et al., "The class imbalance problem: A systematic study", Intelligent Data Analysis, vol. 6, No. 5, Oct. 2002, pp. 429-449.

Jiang, J. et al, "Multiple Resolution Residually Connected Feature Streams for Automatic Lung Tumor Segmentation From CT Images," IEEE Transactions on Medical Imaging, vol. 38, No. 1, 2019, pp. 134-144.

Jing, L., et al, "Self-Supervised Visual Feature Learning with Deep Neural Networks: A Survey," IEEE Transactions on Pattern Analysis and Machine Intelligence, vol. 43, No. 11, 2021, pp. 4037-4058.

Käding, C. et al., "Fine-Tuning Deep Neural Networks in Continuous Learning Scenarios," in "Asian Conference on Computer Vision," 2016, Springer International Publishing, pp. 588-605.

Kang, G., et al, "PatchShuffle Regularization," arXiv preprint arXiv:1707.07103v1 [cs.CV], 2017, 10 pages.

Kingma, D., et al, "Adam: A Method for Stochastic Optimization," arXiv:1412.6980v5 [cs.LG], 2015, 13 pages.

Kirkpatrick, J. et al., "Overcoming catastrophic forgetting in neural networks," Proceedings of the National Academy of Sciences (PNAS) vol. 114 No. 3, 2017, pp. 3521-3526.

Kistler, M. et al, "The Virtual Skeleton Database: An Open Access Repository for Biomedical Research and Collaboration," Journal of Medical Internet Research, vol. 15, Issue. 11, 2013, e245, 14 pages.

Kolesnikov, A., et al, "Revisiting Self-Supervised Visual Representation Learning," Proceedings of the IEEE/CVF Conference on Computer Vision and Pattern Recognition (CVPR), 2019, pp. 1920-1929.

Kooi, T., et al., "Large scale deep learning for computer aided detection of mammographic lesions," Medical Image Analysis vol. 35 (2017), pp. 303-312.

Kovashka, A., et al., "Crowdsourcing in Computer Vision", arXiv preprint arXiv:1611.02145v1 [cs.CV, (2016), 69 pages.

(56) References Cited

OTHER PUBLICATIONS

Krizhevsky, A., et al, "ImageNet Classification with Deep Convolutional Neural Networks," Advances in Neural Information Processing Systems, vol. 25, 2012, pp. 1097-1105.

Kukar, M., "Transductive reliability estimation for medical diagnosis," Artificial Intelligence in Medicine vol. 29, No. 1, 2003, pp. 81-106.

Kulick, J. et al. "Active Learning of Hyperparameters: An Expected Cross Entropy Criterion for Active Model Selection," arXiv:1409.7552v1 [stat.ML], 2014, 10 pages.

Kuo, W. et al. "Cost-Sensitive Active Learning for Intracranial Hemorrhage Detection," Medical Image Computing and Computer Assisted Intervention—MICCAI 2018, 2018, Springer International Publishing, pp. 715-723.

Lecun, Y. et al., "Deep learning", Nature, May 2015, vol. 521, No. 7553, pp. 436-444.

Lecun, Y., et al., "Self-supervised learning is the key to human-level intelligence." ACM TechNews, VentureBeat, May 6, 2020, 6 pages.

Lee, C.Y. et al, "Deeply-Supervised Nets," in Artificial Intelligence and Statistics, PMLR, 2015, pp. 562-570.

Li, X. et al, "Partial Order Pruning: for Best Speed/Accuracy Trade-off in Neural Architecture Search," in Proceedings of the IEEE Conference on Computer Vision and Pattern Recognition, 2019, pp. 9137-9145.

Li, X. et al., "Adaptive Active Learning for Image Classification," Proceedings of the IEEE Conference on Computer Vision and Pattern Recognition, 2013, pp. 859-866.

Li, X. et al., "Transformation-Consistent Self-Ensembling Model for Semisupervised Medical Image Segmentation," IEEE Transactions on Neural Networks and Learning Systems, vol. 32, No. 2, 2020, pp. 523-534.

Liang, J. et al., "Computer Aided Detection of Pulmonary Embolism with Tobogganing and Multiple Instance Classification in CT Pulmonary Angiography", Biennial International Conference Information Processing in Medical Imaging, Springer, 2007, pp. 630-641.

Lin, G. et al, "RefineNet: Multi-Path Refinement Networks for High-Resolution Semantic Segmentation," in Proceedings of the IEEE Conference on Computer Vision and Pattern Recognition, vol. 1, 2017, pp. 5168-5177.

Lin, T.Y. et al, "Feature Pyramid Networks for Object Detection," in Proceedings of the IEEE Conference on Computer Vision and Pattern Recognition, 2017, pp. 936-944.

Litjens, G., et al, "A survey on deep learning in medical image analysis," Medical Image Analysis vol. 42, 2017, pp. 60-88.

Liu, C. et al, "Auto-DeepLab: Hierarchical Neural Architecture Search for Semantic Image Segmentation," in Proceedings of the IEEE Conference on Computer Vision and Pattern Recognition, 2019, pp. 82-92.

Liu, C. et al, "Progressive Neural Architecture Search," in Proceedings of the European Conference on Computer Vision (ECCV), 2018, pp. 19-34.

Liu, C., et al., "Are Labels Necessary for Neural Architecture Search?", in "European Conference on Computer Vision" (Springer, 2020), pp. 798-813.

Long, J. et al, "Fully Convolutional Networks for Semantic Segmentation," in Proceedings of the IEEE Conference on Computer Vision and Pattern Recognition, 2015, pp. 3431-3440.

Lu, L. et al., "Deep Learning and Convolutional Neural Networks for Medical Image Computing: Precision Medicine, High Performance and Large-Scale Datasets," Advances in Computer Vision and Pattern Recognition, 2017, Springer Publishing, 327 pages.

Ma, Y., et al, "Multi-Attention Network for Thoracic Disease Classification and Localization," ICASSP 2019-2019 IEEE International Conference on Acoustics, Speech and Signal Processing (ICASSP), 2019, pp. 1378-1382.

Mahapatra, D. et al., "Efficient Active Learning for Image Classification and Segmentation Using a Sample Selection and Conditional Generative Adversarial Network," International Conference on Medical Image Computing and Computer-Assisted Intervention, 2018, Springer International Publishing, pp. 580-588.

Mahendran, A., et al, "Cross Pixel Optical-Flow Similarity for Self-Supervised Learning," Asian Conference on Computer Vision, 2018, vol. 11365, 2019, Springer International Publishing, pp. 99-116.

Martin, K.A., et al., "Time Trends in Pulmonary Embolism Mortality Rates in the United States, 1999 to 2018", Journal of the American Heart Association vol. 9, No. 17, e016784 (2020), 9 pages.

McCallum, A.K. et al., Employing EM and Pool-Based Active Learning for Text Classification, ICML, vol. 98, 1998, (Citeseer 1998), pp. 359-367.

McCloskey, M. et al., "Catastrophic Interference in Connectionist Networks: The Sequential Learning Problem," Psychology of Learning and Motivation, vol. 24, 1989, pp. 109-165.

Menze, B.H., et al., "The Multimodal Brain Tumor Image Segmentation Benchmark (Brats)," IEEE Transactions on Medical Imaging, vol. 34, No. 10, 2015, pp. 1993-2024.

Meyer, M. G. et al, "The Cell-CT 3-Dimensional Cell Imaging Technology Platform Enables the Detection of Lung Cancer Using the Noninvasive LuCED Sputum Test," Cancer Cytopathology, vol. 123, No. 9, 2015, pp. 512-523.

Milletari, F. et al, "V-Net: Fully Convolutional Neural Networks for Volumetric Medical Image Segmentation," in Fourth International Conference on 3D Vision (3DV), 2016, pp. 565-571.

Moen, E. et al. "Deep learning for cellular image analysis," Nature Methods, vol. 16, No. 12, 2019, pp. 1233-1246.

Mundhenk, T. N. et al., "Improvements to context based self-supervised learning." 2018 IEEE/CVF Conference on Computer Vision and Pattern Recognition, 2018, pp. 9339-9348.

Mundt, M. et al., "A Wholistic View of Continual Learning with Deep Neural Networks: Forgotten Lessons and the Bridge to Active and Open World Learning," arXiv:2009.01797v1 [cs.LG], 2020, 32 pages.

Munjal, P. et al., "Towards Robust and Reproducible Active Learning Using Neural Networks," arXiv:2002.09564v1 [cs.LG] 2020, 15 pages.

Zhou, Z. et al., "Active, continual fine tuning of convolutional neural networks for reducing annotation efforts," Medical Image Analysis, vol. 71, Article 101997, 2021, 15 pages.

Zhou, Z. et al., "Integrating Active Learning and Transfer Learning for Carotid Intima-Media Thickness Video Interpretation," Journal of Digital Imaging, vol. 32, 2019, pp. 290-299.

Zhou, Z. et al., "Models Genesis: Generic Autodidactic Models for 3D Medical Image Analysis," Medical Image Computing and Computer Assisted Intervention, 2019, Springer International Publishing, pp. 384-393.

Zhou, Z. et al., "Unet++: A Nested U-Net Architecture for Medical Image Segmentation," Deep Learning in Medical Image Analysis and Multimodal Learning for Clinical Decision Support: 4th International Workshop, DLMIA, 2018, Springer International Publishing, pp. 3-11.

Zhou, Z., et al, "Models Genesis," Medical Image Analysis, vol. 67, Article 101840, 2021, 23 pages.

Zhou, Z., et al, "UNet++: Redesigning Skip Connections to Exploit Multiscale Features in Image Segmentation," IEEE Transactions on Medical Imaging, vol. 39, No. 6, 2020, pp. 1856-1867.

Zhu, J. et al., "Rubik's Cube+: A self-supervised feature learning framework for 3D medical image analysis," Medical Image Analysis, vol. 64, 2020, 101746, 11 pages.

Zhu, Q. et al, "Deeply-Supervised CNN for Prostate Segmentation," in International Joint Conference on Neural Networks (IJCNN), 2017, pp. 178-184.

Zhuang, X. et al., "Self-supervised Feature Learning for 3d Medical Images by Playing a Rubik's Cube," Medical Image Computing and Computer Assisted Intervention, 2019, Springer International Publishing, pp. 420-428.

Zoph, B. et al, "Learning Transferable Architectures for Scalable Image Recognition," in Proceedings of the IEEE Conference on Computer Vision and Pattern Recognition, 2018, pp. 8697-8710.

Zyuzin, V. et al, "Comparison of Unet architectures for segmentation of the left ventricle endocardial border on two-dimensional

(56) References Cited

OTHER PUBLICATIONS ultrasound images," in 2019 Ural Symposium on Biomedical Engineering, Radioelectronics and Information Technology (USBEREIT), 2019, pp. 110-113.
Nlst, "Reduced Lung-Cancer Mortality with Low-Dose Computed Tomographic Screening", The New England Journal of Medicine vol. 365, No. 5, 2011, pp. 395-409.
Noroozi, M. et al., "Unsupervised Learning of Visual Representations by Solving Jigsaw Puzzles," in European Conference on Computer Vision, 2016, Springer, pp. 69-84.
Noroozi, M., et al, "Boosting Self-Supervised Learning via Knowledge Transfer," 2018 IEEE/CVF Conference on Computer Vision and Pattern Recognition, 2018, pp. 9359-9367.
Ozdemir, F. et al., "Active Learning for Segmentation by Optimizing Content Information for Maximal Entropy," Deep Learning in Medical Image Analysis and Multimodal Learning for Clinical Decision Support, 2018, Springer International Publishing, pp. 183-191.
Pan, S. J. et al., "A Survey on Transfer Learning," IEEE Transactions on Knowledge and Data Engineering, vol. 22, No. 10, 2010, pp. 1345-1359.
Parisi, G.I. et al., "Continual lifelong learning with neural networks: A review," Neural Networks, 113, 2019, pp. 54-71.
Pathak, D. et al., "Context Encoders: Feature Learning by Inpainting," 2016 Proceedings of the IEEE Conference on Computer Vision and Pattern Recognition (CVPR), pp. 2536-2544.
Pauley, E., et al., "Age-Stratified National Trends in Pulmonary Embolism Admissions," Chest, vol. 156, Issue 4, Oct. 2019, pp. 733-742.
Perez, L., et al., "The Effectiveness of Data Augmentation in Image Classification using Deep Learning", arXiv preprint arXiv:1712.04621v1 [cs.CV] (2017), 8 pages.
Pohlen, T. et al, "Full-Resolution Residual Networks for Semantic Segmentation in Street Scenes," in Proceedings of the IEEE Conference on Computer Vision and Pattern Recognition, 2017, pp. 3309-3318.
Poplin, R., et al., "Prediction of cardiovascular risk factors from retinal fundus photographs via deep learning", Nature Biomedical Engineering vol. 2, No. 3, (2018), pp. 158-164.
Prasoon, A., et al., "Deep Feature Learning for Knee Cartilage Segmentation Using a Triplanar Convolutional Neural Network," in International Conference on Medical Image Computing and Computer-Assisted Intervention—MICCAI (2013), Springer, pp. 246-253.
Purushwalkam, S. et al. "Demystifying Contrastive Self-Supervised Learning: Invariances, Augmentations and Dataset Biases," arXiv:2007.13916v2 [cs.CV], 2020, 13 pages.
Raghu, M., et al, "Transfusion: Understanding Transfer Learning for Medical Imaging," arXiv preprint arXiv:1902.07208v1, 2019, 22 pages.
Ratner, A.J., et al., "Learning to Compose Domain-Specific Transformations for Data Augmentation," Advances in Neural Information Processing Systems, Voil. 30 (2017), 11 pages.
Ravizza, S. et al., "Predicting the early risk of chronic kidney disease in patients with diabetes using real-world data," Nature Medicine, vol. 25 Issue 1, 2019, pp. 57-59.
Rawat, W. et al., "Deep Convolutional Neural Networks for Image Classification: A Comprehensive Review," Neural Computation, vol. 29, No. 9, 2017, pp. 2352-2449.
Ren, P., et al., "A Survey of Deep Active Learning," arXiv:2009.00236v1 [cs.LG], 2020, 30 pages.
Ronneberger, O. et al., "U-Net: Convolutional Networks for Biomedical Image Segmentation," in International Conference on Medical Image Computing and Computer-Assisted Intervention, 2015, Springer, Cham., pp. 234-241.
Ross, T. et al., "Exploiting the potential of unlabeled endoscopic video data with self-supervised learning," International Journal of Computer Assisted Radiology and Surgery, vol. 13, 2018, pp. 925-933.
Roth, H. R, et al., "A New 2.5D Representation for Lymph Node Detection Using Random Sets of Deep Convolutional Neural Network Observations," Medical Image Computing and Computer-Assisted Intervention—MICCAI, 2014, Springer International Publishing, pp. 520-527.
Roth, H. R. et al., "Improving Computer-Aided Detection Using Convolutional Neural Networks and Random View Aggregation," IEEE Transactions on Medical Imaging, vol. 35, No. 5, 2016, pp. 1170-1181.
Rubin, G.D., et al., "Characterizing Search, Recognition, and Decision in the Detection of Lung Nodules on CT Scans: Elucidation with Eye Tracking", Radiology, vol. 274, No. , (2015), pp. 276-286.
Sabour, S. et al., "Dynamic Routing Between Capsules," arXiv:1710.09829v2 [cs.CV], 2017, 11 pages.
Sadigh, G. et al., "Challenges, Controversies, and Hot Topics in Pulmonary Embolism Imaging", American Journal of Roentgenology, Mar. 2011, vol. 196, No. 3, pp. 497-515.
Sayed, N., et al, "Cross and Learn: Cross-Modal Self-supervision," German Conference on Pattern Recognition, GCPR 2018, Lecture Notes in Computer Science, vol. 11269, 2019, Springer International Publishing, pp. 228-243.
Scheffer, T. et al., "Active Hidden Markov Models for Information Extraction," International Symposium on Intelligent Data Analysis, 2001, Springer Berlin Heidelberg, pp. 309-218.
Sener, O. et al., "Active Learning for Convolutional Neural Networks: A Core-Set Approach," arXiv preprint arXiv:1708.00489v4 [stat.ML], 2018, 13 pages.
Sener, O., et al., "A Geometric Approach to Active Learning for Convolutional Neural Networks," arXiv:1708.00489v1, 2017, 12 pages.
Setio, A.A.A. et al., "Pulmonary Nodule Detection in CT Images: False Positive Reduction Using Multi-View Convolutional Networks," IEEE Transactions on Medical Imaging, vol. 35, No. 5, 2016, pp. 1160-1169.
Setio, A.A.A. et al., "Validation, comparison, and combination of algorithms for automatic detection of pulmonary nodules in computed tomography images: the LUNA16 challenge," Medical Image Analysis 42, 2017, pp. 1-13.
Settles, B., "Active Learning Literature Survey", Computer Sciences Technical Report: 1648, University of Wisconsin-Madison, 2009, 47 pages.
Shannon, C., "A Mathematical Theory of Communication", The Bell System Technical Journal, Oct. 1948, vol. 27, No. 3, pp. 379-423.
Shao, W. et al., "Deep Active Learning for Nucleus Classification in Pathology Images," 2018 IEEE 15th International Symposium on Biomedical Imaging (ISBI 2018), 2018, pp. 199-202.
Shen, D. et al, "Deep Learning in Medical Image Analysis," Annual Review of Biomedical Engineering, vol. 19, 2017, pp. 221-248.
Shenoy, A. A., "Feature optimization of contact map predictions based on inter-residue distances and U-Net++ architecture," 2019, 71 pages.
Shi, F., et al., "Review of Artificial Intelligence Techniques in Imaging Data Acquisition, Segmentation and Diagnosis for COVID-19", IEEE Reviews in Biomedical Engineering, vol. 14, (2021), 12 pages.
Shi, X., et al., "An Active Learning Approach for Reducing Annotation Cost in Skin Lesion Analysis", International Workshop on Machine Learning in Medical Imaging (Springer, 2019), pp. 628-636.
Shin, H.C. et al., "Deep Convolutional Neural Networks for Computer-Aided Detection: CNN Architectures, Dataset Characteristics and Transfer Learning," IEEE Transactions on Medical Imaging, vol. 35, No. 5, 2016, pp. 1285-1298.
Shin, J. et al., "Automating Carotid Intima-Media Thickness Video Interpretation with Convolutional Neural Networks", Proceedings of the IEEE Conference on Computer Vision and Pattern Recognition, 2016, pp. 2526-2535.
Shorten, C., et al., "A survey on Image Data Augmentation for Deep Learning", Journal of Big Data, vol. 6, Article No. 60, (2019), 48 pages.
Shui, C. et al., "Deep Active Learning: Unified and Principled Method for Query and Training," International Conference on Artificial Intelligence and Statistics, PMLR, vol. 108, 2020, pp. 1308-1318.

(56) References Cited

OTHER PUBLICATIONS

Siddiquee, M.M.R. et al., "Learning Fixed Points in Generative Adversarial Networks: From Image-to-Image Translation to Disease Detection and Localization," 2019 IEEE/CVF International Conference on Computer Vision (ICCV), 2019, pp. 191-200.
Simonyan, K. et al., "Very Deep Convolutional Networks for Large-Scale Image Recognition," arXiv preprint arXiv:1409. 1556v1 [cs.CV], 2014, 10 pages.
Sodha, V.A., "Self-supervised Representation Learning via Image Out-painting for Medical Image Analysis", (2020), 37 pages.
Song, G. et al, "Collaborative Learning for Deep Neural Networks," in Neural Information Processing Systems (NeurIPS), 2018, 10 pages.
Sourati, J. et al., "Active Deep Learning with Fisher Information for Patch-Wise Semantic Segmentation," Deep Learning in Medical Image Analysis and Multimodal Learning for Clinical Decision Support, 2018, Springer International Publishing, pp. 83-91.
Sourati, J. et al., "Classification Active Learning Based on Mutual Information," Entropy, vol. 18, No. 51, 2016, 21 pages.
Sourati, J. et al., "Intelligent Labeling Based on Fisher Information for Medical Image Segmentation Using Deep Learning," IEEE Transactions on Medical Imaging vol. 38, No. 11, 2019, pp. 2642-2653.
Spitzer, H. et al., "Improving Cytoarchitectonic Segmentation of Human Brain Areas with Self-supervised Siamese Networks," Medical Image Computing and Computer Assisted Intervention— MICCAI 2018, Lecture Notes on Computer Science, vol. 11072, 2018, Springer International Publishing, pp. 663-671.
Aggarwal, U., et al. Active Learning for imbalanced Datasets. WACV 2020—IEEE Winter Conference on Applications of Computer Vision, Mar. 2020, pp. 1417-1426.
Alex, V. et al., "Semisupervised learning using denoising autoencoders for brain lesion detection and segmentation," Journal of Medical Imaging vol. 4, Issue 4, 2017, pp. 041311 to 041311-16.
Ardila, D. et al, "End-to-end lung cancer screening with three-dimensional deep learning on low-dose chest computed tomography," Nature Medicine, vol. 25, No. 6, 2019, pp. 954-961.
Aresta, G. et al., "iW-Net: an automatic and minimalistic interactive lung nodule segmentation deep network," Scientific reports, 9(1), 2019, pp. 1-9.
Armato III, S.G. et al, "The Lung Image Database Consortium (LIDC) and Image Database Resource Initiative (IDRI): A Completed Reference Database of Lung Nodules on CT Scans," Medical physics 38(2), 2011, pp. 915-931.
Azizi, S., et al. "Big Self-Supervised Models Advance Medical Image Classification", Proceedings of the IEEE/CVF International Conference on Computer Vision (ICCV), 2021, pp. 3458-3468.
Bakas, S. et al., "Identifying the Best Machine Learning Algorithms for Brain Tumor Segmentation, Progression Assessment, and Overall Survival Prediction in the BRATS Challenge," arXiv:1811. 02629v3 [cs.CV], 2019, 49 pages.
Balcan, M.-F., et al. "Margin Based Active Learning", in "International Conference on Computational Learning Theory", pp. 35-50 (Springer,2007).
Bar, Y., et al. "Chest Pathology Detection Using Deep Learning with Non-Medical Training", in 2015 IEEE 12th International Symposium on Biomedical Imaging (ISBI), (IEEE, 2015), pp. 294-297.
Baumgartner, C. F. et al, "Visual Feature Attribution using Wasserstein GANs," in Proceedings of the IEEE Conference on Computer Vision and Pattern Recognition (CVPR), 2018, pp. 8309-8319.
Beck, A. H., et al. "Systematic Analysis of Breast Cancer Morphology Uncovers Stromal Features Associated with Survival", Science Translational Medicine Vo. 3, Issue 108, Article 108ra113 (2011), 11 pages.
Beluch, W.H. et al., "The power of ensembles for active learning in image classification," Proceedings of the IEEE Conference on Computer Vision and Pattern Recognition, 2018, pp. 9368-9377.
Ben-Cohen, A., et al, "Fully Convolutional Network for Liver Segmentation and Lesions Detection," in Deep Learning and Data Labeling for Medical Applications (2016), Springer , pp. 77-85.
Bilic, P. et al., "The Liver Tumor Segmentation Benchmark (LiTS)," arXiv preprint arXiv:1901.04056v1 [cs.CV], 2019, 43 pages.
Blackmon, K. N., et al. "Computer-aided detection of pulmonary embolism at CT pulmonary angiography: can it improve performance of inexperienced readers?", European Radiology vol. 21, No. 6, 2011, pp. 1214-1223.
Borisov, A. et al., "Active Batch Learning with Stochastic Query-by-Forest (SQBF)", JMLR: Workshop and Conference Proceedings, 2010 (published 2011), vol. 16, pp. 59-69.
Bortsova, G. et al., "Semi-supervised Medical Image Segmentation via Learning Consistency Under Transformations," Medical Image Computing and Computer Assisted Intervention—MICCAI 2019: 22nd International Conference, Shenzhen, China, Oct. 13-17, 2019, Proceedings, Part VI 22, 2019, Springer International Publishing, pp. 810-818.
Buda, M. et al., "A systematic study of the class imbalance problem in convolutional neural networks," Neural Networks, 106, 2018, pp. 249-259.
Cai, J. et al, "Iterative Attention Mining for Weakly Supervised Thoracic Disease Pattern Localization in Chest X-Rays," in International Conference on Medical Image Computing and Computer-Assisted Intervention, 2018, Springer, Cham, pp. 589-598.
Calder, K. et al., "The Mortality of Untreated Pulmonary Embolism in Emergency Department Patients", Annals of Emergency Medicine, Mar. 2005, vol. 45, No. 3, pp. 302-310.
Cardona, A. et al, "An Integrated Micro-and Macroarchitectural Analysis of the *Drosophila* Brain by Computer-Assisted Serial Section Electron Microscopy," PLoS Biology, vol. 8, No. 10, 2010, e1000502, 17 pages.
Caron, M. et al., "Deep Clustering for Unsupervised Learning of Visual Features," in Proceedings of the European Conference on Computer Vision (ECCV), 2018, pp. 139-156.
Caron, M. et al., "Unsupervised Learning of Visual Features by Contrasting Cluster Assignments," arXiv:2006.09882v1 [cs.CV], 2020, 21 pages.
Caron, M. et al., "Unsupervised Pre-Training of Image Features on Non-Curated Data," Proceedings of the IEEE International Conference on Computer Vision, 2019, pp. 2959-2968.
Carreira, J. et al., "Quo Vadis, Action Recognition? A New Model and the Kinetics Dataset," in 2017 IEEE Conference on Computer Vision and Pattern Recognition (CVPR), (Jul. 2017), pp. 4724-4733.
Chakraborty, S. et al., "Active Batch Selection via Convex Relaxations with Guaranteed Solution Bounds", IEEE Transactions on Pattern Analysis and Machine Intelligence, Oct. 2015 (Date of Publication: Jan. 12, 2015), vol. 37, No. 10, pp. 1945-1958.
Charoentong, P., et al. "Pan-cancer Immunogenomic Analyses Reveal Genotype-Immunophenotype Relationships and Predictors of Response to Checkpoint Blockade", Cell reports vol. 18, No. 1, 2017, pp. 248-262.
Chartrand, G. et al, "Deep Learning: A Primer for Radiologists," Radiographics, vol. 37, No. 7, 2017, pp. 2113-2131.
Chaurasia, A. et al, "LinkNet: Exploiting Encoder Representations for Efficient Semantic Segmentation," arXiv:1707.03718v1 [cs. CV], 2017, 5 pages.
Chen, H. et al, "Deep Contextual Networks for Neuronal Structure Segmentation," in Thirtieth AAAI conference on artificial intelligence, 2016, pp. 1167-1173.
Chen, L. et al., "Self-supervised learning for medical image analysis using image context restoration," Medical Image Analysis, vol. 58, 2019, 12 pages, https://doi.org/10.1016/j.media.2019.101539.
Chen, S. et al., "Med3D: Transfer Learning for 3D Medical Image Analysis," arXiv preprint arXiv:1904.00625v4 [cs.CV], 2019, 12 pages.
Chen, T. et al., "A Simple Framework for Contrastive Learning of Visual Representations," arXiv:2002.05709v1 [cs.CV], 2020, 17 pages.
Chen, T. et al., "Self-Supervised GANs via Auxiliary Rotation Loss," 2019 IEEE /CVF Conference on Computer Vision and Pattern Recognition (CVPR), 2019, pp. 12146-12155.

(56) References Cited

OTHER PUBLICATIONS

Chen, X. et al., "Exploring Simple Siamese Representation Learning," arXiv preprint arXiv:2011.10566v1 [cs.CV], 2020, 10 pages.

Cheng, J.-Z., et al. "Computer-Aided Diagnosis with Deep Learning Architecture: Applications to Breast Lesions in US Images and Pulmonary Nodules in CTScans", Scientific Reports 6, 1, Article 24454 (2016), 13 pages.

Cicero, M., et al. "Training and Validating a Deep Convolutional Neural Network for Computer-Aided Detection and Classification of Abnormalities on Frontal Chest Radiographs", Investigative Radiology vol. 52, No. 5, (2017), pp. 281-287.

Ciompi, F. et al, "Automatic classification of pulmonary perifissural nodules in computed tomography using an ensemble of 2D views and a convolutional neural network out-of-the-box," Medical Image Analysis, vol. 26, No. 1, 2015, pp. 195-202.

Cireşan, D., et al. "Mitosis Detection in Breast Cancer Histology Images with Deep Neural Networks", in International Conference on Medical Image Computing and Computer-Assisted Intervention, (Springer, 2013), pp. 411-418.

Cubuk, E. D., et al., "AutoAugment: Learning Augmentation Strategies from Data", in "Proceedings of the IEEE Conference on Computer Vision and Pattern Recognition", (2019), pp. 113-123.

Cui, W. et al., "Semi-supervised Brain Lesion Segmentation with an Adapted Mean Teacher Model," Information Processing in Medical Imaging: 26th International Conference, IPMI 2019, Hong Kong, China, Jun. 2-7, 2019, Proceedings 26, 2019, Springer International Publishing, pp. 554-565.

Culotta, A. et al., "Reducing Labeling Effort for Structured Prediction Tasks," AAAI, vol. 5, 2005, pp. 746-751.

Dagan, I., et al., "Committee-Based Sampling for Training Probabilistic Classifiers", in Machine Learning Proceedings (Elsevier, 1995), pp. 150-157.

Dao, T., et al. "A Kernel Theory of Modern Data augmentation", Proceedings of Machine Learning Research Vo. 97, 1528 (2019), pp. 1528-1537.

Das, M., et al., "Computer-aided detection of pulmonary embolism: influence on radiologists' detection performance with respect to vessel segments", European Radiology 18, 7, (2008), pp. 1350-1355.

De Fauw, J., et al., "Clinically applicable deep learning for diagnosis and referral in retinal disease", Nature Medicine vol. 24, No. 9, 2018, pp. 1342-1350.

Deng, J. et al., "ImageNet: A Large-Scale Hierarchical Image Database," 2009 IEEE Conference on Computer Vision and Pattern Recognition, 2009, pp. 248-255.

Dietterich, T. G., "Ensemble Methods in Machine Learning," in International Workshop on Multiple Classifier Systems, 2000, Springer, Berlin, Heidelberg, pp. 1-15.

Ding, Y. et al., "A Deep Learning Model to Predict a Diagnosis of Alzheimer Disease by Using 18F-FDG PET of the Brain," Radiology, vol. 290, No. 2, 2019, pp. 456-464.

\* cited by examiner

Table 2.1

| Pattern | Example | + Entropy − Majority | + Entropy + Majority | + Diversity − Majority | + Diversity + Majority |
|---|---|---|---|---|---|
| A | 0.4 0.4 0.4 0.5 0.5 0.5 0.5 0.5 0.6 0.6 0.6 | 7.52 | 2.02 | 4.38 | 0.00 |
| B | 0.4 0.4 0.4 0.5 0.5 0.5 0.5 0.5 0.6 0.6 0.6 | 4.57 | 0.83 | 1237.21 | 20.79 |
| C | 0.4 0.4 0.4 0.5 0.5 0.5 0.5 0.5 0.6 0.6 0.6 | 1.30 | 0.00 | 2816.66 | 0.00 |
| D | 0.4 0.4 0.4 0.5 0.5 0.5 0.5 0.5 0.6 0.6 0.6 | 1.30 | 0.00 | 189.54 | 0.00 |
| E | 0.4 0.4 0.4 0.5 0.5 0.5 0.5 0.5 0.6 0.6 0.6 | 1.30 | 0.00 | 189.54 | 0.00 |
| F | 0.4 0.4 0.4 0.5 0.5 0.5 0.5 0.5 0.6 0.6 0.6 | 3.24 | 0.33 | 1076.87 | 13.54 |
| G | 0.4 0.4 0.4 0.5 0.5 0.5 0.5 0.5 0.6 0.6 0.6 | 3.24 | 0.33 | 1076.87 | 13.54 |

FIG. 1A

Table 3.3

| Architecture | DS | Params | 2D Application | | | | | Architecture | DS | Params | 3D Application |
| --- | --- | --- | --- | --- | --- | --- | --- | --- | --- | --- | --- |
| | | | EM | Cell | Nuclei | BraTS | Liver | | | | Lung Nodule |
| U-Net | ✗ | 7.8M | 88.30±0.24 | 88.73±1.64 | 90.57±1.26 | 89.21±1.55 | 79.90±1.38 | V-Net | ✗ | 22.6M | 71.17±4.53 |
| wide U-Net | ✗ | 9.1M | 88.37±0.13 | 88.91±1.43 | 90.47±1.15 | 89.35±1.49 | 80.25±1.31 | wide V-Net | ✗ | 27.0M | 73.12±3.99 |
| UNet++ | ✗ | 8.7M | 88.39±0.15 | 90.71±1.25 | 91.73±1.09 | 90.70±0.38 | 79.62±1.30 | VNet++ | ✗ | 25.3M | 75.93±3.96 |
| UNet++ | ✓ | 8.7M | 88.89±0.12 | 91.19±1.13 | 92.04±0.99 | 91.15±0.63 | 82.83±0.92 | VNet++ | ✓ | 25.3M | 76.72±3.48 |
| UNet++ | ✗ | 9.0M | 88.92±0.14 | 91.06±1.34 | 92.44±1.20 | 90.86±0.61 | 82.51±1.39 | VNet+++ | ✗ | 26.2M | 76.94±3.11 |
| UNet+++ | ✓ | 9.0M | 89.33±0.10 | 91.21±0.98 | 92.57±0.98 | 91.21±0.68 | 82.80±1.11 | VNet+++ | ✓ | 26.2M | 77.05±2.42 |

[1] The winner in BraTS-2013 holds a "complete" Dice of 92% vs. 90.83%±2.46% (Unet++ with deep supervision).

FIG. 1B

Table 4.3

| Pre-training | Approach | Target tasks | | | | | |
|---|---|---|---|---|---|---|---|
| | | MCC (%) | NCS (%) | ECC (%) | LCS (%) | BMS (%) |
| No | Random with Uniform Init | 94.74±1.97 | 75.48±0.43 | 80.36±3.58 | 78.68±4.23 | 60.70±1.60 |
| | Random with Xavier Init | 94.22±5.07 | 74.05±1.97 | 79.99±8.06 | 77.92±3.97 | 58.52±2.61 |
| | Random with MSRA Init | 96.03±1.82 | 76.44±0.45 | 78.24±3.60 | 79.76±5.43 | 63.00±1.73 |
| (Fully) supervised | I3D | 98.26±0.27 | 71.58±0.55 | 80.55±1.11 | 70.65±4.26 | 67.83±0.75 |
| | NiftyNet | 94.14±4.57 | 52.98±2.05 | 77.33±8.05 | 83.23±1.05 | 60.78±1.60 |
| | MedicalNet | 95.80±0.49 | 75.68±0.32 | 86.43±1.44 | 85.52±0.58 | 66.09±1.35 |
| Self-supervised | De-noising | 95.92±1.83 | 73.09±0.62 | 85.14±3.02 | 84.86±0.96 | 57.83±1.57 |
| | In-painting | 91.46±2.97 | 76.02±0.55 | 79.70±3.55 | 81.36±4.83 | 61.38±3.84 |
| | Jigsaw | 95.47±1.24 | 70.80±1.55 | 81.79±1.04 | 82.04±1.26 | 63.33±1.11 |
| | DeepCluster | 97.22±0.55 | 74.85±0.46 | 84.82±0.62 | 82.66±1.00 | 65.96±0.85 |
| | Patch shuffling | 91.93±2.22 | 75.74±0.51 | 82.15±3.30 | 82.82±2.35 | 59.95±6.92 |
| | Rubik's Cube | 96.24±1.97 | 72.57±0.16 | 80.49±4.64 | 75.59±0.20 | 62.75±1.93 |
| | Genesis Chest CT (ours) | 98.34±0.44 | 77.62±0.64 | 87.20±2.87 | 85.10±2.15 | 67.96±1.29 |

FIG. 1C

Table 5.1

| Task: ECC (w/o VOIR) | Random | Models ImageNet | Models Genesis |
|---|---|---|---|
| 2D slice-based input | 60.33±8.61 | 62.57±8.04 | 62.84±8.78 |
| 2.5D orthogonal input | 71.27±4.64 | 78.61±3.73 | 78.58±3.67 |
| 3D volume-based input | 80.36±3.58 | n/a | 88.04±1.40 |

| Task: ECC (w/t VOIR) | Random | ImageNet | Genesis |
|---|---|---|---|
| 2D slice-based input | 86.16±1.94 | 86.83±0.97 | 87.43±1.34 |
| 2.5D orthogonal input | 87.29±3.25 | 88.04±0.78 | 88.32±1.70 |
| 3D volume-based input | 92.01±0.98 | n/a | 92.81±0.47 |

FIG. 1D

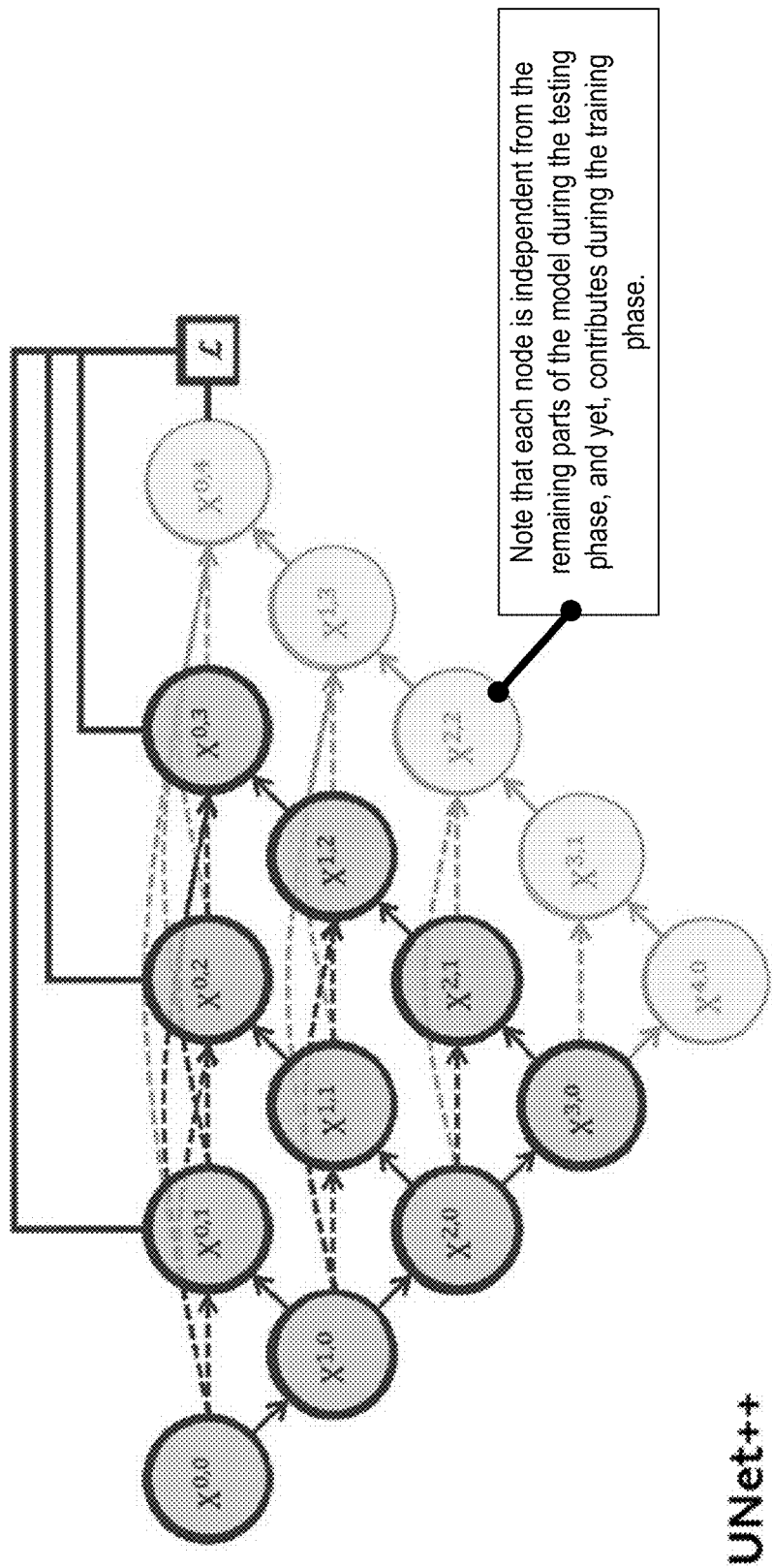

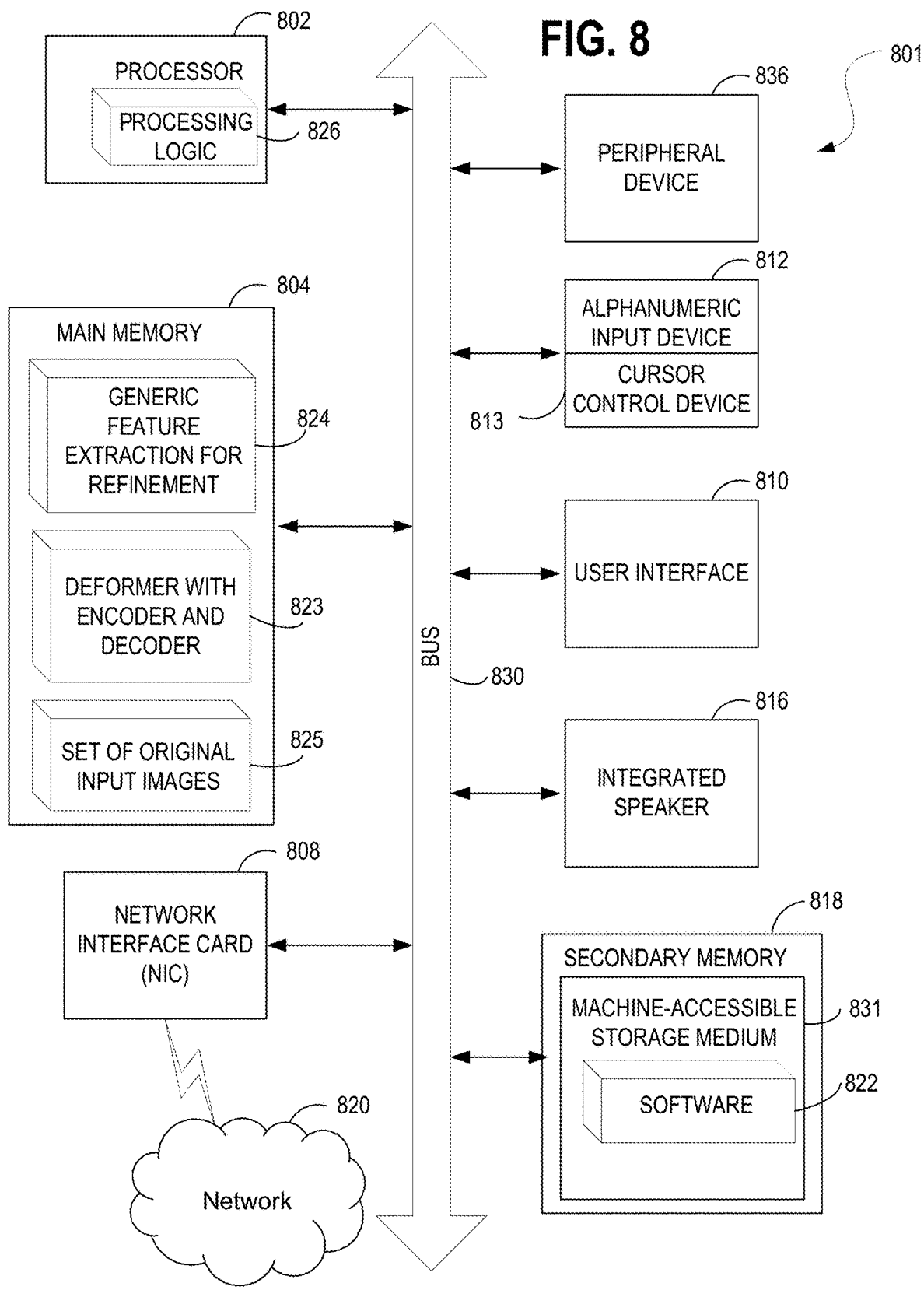

SYSTEMS, METHODS, AND APPARATUSES FOR IMPLEMENTING ADVANCEMENTS TOWARDS ANNOTATION EFFICIENT DEEP LEARNING IN COMPUTER-AIDED DIAGNOSIS

CLAIM OF PRIORITY

This non-provisional U.S. Utility Patent Application is related to, and claims priority to, the U.S. Provisional Patent Application No. 63/173,250, entitled "SYSTEMS, METHODS, AND APPARATUSES FOR IMPLEMENTING ADVANCEMENTS TOWARDS ANNOTATION EFFICIENT DEEP LEARNING IN COMPUTER-AIDED DIAGNOSIS," filed Apr. 9, 2021, and is further related to, and claims priority to, the U.S. Provisional Patent Application No. 63/188,981, entitled "SYSTEMS, METHODS, AND APPARATUSES FOR IMPLEMENTING ADVANCEMENTS TOWARDS ANNOTATION EFFICIENT DEEP LEARNING IN COMPUTER-AIDED DIAGNOSIS," filed May 14, 2021, the entire contents of each being incorporated herein by reference as though set forth in full.

GOVERNMENT RIGHTS AND GOVERNMENT AGENCY SUPPORT NOTICE

This invention was made with government support under RO1 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for implementing advancements towards annotation-efficient deep learning in computer-aided diagnosis, in which trained deep models are then utilized for the processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of over-fitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Problematically, annotating medical imaging is tedious and time-consuming, and demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

The described embodiments therefore provide enhanced solutions to improve upon conventionally known medical image processing and learning techniques by capturing the advancements towards annotation-efficient deep learning within specially configured computing systems specially designed to facilitate in computer-aided diagnosis.

The present state-of-the-art may therefore benefit from the systems, methods, and apparatuses for implementing advancements towards annotation-efficient deep learning in computer-aided diagnosis, as is described herein.

BRIEF DESCRIPTION OF THE DRAWINGS

Embodiments are illustrated by way of example, and not by way of limitation, and can be more fully understood with reference to the following detailed description when considered in connection with the figures.

FIG. 1A depicts Table 2.1, which illustrates an active selection patterns analysis, in accordance with disclosed embodiments;

FIG. 1B depicts Table 3.3, which illustrates semantic segmentation results measured by IoU (mean±s.d. %) for U-Net, wide U-Net, UNet+ (the described intermediate proposed methodology), and UNet++ (the described final proposed methodology), in accordance with disclosed embodiments;

FIG. 1C depicts Table 4.3, which show how Models Genesis lead the best or comparable performance on five distinct medical target tasks over six self-supervised learning approaches (revised in 3D) and three competing publicly available (fully) supervised pre-trained 3D models, in accordance with disclosed embodiments;

FIG. 1D depicts Table 5.1, which illustrates results from evaluating Vessel-Oriented Image Representation (VOIR) in comparison with 2D, 2.5D, and 3D solutions for the task of reducing PE false positives, in accordance with disclosed embodiments;

FIGS. 3D and 3E illustrate the use of a UNet++ model for improved segmentation accuracy, in accordance with disclosed embodiments;

FIG. 8 illustrates a diagrammatic representation of a machine in the exemplary form of a computer system, in accordance with one embodiment, within which a set of instructions, for causing the machine/computer system to perform any one or more of the methodologies discussed herein, may be executed.

DETAILED DESCRIPTION

Figure 2A:
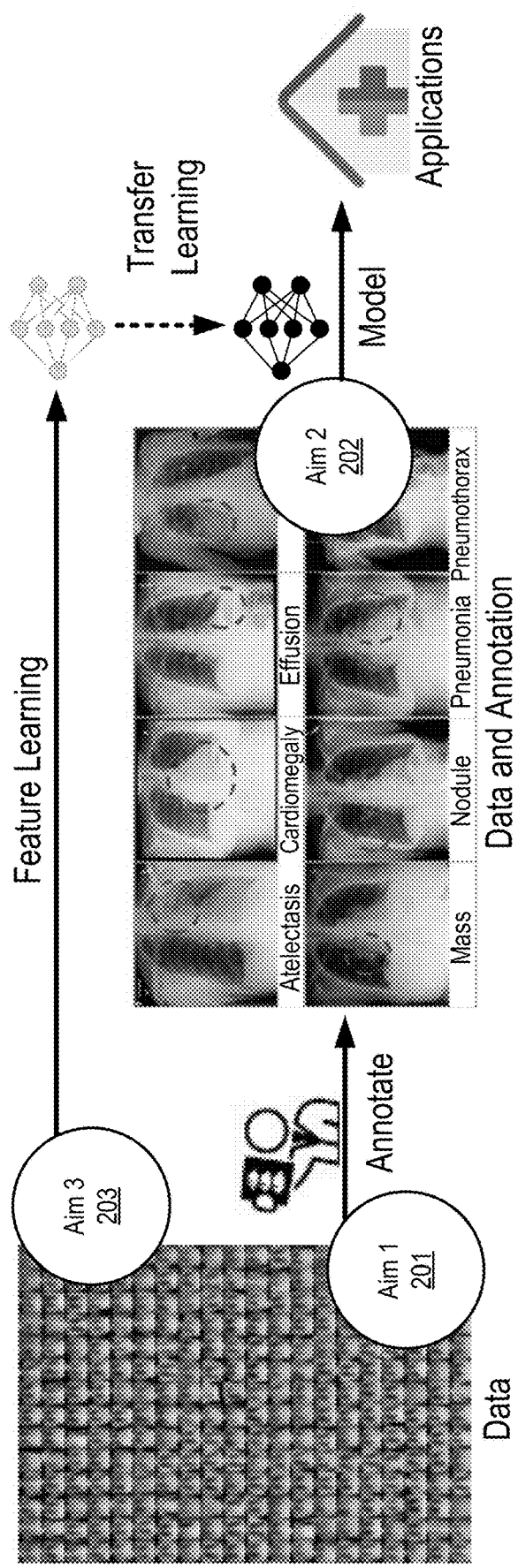
FIG. 2A depicts a methodology configured to minimize annotation cost, in accordance with described embodiments.

Described herein are systems, methods, and apparatuses for implementing advancements towards annotation-efficient deep learning in computer-aided diagnosis, in which trained deep models are then utilized in the context of medical imaging.

Introduction

Behind the great success of medical imaging, a crisis is looming. Specifically, the number of imaging studies, the workload of radiologists, and the health care cost related to imaging are rising rapidly. An unprecedented challenge is presented. Specifically, image data explosion-modern imaging systems generate enormous volumes of data, far exceeding human abilities for interpretation. What is critical, however, are not the images themselves, but rather the clinically relevant information contained within them. To automatically glean this information from medical images, deep learning holds great promise in improving diagnosis accuracy and efficiency.

Medical image analysis, for instance, benefits greatly from the recent advances in disease/organ detection, classification, and segmentation methodologies. There is no doubt that the impact of deep learning on medical imaging will be phenomenal. Indeed, in the near future, computers will interpret most medical images even before they reach a radiologist. Many studies have demonstrated promising results in complex diagnostics spanning dermatology, radiology, ophthalmology, and pathology. However, developing such systems is impeded by a significant barrier: deep learning is data hungry by nature, demanding large, high-quality annotated datasets; otherwise, deep learning often results in algorithms that perform poorly and lack generalizability on new data.

Annotating medical images is not only tedious and time consuming but it also requires costly, specialty-oriented knowledge and skills, which are not readily accessible. To overcome this barrier, the inventors describe herein innovative and annotation-efficient methodologies which operate by exploiting the intrinsic characteristics of medical images. The described methodologies seek to overcome a critical problem. Specifically: How to develop efficient and effective deep learning methods for medical applications where large annotated datasets are unavailable.

The dream of "big data" induces the misconception that more data brings the promise of higher performance, and thus, the present state-of-the-art is to continue asking human experts to annotate as many data as possible. However, the performance of deep models is not linearly correlated to the number of annotated data; instead, there comes the plateau where even annotating more data cannot further improve the accuracy. This is due to the inevitable noise inherent to all human expert annotations. Every task and model will encounter this bottleneck plateau. In essence, the number of annotated data that leads to the performance plateau is dependent on the complexity of the task, but it is also exceedingly influenced by the efficacy of the learning strategy and the capacity of the model architecture.

Such an observation therefore leads to the following hypothesis: With only a small part of the dataset annotated, deep models can approximate or even outperform prior known models that require annotating the entire dataset.

This hypothesis is based upon three pillars which are described in greater detail below with reference to FIG. 2A.

FIG. 1A depicts Table 2.1, which illustrates an active selection patterns analysis. Specifically shown here are the relationships among seven prediction patterns and four active selection criteria, assuming that a candidate $C_i$ has 11 augmented patches, and their probabilities $P_i$ are predicted by the current CNN, presented in the second column. With a majority selection, the entropy and diversity are calculated based on the top 25% (3 patches in this illustration) highest confidences on the dominant predicted category. The first choice of each method (represented by each column) is bolded and the second choice is underlined.

FIG. 1B depicts Table 3.3, which illustrates semantic segmentation results measured by IoU (mean±s.d. %) for U-Net, wide U-Net, UNet+ (the described intermediate proposed methodology), and UNet++ (the described final proposed methodology). Both UNet+ and UNet++ are evaluated with and without deep supervision (DS). The results depict the performance of an independent two sample t-test between U-Net vs. others for 20 independent trials and highlighted boxes in light gray when the differences are statistically significant (e.g., $p<0.05$).

FIG. 1C depicts Table 4.3, which show how Models Genesis lead the best or comparable performance on five distinct medical target tasks over six self-supervised learning approaches (revised in 3D) and three competing publicly available (fully) supervised pre-trained 3D models. For ease of comparison, the experiments evaluate AUC score for the two classification tasks (i.e., NCC and ECC) and IoU score for the three segmentation tasks (i.e., NCS, LCS, and BMS). All of the results, including the mean and standard deviation (mean±s.d.) across ten trials, reported in the table are evaluated using a customized dataset split. For every target task, The results depict the performance of an independent two sample t-test between the best (bolded) vs. others and highlighted light-gray boxes when they are not statistically significantly different at the $p<0.05$ level.

FIG. 1D depicts Table 5.1, which illustrates results from evaluating vessel-oriented image representation (VOIR) in comparison with 2D, 2.5D, and 3D solutions for the task of reducing PE false positives. The comprehensive experiments demonstrated that: (1) the vessel-oriented image representation exceeds the regular image representation; (2) The 3D volume-based inputs offer higher performance than 2.5D orthogonal inputs, which in turn work better than 2D slice-based inputs; and also (3) that Models Genesis consistently outperform models learning from scratch. Overall, the best performance is obtained by Models Genesis trained with 3D volume-based VOIR inputs. The entries in bold highlight the best results achieved by different model input formations. All of the results in the table are candidate-level AUC (Area Under the ROC Curve), including the mean and standard deviation (mean±s.d.) across ten trials.

Learning parameters were used for training and fine-tuning of AlexNet for AFT in the experiments. The term µ represents the momentum, $lr_{fc8}$ represents the learning rate of the weights in the last layer, α is the learning rate of the weights in the rest layers, and y determines how lr decreases over epochs. "Epochs" indicates the number of epochs used in each step. For ACFT, all the parameters are set to the same as AFT except the learning rate lr, which is set to 1/10 of that for AFT.

FIG. 2A depicts a methodology configured to minimize annotation cost, in accordance with described embodiments.

As shown here, novel techniques are described herein that accelerate model learning, elevate the overall accuracy, and establish robust performances with limited data. As a result, given the same amount of annotations, the described models yield higher performance or maintain the same performance, while requiring fewer annotations (refer to the dark vs. light learning curves).

The three pillars are therefore described as follows: Firstly, wisely selecting important samples can reduce the annotation cost in comparison with random selection. A common procedure of determining which sample needs to be annotated first by human experts is called "human-in-the-loop" active learning. Secondly, multi-scale feature aggregation in deep models can address tasks with higher complexity. Image segmentation, as an example, is one of the most complicated tasks in medical image analysis, demanding rich image features that span levels from low to high, and scales from small to large. Thirdly, deep models with general-purpose image representation can be built upon the consistent, recurrent anatomical structure embedded in medical images.

These generic models are therefore envisioned to serve as a primary source of transfer learning for many medical imaging tasks, even with limited annotated data.

The impact to the key facets of CAD systems is described in greater detail below in relation to the disclosed embodiments. First, some of the most distinguished characteristics of medical images are described, which establish the vital foundations and inspirations of the techniques presented herein. The clinical needs are then further described and imaging applications in healthcare are introduced in the context of the disclosed embodiments.

Then the various ways in which the described techniques improve performance and annotation efficiency are presented in relation to an exemplary CAD system configured for detecting pulmonary embolism from CTPA images.

Challenge & Opportunity: What is annotation? Annotation is the process of assigning labels to raw data in preparation for training the computer on the pairs of data and labels; then, the computer can predict labels for many new data. For the development of deep learning methods, supervised learning is the most prominent learning paradigm, in which the annotations are used to guide model learning and error propagating. Therefore, annotating datasets is an indispensable stage of data processing in the AI era. For natural imaging, data is collected from numerous photos from social media and annotations are often given by non-experts through crowd sourcing.

Annotating medical images, however, demands costly, specialty-oriented knowledge and skills, which are not easily accessible. Thereby, medical image annotations are done mainly by human experts, who manually and precisely annotate the existence, appearance, and severity of diseases in each medical image with the help of appropriate software tools. For some abnormalities that experts cannot immediately recognize from images, biopsy outcomes can also be used as annotations.

Figure 2B:
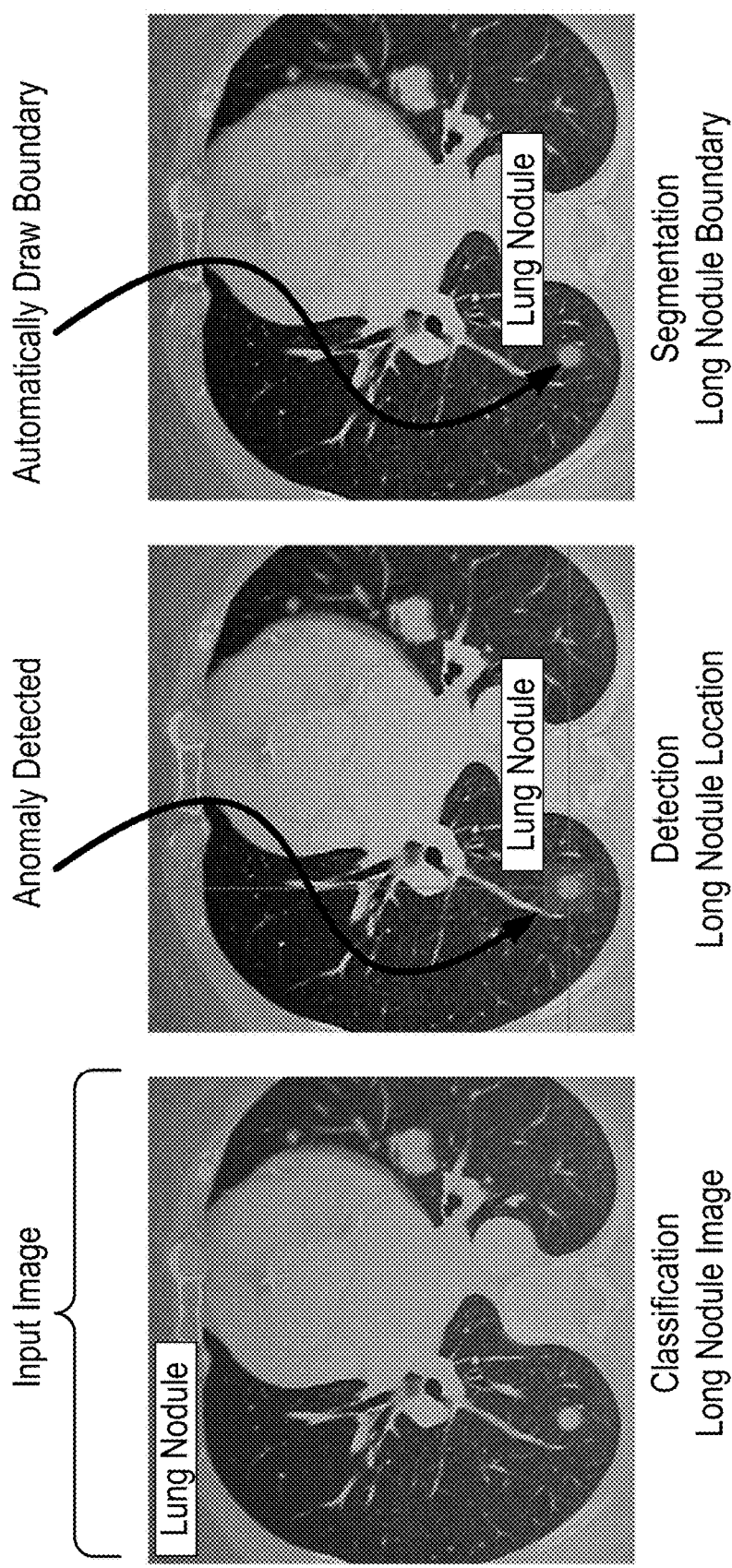
FIG. 2B illustrates different types of annotations in medical imaging, in accordance with described embodiments.

FIG. 2B illustrates different types of annotations in medical imaging, in accordance with described embodiments. Specifically, when harnessing large-scaled annotated datasets to advance medical imaging, the key question is what annotations should be collected. There are several types of annotations as per the task requirements in clinical practice. Different types of annotations come with different associated costs. For example, to annotate lung nodules for the tasks of classification, detection, and segmentation, human experts must consider different types of annotations and then label the existence of the nodule indicating its location, and drawing a contour of its boundary, respectively. These three types of annotation are anticipated to span manual annotation efforts from easy to hard, annotation qualities from coarse to fine, and annotation time from short to long.

Figure 2C:
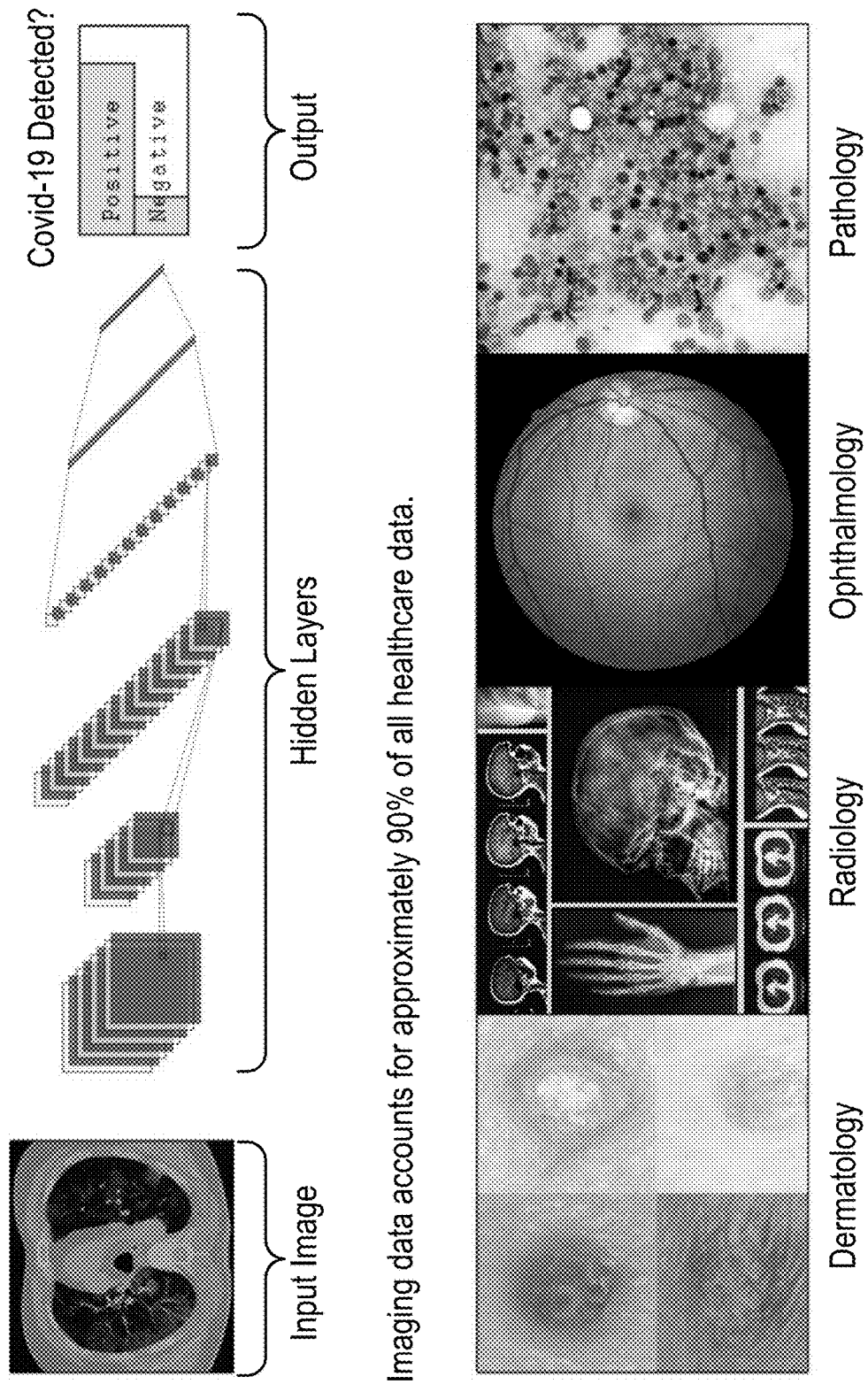
FIGS. 2C and 2D illustrate different types medical imaging data and exemplary anomaly detection applications in accordance with the described embodiments.
Figure 2D:
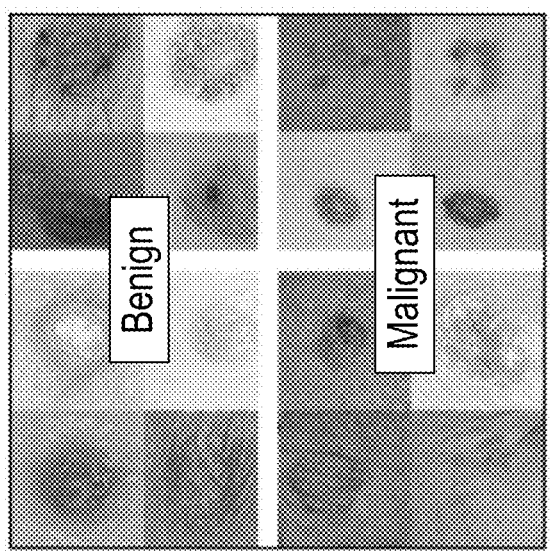
Figure 2D:
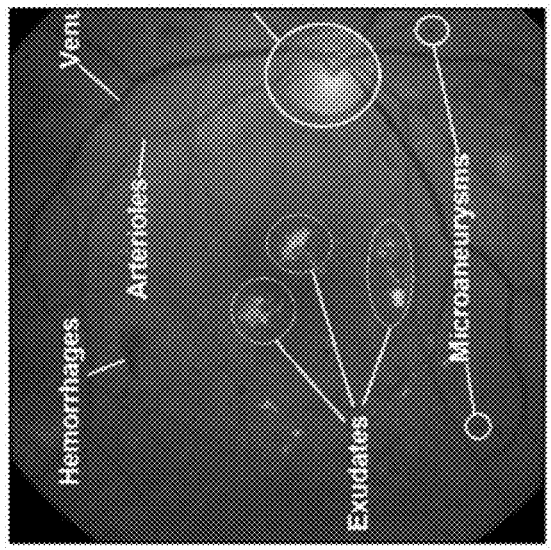
Figure 2D:
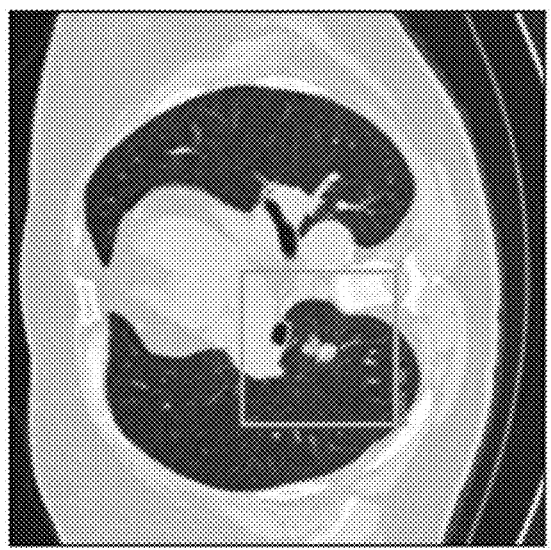

FIGS. 2C and 2D illustrate different types medical imaging data and exemplary anomaly detection applications in accordance with the described embodiments. Deep learning has huge impact in healthcare where imaging data accounts for approximately 90% of all healthcare data utilized across multiple disciplines, including dermatology, radiology, ophthalmology, and pathology, thus presenting one of the most important materials for clinical analysis and medical intervention. Deep learning becoming more popular than ever as it does not require hand crafted design features for specific imaging tasks and yet can automatically learn the image feature in an end-to-end manner using deep neural networks.

As an example, to train a deep model for lung cancer detection using prior known methods, human experts must tell the model where is the nodule, how big is the nodule, and whether the nodule is benign or malignant for every patient CT scan.

Consider the following scenarios, such as (i) a flood of patients during an outbreak, (ii) doctors lacking sufficient time and resources to annotate every case, and (iii) a lack of doctors with expertise for novel diseases. Practice of the annotation-efficient deep learning techniques as described herein enables the computer-aided diagnosis of rare diseases and rapid response to global pandemics, each of which are severely under-explored owing to the difficulty of collecting a sizable amount of labeled data.

To achieve a human-level lung cancer detection, more than 42 thousand CT images should be annotated in such a way A significant barrier—annotation acquisition: Deep learning methods are data hungry by nature, requiring large-scale, high-quality annotated datasets, much more so than other algorithms. Recent advances in AI systems suggest that to match human diagnostic precision, deep learning methods require 42,290 radiologist-labeled CT images for lung cancer diagnosis, 129,450 dermatologist-lab led images for skin cancer classification, and 128,175 ophthalmologist-labeled retinal images for diabetic retinopathy detection.

Without the availability of such large annotated datasets, deep learning often results in algorithms that perform poorly and lack generalizability on new data. Nonetheless, rarely is there a perfectly-sized and carefully-annotated dataset to train, validate, and test a deep learning model, particularly for applications in medical imaging, where both data and annotations are expensive to acquire. This requirement becomes more challenging in situations when quickly responding to global pandemics or when scaling up to several rare diseases where it is impractical to collect large quantities of annotated data.

Consequently, there is a pressing need for innovative methodologies that enable annotation-efficient deep learning for medical image analysis.

The opportunity of deep learning in medical imaging: Numerous opportunities present themselves through the use of deep learning when applied to the field of medical imaging.

First (1), the continual learning capabilities of deep learning incrementally improve the algorithm through fine-tuning. Millions of new medical images are generated in hospitals every day. With such a colossal stream of data, it is computationally impracticable to store the data in memory and repeatedly train computers from scratch once new data becomes available. Nevertheless, the hope is for computers to leverage the prior knowledge obtained from old data over time and continuously accommodate new data, like human beings.

Continual learning is built on the idea that learners adaptively use new data so their knowledge sets can develop autonomously and incrementally. The continual learning ability is one of the critical benefits that deep learning could offer. Unlike conventional machine learning methods, deep learning models can be fine-tuned on top of previously learned weights that often store the memories and knowledge of old data.

Techniques described herein specifically, take a set of trained weights and use it as model initialization for new data. The ability of continual learning would be much more appreciated in the scenario of the "human-in-the-loop" procedure, in which human experts interact with computers to promote the development of algorithms using a continuous stream of data.

An efficient "human-in-the-loop" procedure helps human experts quickly dismiss patients with negative results, therefore, dramatically reducing the burden of annotation. Moreover, an instant online feedback process encourages data, annotation, and model reuse, making it possible for CAD systems to self-improve via continual fine-tuning.

Secondly (2), the representation learning capabilities of deep learning relieve exhaustive feature engineering for specific medical conditions. Feature engineering manually designs features based on the texture and shape present in images, which are easier to describe and troubleshoot so humans can manipulate features on their own. However, crafting such features demands a great deal of patience, diligence, and expertise. Most handcrafted features focus on specific medical conditions, hence greatly limiting the expressive powers and depreciating the generalization capacity. For instance, radiomics features can be beneficial in radiological imaging, but they are not adaptable to other imaging modalities, such as dermatology, histopathology, and ophthalmology.

Recent deep learning methods swept away previous handcrafted features, showing that neural networks can solve diverse tasks by automatically learning hierarchical features at multiple levels of abstraction. In networks, each layer projects the image into a particular feature space—the deeper layer generates a higher level of abstraction by extracting more complex features built on top of simpler ones. The merit of deep learning is that the varying levels of features are not manually designed by humans.

For this technique which is referred to herein as "representation learning," a computer configured function executes processing to automatically learns visual features to represent an image. Representation learning is more efficient and repeatable than exhaustive feature engineering, saving tremendous amounts of manual work. Compared with hand-crafted features, deep features offer four distinct advantages: (i) deep features can be dynamically computed by models during training and test stages; (ii) deep features present a semantic hierarchy: varying from layer to layer; (iii) deep features can be used for not only classification but also registration, localization, and segmentation; and (iv) deep features can be fine-tuned and adapted to different tasks and domains. Many studies have reaffirmed that automated feature learning produces more generalizable image representation than hand-crafted features.

Thirdly (3), the consistent and recurrent anatomy embedded in medical images empowers deep learning with a generic visual representation. Human anatomies are intrinsically structured, exhibiting consistency in appearance, position, and layout. Medical imaging protocols focus on particular parts of the body, often generating images of great similarity and yielding an abundance of sophisticated anatomical patterns across patients. These patterns are naturally associated with comprehensive knowledge about human anatomy. Therefore, consistent and recurrent anatomy can ease the analysis of numerous critical problems and should be considered a significant advantage of medical imaging.

Due to the recurring anatomy, the same body parts in different images express similar visual patterns and, therefore, can be retrieved by what is known as a "nearest neighbor search." As a result, given a single annotated medical image, similar anatomical patterns can be found in many other images so that radiologists can track disease progress with landmark detection and lesion matching. In addition to correspondence matching, the recurrent anatomical structures in medical images are associated with rich knowledge about the human body and intrinsic structural coherence, offering great benefit and potential to foster image representation and produce more powerful source models. Consequently, one-shot or few-shot learning in various medical applications would be eventually actualized.

All these advantages have stimulated annotation-efficient deep learning and result in numerous emerging subjects, including the novel methodologies as described herein.

In the following section, the frontiers in technology are described in the context of the disclosed embodiments which are configured specifically to overcome the significant barrier of annotation acquisition by harnessing the three unique advantages noted above while demonstrating the novelty of the methodologies described herein.

Acquiring necessary annotations—One-time learning and continual learning: Pre-training a model on large-scale image datasets and then fine-tuning it on various target tasks has become a de-facto paradigm across many medical specialties. Nearly all leading approaches follow this paradigm to classify the common thoracic diseases on chest radiography by adopting different architectures along with their weights pre-trained from ImageNet. Other representative medical applications include identifying skin cancer from dermatologist level photographs diagnosing Alzheimer's Disease utilizing positron emission tomography with 2-deoxy-2-[fluorine-18]fluoro-D-glucose integrated with computed tomography, which is known by the label "$^{18}$F-FDG PET," a technique which has emerged as a powerful imaging tool for the detection of various cancers. Thus, other representative medical applications utilize images from the $^{18}$F-FDG PET image-set of the brain, and perform effective detection of pulmonary embolism from CTPA.

Recent breakthrough in self-supervised pre-training has led to visual representation that approaches and possibly surpasses what was learned from ImageNet. Self-supervised pre-training has also been adopted for the medical domain to develop generic CNNs that are directly pre-trained from medical images, mitigating the mandatory requirement of expert annotation and reducing the large domain gap between natural and medical images.

Despite the immense popularity of transfer learning in medical imaging, prior techniques exclusively employed one-time fine-tuning, thus simply fine-tuning a pre-trained CNN with available training samples for only one time. In real-world applications, instead of training on a still dataset, experts record new samples constantly and expect the samples to be used upon their availability; with the ability to deal with new data, continual learning is the bridge to active and open world learning approaches.

Compared with the existing continual learning the newly devised learning strategy described herein is more amenable to active fine-tuning because it focuses more on the newly annotated samples and also recognizes those misclassified ones, eliminating repeated training on those easy samples in the annotated pool.

Integrating active learning with deep learning: The uncertainty and diversity are the most compelling active selection criteria, which appraise the worthiness of annotating a sample from two different aspects. Uncertainty-based criteria argue that the more uncertain a prediction is, the more value added when including the label of that sample into the training set.

Sampling with least confidence, largest entropy, or margins of the prediction has been successful in training models with fewer labels than random sampling. The limitation of uncertainty-based criteria is that some of the selected samples are prone to redundancy and outliers and may not be representative enough for the data distribution as a whole.

Alternatively, diversity-based criteria have the advantage of selecting a set of most representative samples, related to the labeled ones, from those in the rest of the unlabeled set. The intuition is that there is no need to repeatedly annotate those samples with context information if the most representative one has already been covered. Rather, the use of mutual information, divergence, so called "Fisher information, K-centers, and core sets are calculated among either model predictions or image features, and are often used to ensure the diversity.

Although alleviating redundancy and outliers, a serious hurdle of diversity-based criteria is the computational complexity for a large pool of unlabeled samples. This issue is overcome by measuring diversity over patches augmented from the same sample, making the calculation much more manageable.

To exploit the benefits and potential of the two selecting aspects, the ACFT technique uses a mixed strategy of combing uncertainty and diversity explicitly. Conversely, prior known techniques compute the selection criteria from an ensemble of CNNs. Such prior approaches are, however, very costly in computation, as they must train a set of models to compute their uncertainty measure based the disagreements amongst the trained models. For additional active learning methods, Such existing methods are fundamentally different from the improved ACFT methodology described herein insomuch that they are all repeatedly re-trained CNNs from scratch at each step, whereas the improved ACFT methodology continually fine-tunes the (fine-tuned) CNN incrementally. As a result, the described ACFT methodology offers several advantages over prior methodologies and leads to dramatic annotation cost reduction and computation efficiency.

Moreover, it was found that there are only seven fundamental patterns in CNN predictions (refer to Table 2.1 presented at FIG. 1A). Multiple methods may be developed to select a particular pattern, such as entropy, Gaussian distance, and standard deviation would seek Pattern A, while diversity, variance, and divergence look for Pattern C.

The described technique is the first to analyze the prediction patterns in active learning and investigate the effectiveness of typical patterns rather than comparing the many methods.

Designing advanced architectures—Skip connections: Skip connections were first proposed for use within Fully Convolutional Networks (FCN) for semantic segmentation.

Shortly after, building on skip connections, the U-Net architecture was proposed for semantic segmentation in medical images. The FCN and U-Net architectures however differ in how the up-sampled decoder feature maps were fused with the same-scale feature maps from the encoder network. While FCN uses the summation operation for feature fusion, the U-Net architecture concatenates the features followed by the application of convolutions and nonlinearities. The skip connections have shown to help recover the full spatial resolution making fully convolutional methods suitable for semantic segmentation. Skip connections have further been used in modern neural architectures such as residual networks and dense networks facilitating the gradient flow and improving the overall performance of classification networks.

Aggregating multi-scale features: The exploration of aggregating hierarchical features has recently been the subject of research, including GridNet, which is an encoder-decoder architecture wherein the feature maps are wired in a grid fashion, generalizing several classical segmentation architectures. Although GridNet contains multiple streams with different resolutions, it lacks up-sampling layers between skip connections; and thus, it does not represent UNet++.

Full-Resolution Residual Networks (FRRN) employ a two-stream system, where full-resolution information is carried in one stream and context information in the other pooling stream. Two improved versions of FRRN have been proposed, including use of an incremental Multiple Resolution Residually-connected Network (MRRN) with 28.6 million parameters and dense MRRN with 25.5 million parameters. These 2D architectures, however, have similar number of parameters to the described 3D UNet++ and three times more parameters than 2D UNet++; and thus, simply upgrading these architectures to a 3D manner may not be amenable to the common 3D volumetric medical imaging applications.

Notably, redesigned dense skip connections utilized by the techniques described herein are completely different from those used in MRRN, which consists of a common residual stream. In addition, it is not flexible to apply the design of MRRN to other backbone encoders and meta framework such as Mask R-CNN. Still further, the Deep Layer Aggregation (DLA) topologically operates equivalent to the intermediate architecture of UNet+, and sequentially connects the same resolution of feature maps, without long skip connections as used in U-Net. Experimental results demonstrate that by densely connecting the layers, UNet++ achieves higher segmentation performance than UNet+/DLA as depicted at Table 3.3 presented at FIG. 1B.

Introducing deep supervision: With respect to deep supervision, the depth d of a network can act as a regularizer. Deeply supervised layers can improve the learning ability of the hidden layer, enforcing the intermediate layers to learn discriminative features enabling fast convergence and regularization of the network. DenseNet performs a similar deep supervision in an implicit fashion. Deep supervision can be used in U-Net like architecture as well. Use of deep supervision combining predictions from varying resolutions of feature maps suggests that it can combat potential optimization difficulties and thus reach faster convergence rate and more powerful discrimination capability.

The methodologies described herein utilize nested networks which are more amenable to training under deep supervision: Specifically recognized improvements include: 1) multiple decoders automatically generate full resolution segmentation maps; 2) the networks are embedded various different depths of U-Net so that it grasps multi-resolution features; 3) densely connected feature maps help smooth the gradient flow and give relatively consistent predicting mask; and 4) the high dimension features have effects on all outputs through back-propagation, allowing the described technique to be specifically configured to prune the network during the inference phase.

Extracting generic image features: With the splendid success of deep neural networks, transfer learning has become integral to many applications, especially medical imaging This immense popularity of transfer learning is attributed to the learned image representation, which offers convergence speedups and performance gains for most target tasks, in particular, with limited annotated data. In the following sections, works related to supervised and self-supervised representation learning are reviewed.

Supervised representation learning: ImageNet contains more than fourteen million images that have been manually annotated to indicate which objects are present in each image; and more than one million of the images have actually been annotated with the bounding boxes of the objects in the image. Pre-training a model on ImageNet and then fine-tuning it on different medical imaging tasks has seen the most practical adoption in medical image analysis Despite the remarkable transferability of Models ImageNet, pre-trained 2D models offer little benefit towards 3D medical imaging tasks in the most prominent medical modalities (e.g., CT and MRI). To fit this paradigm, 3D imaging tasks have to be re-formulated and solved in 2D or 2.5D thus losing rich 3D anatomical information and inevitably compromising the performance. Annotating 3D medical images at the similar scale with ImageNet requires a significant research effort and budget. It is currently not feasible to create annotated datasets comparable to this size for every 3D medical application. Consequently, for lung cancer risk malignancy estimation, resorted to incorporating 3D spatial information by using Inflated 3D (I3D), trained from the Kinetics dataset, as the feature extractor. As evidenced by Table 4.3 presented at FIG. 1C, it is not the most favorable choice owing to the large domain gap between the temporal video and medical volume. This limitation has led to the development of model zoo in NiftyNet However, they were trained with small datasets for specific applications (e.g., brain parcellation and organ segmentation and were never intended as source models for transfer learning.

The experimental results in Table 4.3 (refer to FIG. 1C) indicate that NiftyNet models offer limited benefits to the five target medical applications via transfer learning. Other techniques utilize a pre-trained 3D residual network by jointly segmenting the objects annotated in a collection of eight medical datasets, resulting in MedicalNet for 3D transfer learning. In Table 4.3 (refer again to FIG. 1C) the pre-trained MedicalNet is examined on five target tasks in comparison with Models Genesis. As reviewed, each and every aforementioned pre-trained model requires massive high-quality annotated datasets. However, seldom is there a perfectly-sized and systematically-labeled dataset to pre-train a deep model in medical imaging, where both data and annotations are expensive to acquire. The above limitation are thus overcome via self-supervised learning, which allows models to learn image representation from abundant unlabeled medical image data with zero human annotation effort.

Self-supervised representation learning: Aiming at learning image representation from unlabeled data, self-supervised learning research has recently experienced a surge in computer vision but it is a relatively new trend in modern medical imaging. The key challenge for self-supervised learning is identifying a suitable self supervision task, and specifically generating input and output instance pairs from the data.

Prior techniques included predicting the distance and 3D coordinates of two patches randomly sampled from the same brain identifying whether two scans belong to the same person, and predicting the level of vertebral bodies Nevertheless, such methodologies are incapable of learning representation from "self-supervision" because they demand auxiliary information and specialized data collection such as paired and registered images.

By utilizing only the original pixel/voxel information shipped with data, several self-supervised learning schemes have been developed for different medical applications, including: techniques which adopted colorization as proxy task wherein color colonoscopy images are converted to gray-scale and then recovered using a conditional Generative Adversarial Network (GAN); techniques which pretrained a stack of de-noising auto-encoders, in which the self-supervision was created by mapping the patches with the injected noise to the original patches; techniques which designed image restoration as proxy task, in which small regions were shuffled within images and then let models learn to restore the original ones; techniques which introduced a 3D representation learning proxy task by recovering the rearranged and rotated Rubik's cube; and finally techniques which individualized self-supervised schemes for a set of target tasks.

As seen, the previously discussed self-supervised learning schemes, both in computer vision and medical imaging, are developed individually for specific target tasks, therefore, the generalizability and robustness of the learned image representation have yet to be examined across multiple target tasks. The techniques described herein are the first to investigate and leverage cross-domain self-supervised learning in medical imaging.

Interpreting Medical Images

In modern medical practice, medical image interpretation has largely been conducted by human experts such as radiologists and other physicians. However, owing to the wide variety of medical pathology that may affect human beings, the limitations of human perception, and human fatigability, an increasing role for computer-aided diagnosis (CAD) in medicine has been recognized. In the past few years, the interest in artificial intelligence applications in medical imaging has mushroomed within medical imaging, driven primarily by remarkable advances in deep learning.

Advancements in the fields of active learning, model designing, and self-supervised learning have found a myriad of applications in medical image analysis, propelling it forward at a rapid pace. Computers naturally excel at discovering and recognizing intricate patterns from images while also providing quantitative assessments for medical imaging. As a result, CAD systems can overcome human limitations affecting medical image interpretation, allowing physicians to focus more on analytical interpretation tasks.

This section introduces several distinctive characteristics of medical images, pressing clinical needs for imaging technologies, and existing medical applications.

Characteristics of medical images: Medical images possess particular characteristics compared with natural images, providing unique opportunities for the application of computer-aided techniques to assist in medical diagnosis. Such particular characteristics provide the basis for imaging research advances that have subsequently been translated into clinically usable products.

Below, some of the most distinguished imaging characteristics are summarized and then it is discussed how they are exploited in the context of the described embodiments so as to advance computer-aided diagnosis in medical imaging.

1. Medical images are created by modalities. Natural images typically consist of 3-channel (Red, Green, and Blue) images that exist in the visible light spectrum, whereas various modalities are used to create medical images, including computed tomography (CT), magnetic resonance imaging (MRI), positron emission tomography (PET), mammography, ultrasound, radiography, and so on. Each modality uses a portion of the non-visible electromagnetic spectrum (with the exception of ultrasound, which employs sound waves for image creation) to create images for visualizing and identifying certain medical disorders and procedural complications. Certain medical imaging modalities are more conducive for the evaluation of particular disorders than others. For example, abnormalities such as acute active hemorrhage are more readily diagnosable by intravenous contrast-enhanced CT than MRI, whereas small or subtle lesions such as prostate cancer, uterine cancer, and metastases to the bone and brain may be better shown by MRI. Also, although they may often require the use of ionizing radiation or intravenous contrast administration, cross-sectional techniques, such as CT and MRI, are capable of producing images with substantially richer details than radiography (often colloquially referred to as "X-rays").

2. Medical images possess high dimensionality. Cross-sectional imaging techniques, such as CT, MRI, and ultrasound, produce three-dimensional images, and when dynamic imaging is performed, a fourth dimension, specifically time, is then added. While the world within which we exist is obviously three dimensional, human eyesight is essentially a two-dimensional process. Although various reconstruction algorithms essentially "simulate" the 3D world from multiple 2D views, human eyesight nevertheless relies on two-dimensional spatial information processing. When reading a volumetric cross-sectional imaging examination, radiologists must scroll through a stack of images back to mentally "reconstruct" the underlying anatomy in three dimensions. This is extremely difficult, especially when searching for small lesions, which are only seen on a few images within a large volumetric stack of images, and particularly when an abnormality is similar in appearance to normal anatomies, such as a small lung nodule (which can closely resemble normal pulmonary vessels). To avoid overlooking potentially significant abnormalities, radiologists must scrutinize all aspects of each image contained within a large volumetric stack; nevertheless, it has been well-established through eye-tracking perceptual research that even trained observers fail to visually scan all parts of a medical image Conversely, computer algorithms can interpret high-dimensional images the same way as 2D images by directly harnessing spatial and temporal information.

3. Medical images vary in quality. Owing to substantial differences among medical imaging equipment manufacturers as well as variable proprietary hardware and software platforms, medical images may vary in quality and content among various institutions as well as within a given institution. Furthermore, acquisition protocol parameters (of which there are numerous considerations that must be addressed for a given application), frequently vary considerably among institutions, even for a given manufacturer and application. Such variability results in "domain gaps," both in terms of quality and technical display. These domain gaps are regarded as a major obstacle to the development of robust deep learning methods, often referred to as "domain shift" or "distribution drift." For example, CT scans performed using 5 mm slice thickness can handicap a model trained using CT scans performed using a 0.75 mm thickness, resulting in deep learning methods with a limited clinical value. While the domain shift problem can be addressed by a universally applied configuration for acquiring medical images across hospitals, such an appropriate is unlikely to be adopted. Approaches such as semi-supervised learning domain adaptation, and federal learning have been explored to address the "domain shift" problem.

4. Medical images convey physical meaning. The color information in natural images does not usually carry categorical meaning. For instance, a shirt is a shirt no matter what color it is. In contrast, the exact or relative pixel intensity value in a given medical image corresponds to a specific constituent within the human body, particularly for cross-sectional imaging modalities such as CT and MRI. The exemplary CT images were created by directing ionizing radiation through a body part and counting the relative number of photons absorbed by the tissue traversed by the x-ray beam. A greater number of photons absorbed occurs with denser tissue, such as bone, whereas a greater number of photons transmitted (not absorbed and thus reaching the detector) occurs with less dense tissue, such as lung parenchyma. The commonly used scale to represent the relative amount of x-ray photon absorption at CT is the Hounsfield scale and reflects tissue density. By convention, an attenuation coefficient of zero Hounsfield Units (HU) is equivalent to the density of water (1 gm/cm$^3$). Air or gas, as may be encountered within the large airways and bowel, has an attenuation coefficient of −1,000, whereas bone, a very dense structure, has an attenuation coefficient of approximately 1000 HU. Other tissues within the human body have attenuation coefficients within this range. For example, fat has a value between −80 and −30 HU, whereas un-enhanced muscle has an attenuation coefficient ranging between 35 and 55 HU. This ability to directly measure the density of human tissue enables human experts and computer algorithms to identify both normal human anatomy as well as potential abnormalities. More importantly, the semantics embedded in the pixel intensity is a weak annotation that can be harnessed to facilitate the model to learn the appearance of anatomic structures without extensive manual annotation.

5. Medical images encode relative location and orientation. When identifying objects from natural images, their locations are generally not important: For instance, a cat is a cat no matter if it appears in the top left or bottom right of the image. In contrast, in medical imaging, the relative location and orientation of a structure and the intrinsic consistency of anatomical relationships are important characteristics that allow recognition of normal anatomy and pathological conditions. The regular and predictable location of various structures in the human body is a valuable characteristic for training deep learning models. Since medical imaging protocols image patients in fairly consistent and reproducible positions, these methods generate images with great similarity across various equipment manufacturers and facility locations. Therefore, recognizing the stereotypical position and orientation information of human anatomy provides an opportunity to reduce false positive results and improve the accuracy of disease detection and segmentation. Prior techniques have demonstrated the value of this approach by adding location features, modifying objective functions, and constraining coordinates relative to landmarks in images. For instance, employing ultrasound for measurement of carotid arterial intimal-medial thickness for cardiovascular risk stratification, the measurement could be performed at any point long the longitudinal aspect of the vessel, and such variability could adversely affect results and reproducibility. However, it is standard practice to perform this measurement 1 cm beyond a recognizable anatomic landmark, such as the carotid bulb. As a result, the anatomically recognizable carotid bulb provides a contextual constraint for training deep learning methods.

6. Medical images encode both scale and distance. The uncertain distance between camera and object limits precise size measurements in natural images; in contrast, the physical size of a structure is preserved in medical images. Scale is one of the quantitative attributes of standard imaging formats. The size of a pixel in CT, as an example, is often specified in the DICOM header. By obtaining the number of pixels belonging to an object and the pixel scale from the header, the physical scale and distance between normal structures and lesions in the image can easily be computed. This information is a critical feature in the assessment of disease, both by human interpretation and computer-aided diagnosis because the physical size of a lesion influences disease stage, treatment options, and prognosis. Moreover, the lesion size distribution can serve as a statistic to estimate the domain gaps among datasets collected from different equipment manufacturers, facilities, and regions, allowing the creation of more robust models and enhancing the ability to extrapolate computer-aided diagnoses across various medical practices.

7. Medical images have sparse and noisy labels. Unlike natural imaging datasets, it is impractical to annotate millions of medical images with a systematic label hierarchy. Most publicly available medical imaging datasets focus on particular anatomic regions and only provide annotation for the object of interest. For example, the KiTS dataset provides annotation only for the kidney, the LiTS dataset for the liver, and the NIH Pancreas-CT dataset for the pancreas. There is no dataset that provides systematic annotation for all visible structures in a medical imaging dataset; existing annotated datasets are either only partially annotated or only labeled on a small scale. Organizing a hierarchical labeling dictionary to address various organs, tissues, and diseases, as well as reflect their spatial relationships in the human body, remains a large limitation for deep learning methods. Moreover, the available annotated images are often associated with noise due to inter-observer and intra-observer variability. Stated differently, different human experts may provide conflicting opinions regarding a given lesion, reflecting inter-observer variability; furthermore, the same expert is likely to produce very different lesion contours over multiple attempts separated in time, reflecting intra-observer variability. Additionally, more severely noisy labels occur if the abnormality has indistinct boundaries, such as diffuse lung diseases. The partial and imperfect annotation compromises model training and results in ambiguous and unreliable results when deep learning methods undergo testing.

In summary, medical images contain quantitative imaging characteristics, such as the intensity value and physical size of pixels, that can be used as additional information to enhance deep learning performance. Medical images also present qualitative imaging characteristics, such as consistent and predictable anatomical structures with great dimensional details, that can provide an opportunity for comprehensive model training. Nevertheless, several characteristics unique to medical images create unmet challenges, such as isolated, discrepant data and partial, noisy labels that must be addressed through additional investigation.

Clinical needs: Computer-aided diagnosis holds a long history, which has been focusing on a key promise; specifically, that CAD systems are not developed to replace physicians but rather to enhance their capabilities through computer-physician synergy. With deep learning methods elevating numerous CAD systems to a human-level precision, the number of clinical needs has been rapidly increasing in recent decades.

The following terms are utilized herein:

Medical image classification refers to classifying what type of lesion is contained in an image. Such classification may be binary (e.g., benign or malignant) or multi-class (various types of lesions). The annotation for classification tasks is to assign one or a few labels to an image or a study.

Disease localization and detection refer to identifying the location of specific lesions. Their difference is subtle: localization aims to locate a single lesion, while detection aims to find all lesions in the image. The annotation for detection and localization provides both the specific location and the scale of the disease with a bounding box.

Medical image segmentation refers to creating a pixel-wise mask of the organ/lesion in the image. Segmentation can ease the analysis by measuring more accurate and desirable imaging biomarkers. The annotation for segmentation tasks is to assign every pixel in an image to at least one class.

Medical image registration refers to aligning the spatial coordinates of one or more images into a standard coordinate system. Image registration plays an important role in disease prognosis by establishing correspondence among multiple scans taken from different time points.

Medical image reconstruction refers to forming a high-quality image from raw data obtained by medical imaging devices, such as CT or MRI scanners.

Medical image enhancement refers to adjusting the intensity of an image for better visualization or further analysis. Such enhancement includes de-noising, super-resolution, artifact removal, MR bias field correction, and image harmonization. Other tasks include landmark detection, image or view recognition, automatic report generation, etc.

The main focus here are specifically the tasks of image classification and segmentation, with some other tasks such as disease detection and CIMT thickness measurement. The goal is to minimize the annotation cost associated with these tasks while maintaining comparable or even higher performance.

For instance, consider the simplified workflow depicted at FIG. 2A, which illustrates how deep learning engages with health care applications in practice, including aim 1 (element 201) which is to obtain annotation from a human expert, aim 2 (element 202) which is to train a deep model using these human annotations, and aim 3 (element 203) which is to deploy the deep model in clinical practice, perhaps to the hospital having a lack of experts. To optimize this workflow and to quickly build an effective system, the research goal is optimized with novel methods to minimize the manual labeling efforts. For instance, with respect to aim 1 (element 201), the objective is therefore to minimize manual annotations efforts for rapid, precise, computer-aided diagnosis systems supported by the acquisition of those images that are considered necessary for image annotation. With respect to aim 2 (element 202), the objective is therefore to utilize existing annotation effectively from advanced architectures through the development of deep neural network architectures with existing annotation capabilities. With respect to aim 3 (element 203), the objective is therefore to extract generic knowledge directly from un-annotated images using feature learning and transfer learning to generate a trained model which may then be applied to medical healthcare applications.

Figure 2E:
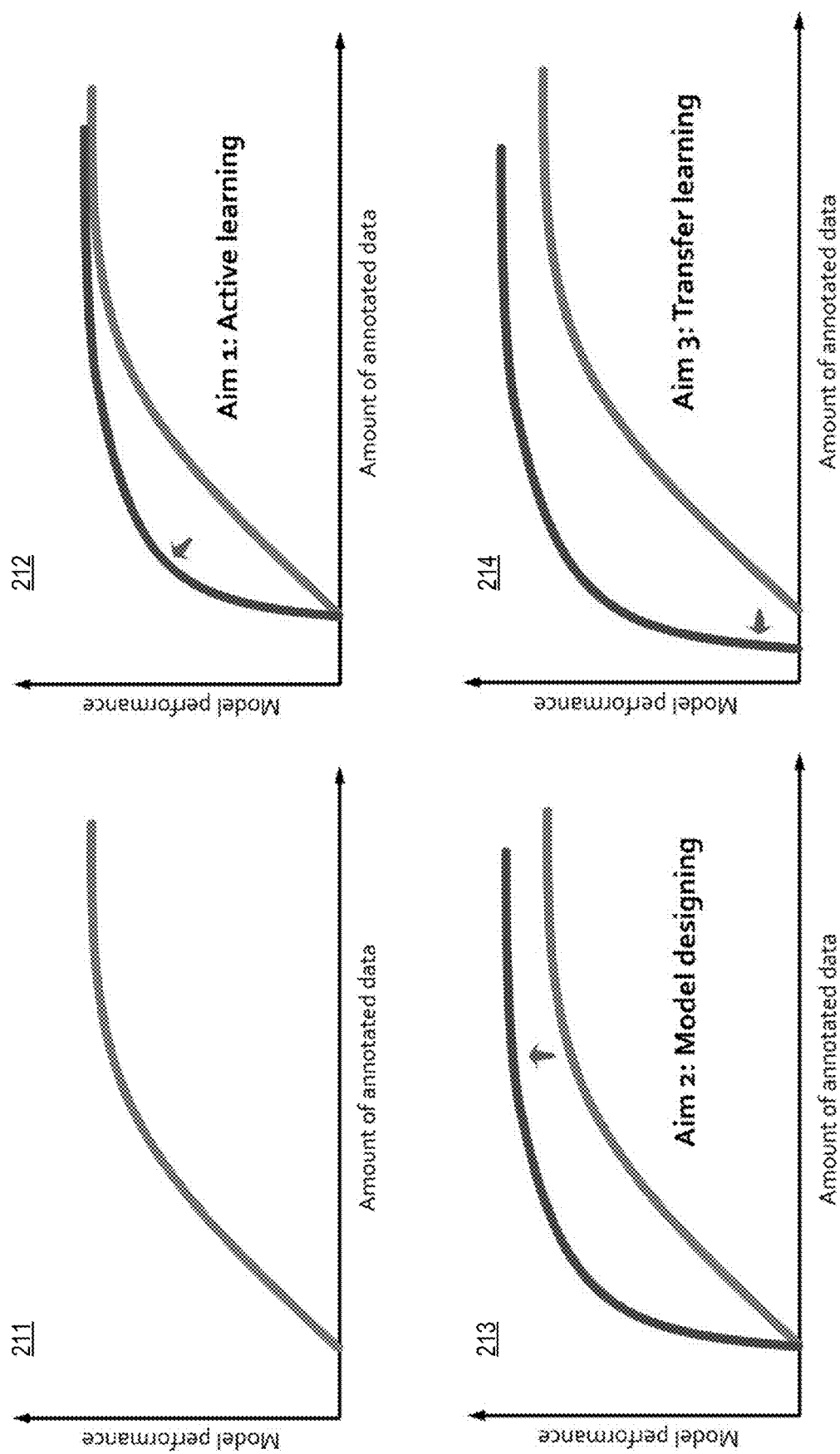
FIGS. 2E and 2F illustrate the impact on model performance through the use of various training methodologies, in accordance with disclosed embodiments.
Figure 2F:
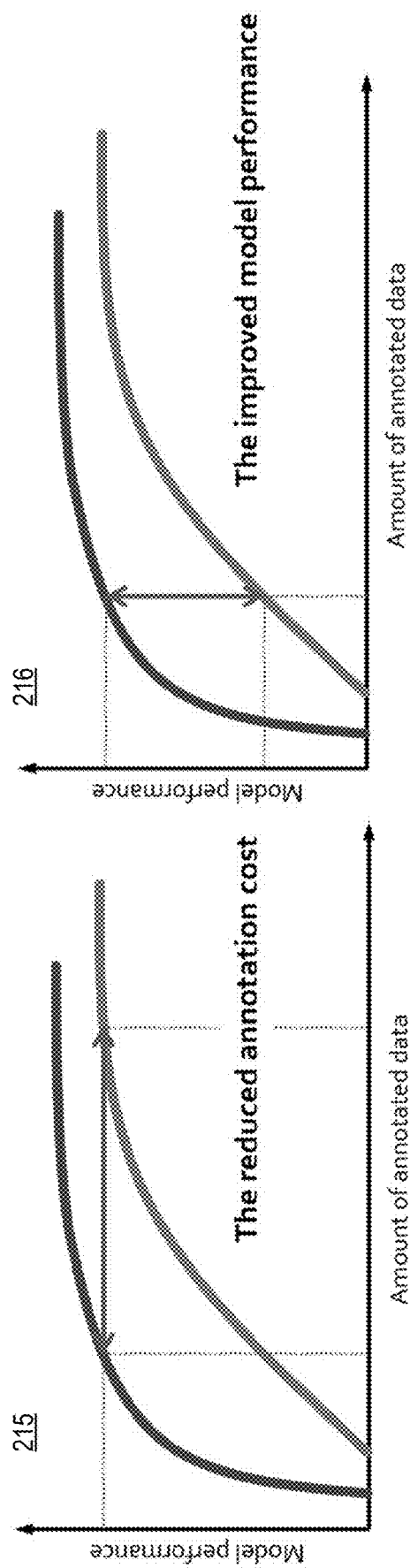

FIGS. 2E and 2F illustrate the impact on model performance through the use of various training methodologies.

Graphs 211 and 212 at FIG. 2E show that with a small part of the dataset annotated, the deep models training techniques described herein can deliver results that approximate or even outperform models requiring annotating an entire dataset. Graph 212 shows the resulting increase in model effectiveness through the use of active learning (e.g., aim 1 at element 201). Graph 213 shows the resulting increase in model effectiveness through the use of improved model design (e.g., aim 2 at element 202). Graph 214 shows the decreased reliance upon annotated data for an effective model through the use of transfer learning (e.g., aim 3 at element 203).

Graph 215 at FIG. 2F shows the resulting reduction in annotation cost and graph 216 illustrates the consequential improvement in model performance above prior known techniques.

Figure 2G:
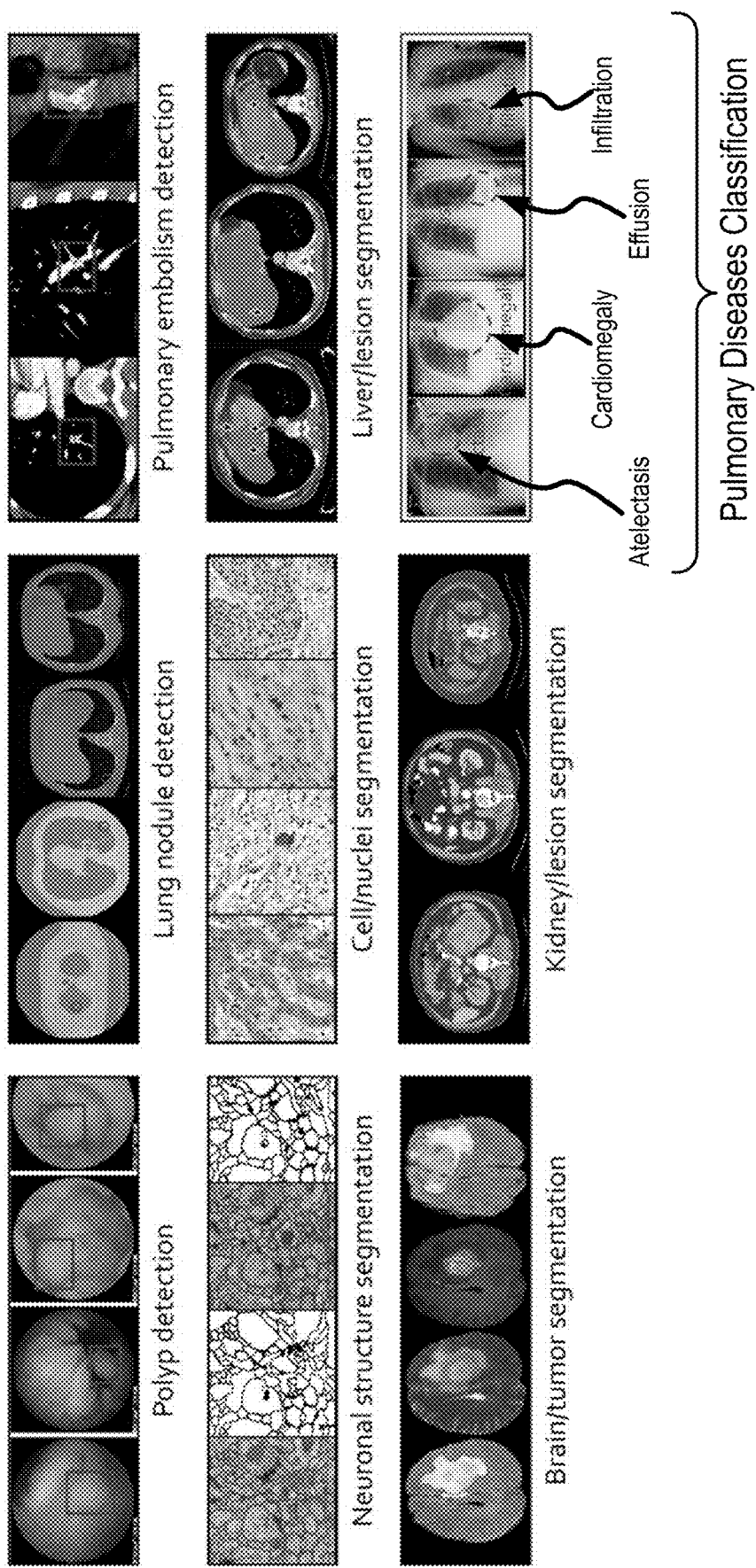
FIG. 2G provides additional examples of detection, segmentation, and classification across nine different medical applications, in accordance with described embodiments.

FIG. 2G provides additional examples of detection, segmentation, and classification across nine different medical applications, in accordance with described embodiments. As shown here, in order to validate the three aims described above, nine different use-cases are evaluated including polyp detection, lung nodule detection, pulmonary embolism detection, neuronal structure segmentation, cell/nuclei segmentation, liver/lesion segmentation, brain/tumor segmentation, kidney/lesion segmentation, and pulmonary diseases classification.

Figure 2H:
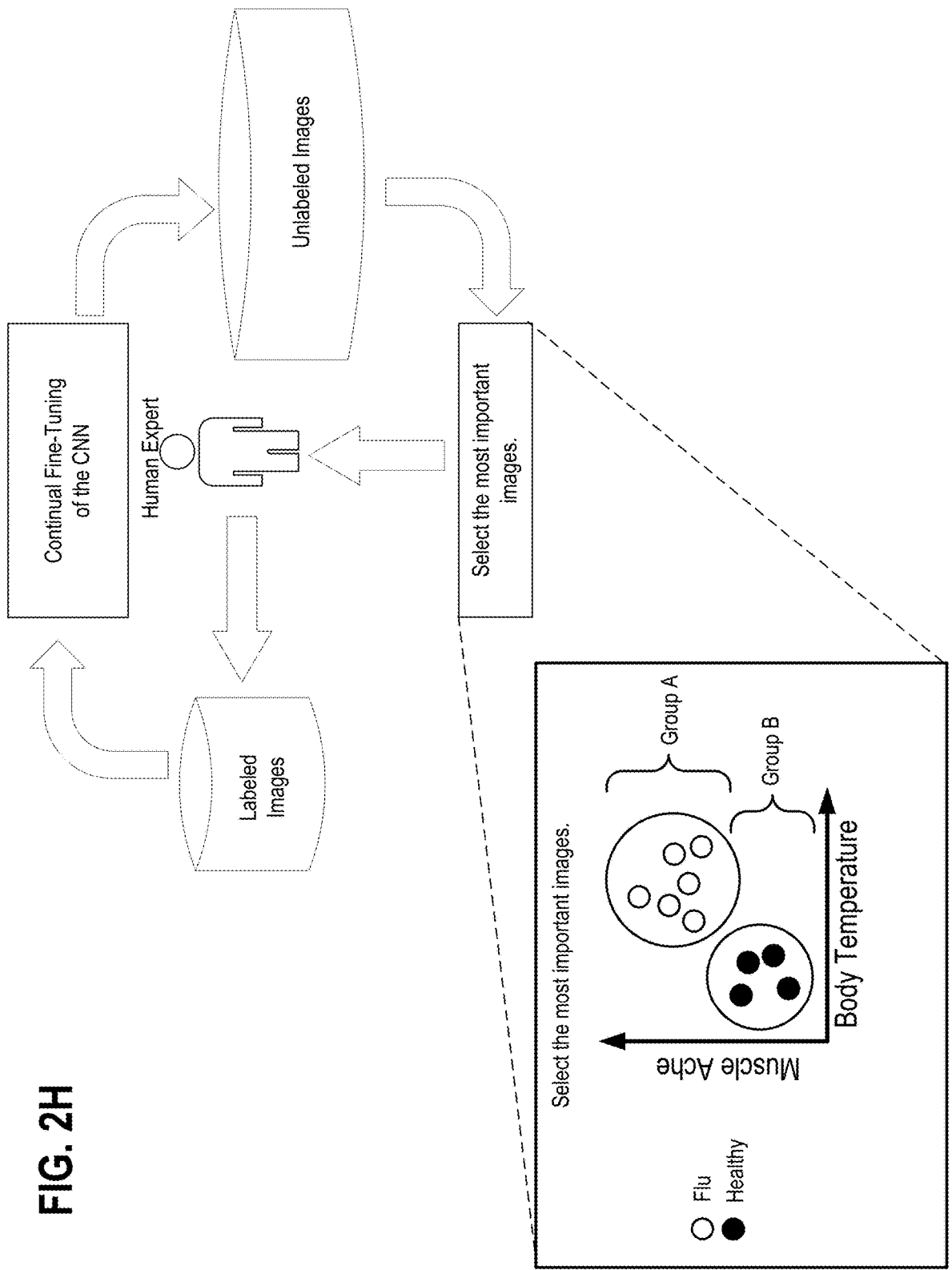
FIGS. 2H, 2I, and 2J provide examples of the "human-in-the-loop" active learning procedure supplemented by data augmentation techniques, in accordance with disclosed embodiments.
Figure 2I:
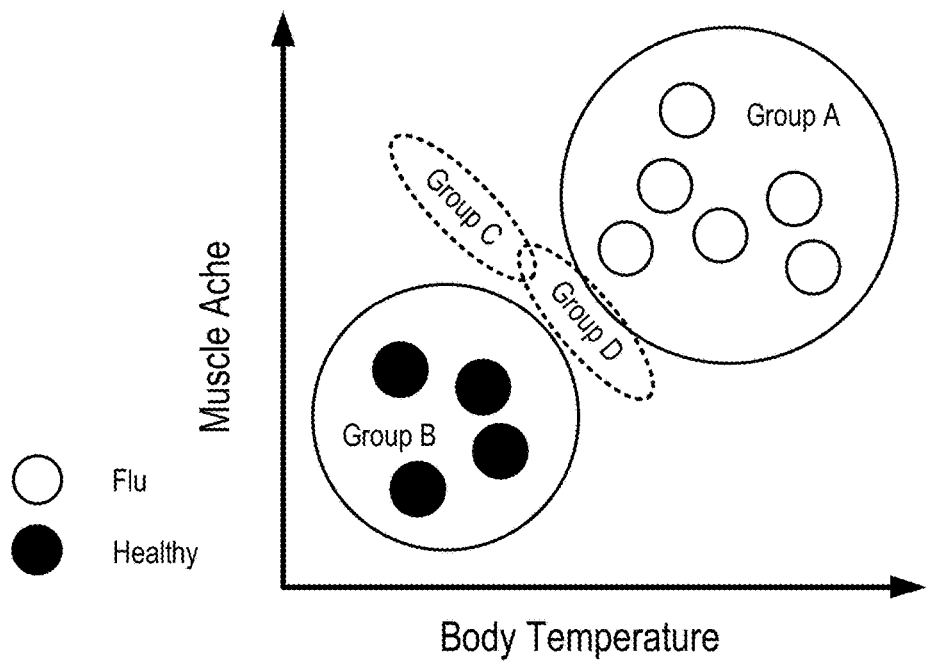
Figure 2I:
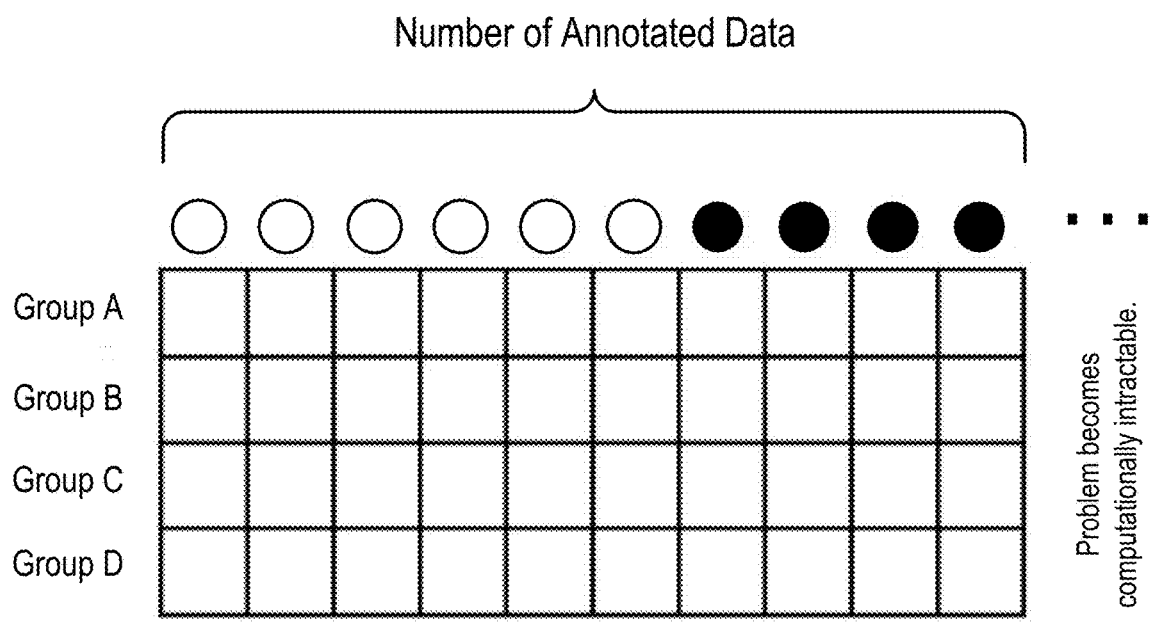

FIGS. 2H and 2I provide examples of the "human-in-the-loop" active learning procedure supplemented by data augmentation techniques. As shown here, the technique incorporates both human experts and the deep model together to precisely detect the disease. Using the labeled images, the deep model is fine-tuned repeatedly, resulting in predictions from the new model. With the aid of human experts, the most important images are selected again for annotation, resulting in the iterative loop. The challenge remains, however, how to select the most important images. For instance, given two symptoms, such as the common flu versus Covid-19, and assuming limited budget, time resource, and trained experts, which should be annotated first? If group A (the flu) it can already be classified into the positive group by the current model. However, subject B is more ambiguous to the current model. Whether it is positive or negative will dramatically change the boundary decision.

For instance, as depicted here, two major symptoms from Covid-19 are adopted and classified into positive and negative groups, each being an un-labeled subject. Subject A (the flu) exhibits low entropy (low uncertainty) whereas subject B (healthy) exhibits high entropy (high uncertainty).

A limiting factor for active learning procedures is that each iteration may only suggest one important feature, such as a lesion, each iteration, and thus, if a single patient contains multiple lesions, then the active learning procedure might suggest to annotate the same patient multiple times, and each time on a different lesion. Consequently, a human expert must therefore repeat going through the same patient multiple times. To overcome this limitation, certain embodiments transition from lesion-level annotation to patient level annotation, such that doctors no longer must repeat going through the same patient multiple times to detect all diseases that any given patient may have. Rather, the doctor need only go through each single patient a single time and may annotate all disease present simultaneously.

As depicted at FIG. 21, there are boundary conditions formed resulting in the creation of groups C and D, each having low diversity, and no matter the number of annotated data present, the problem becomes computationally intractable.

Figure 2J:
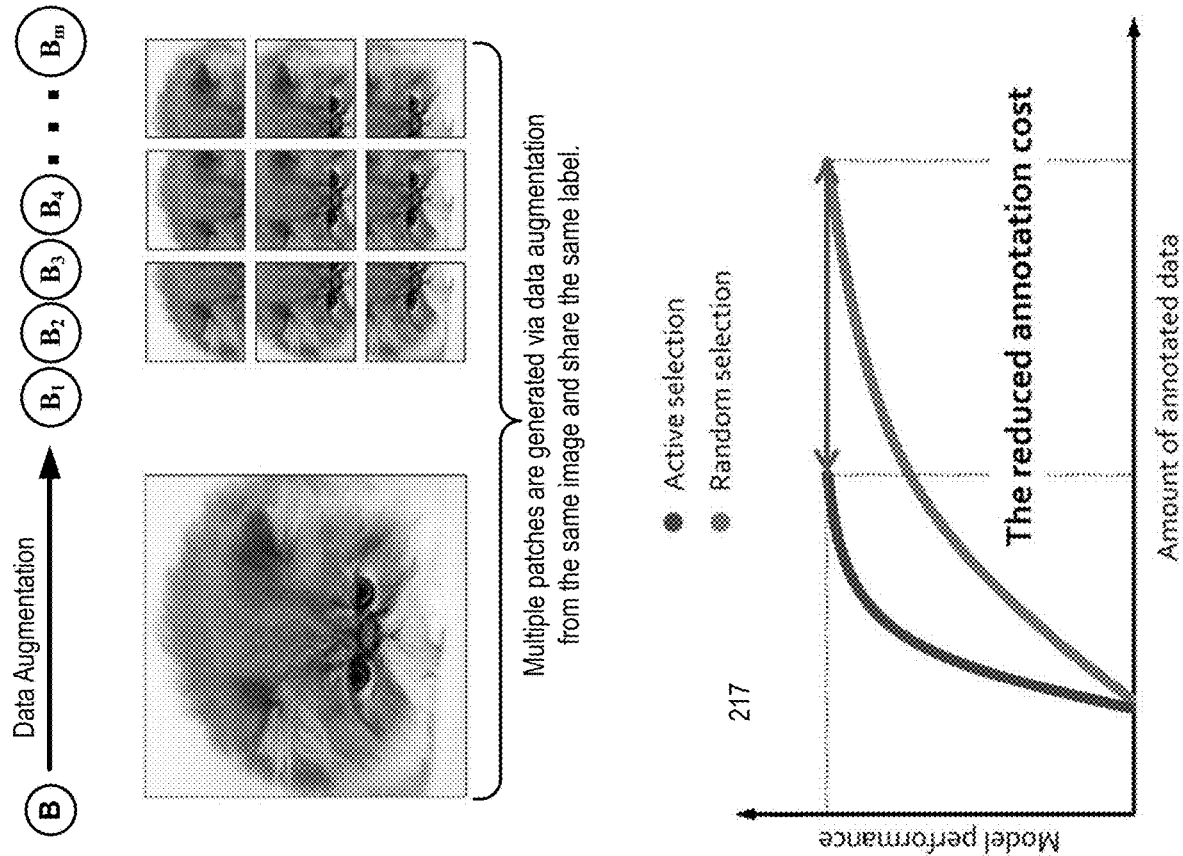
Figure 2J:
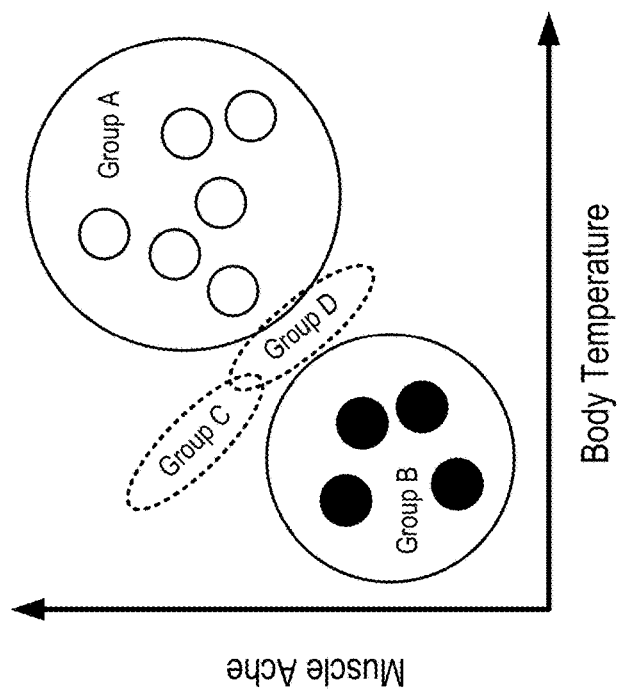

Data augmentation is utilized to train the CNNs, in which multiple patches are generated from the same image and share the same label. Each of the patches are expected to have similar predications by the current CNN. As depicted by graph 217 at FIG. 2J (similar to graph 215 at FIG. 2F), the gap represents the amount of annotation cost that has been reduced. This is because wisely selecting the most important samples operates to dramatically reduce annotation costs.

Figure 2K:
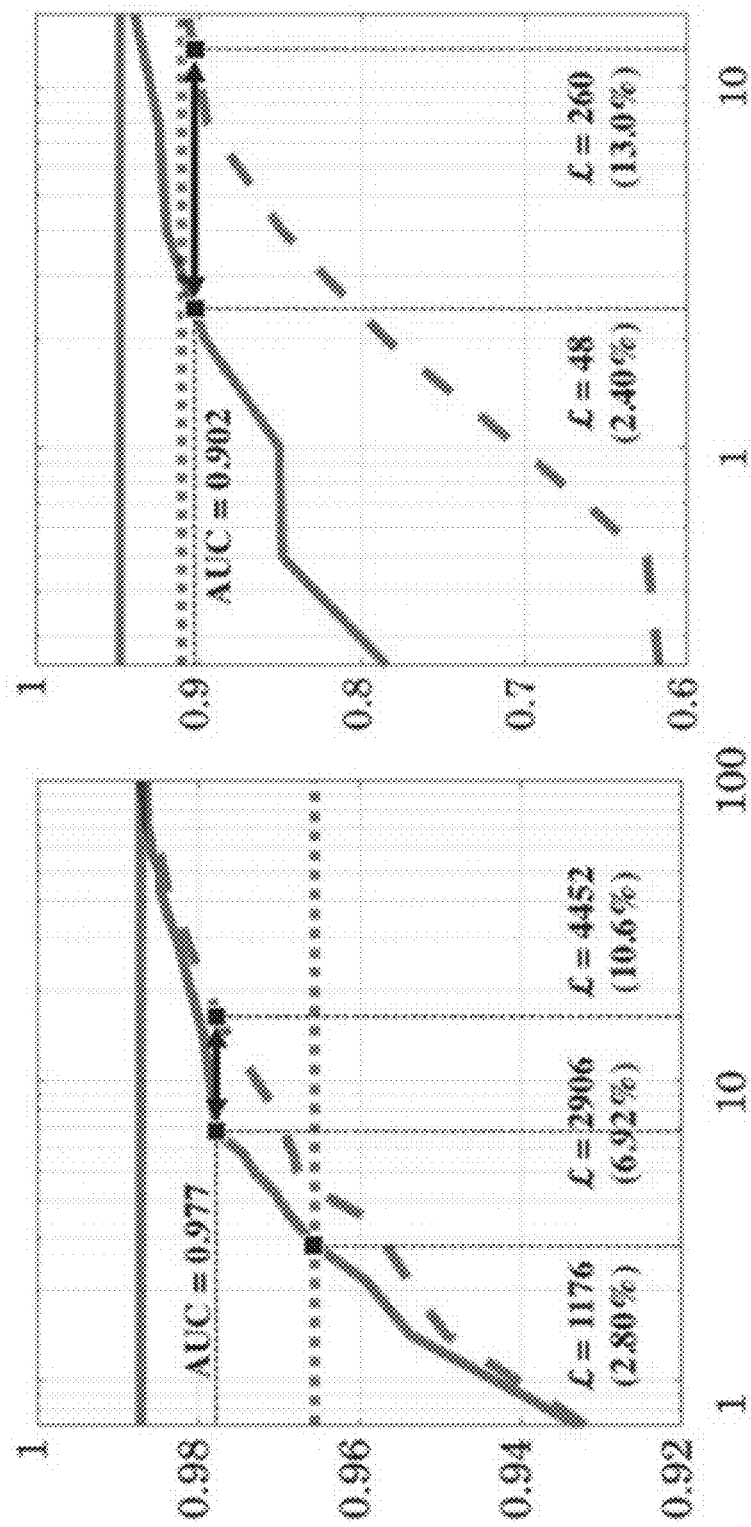
FIGS. 2K and 2L illustrate a reduction of annotation cost by greater than 60% when compared with random selection, in accordance with disclosed embodiments.
Figure 2L:
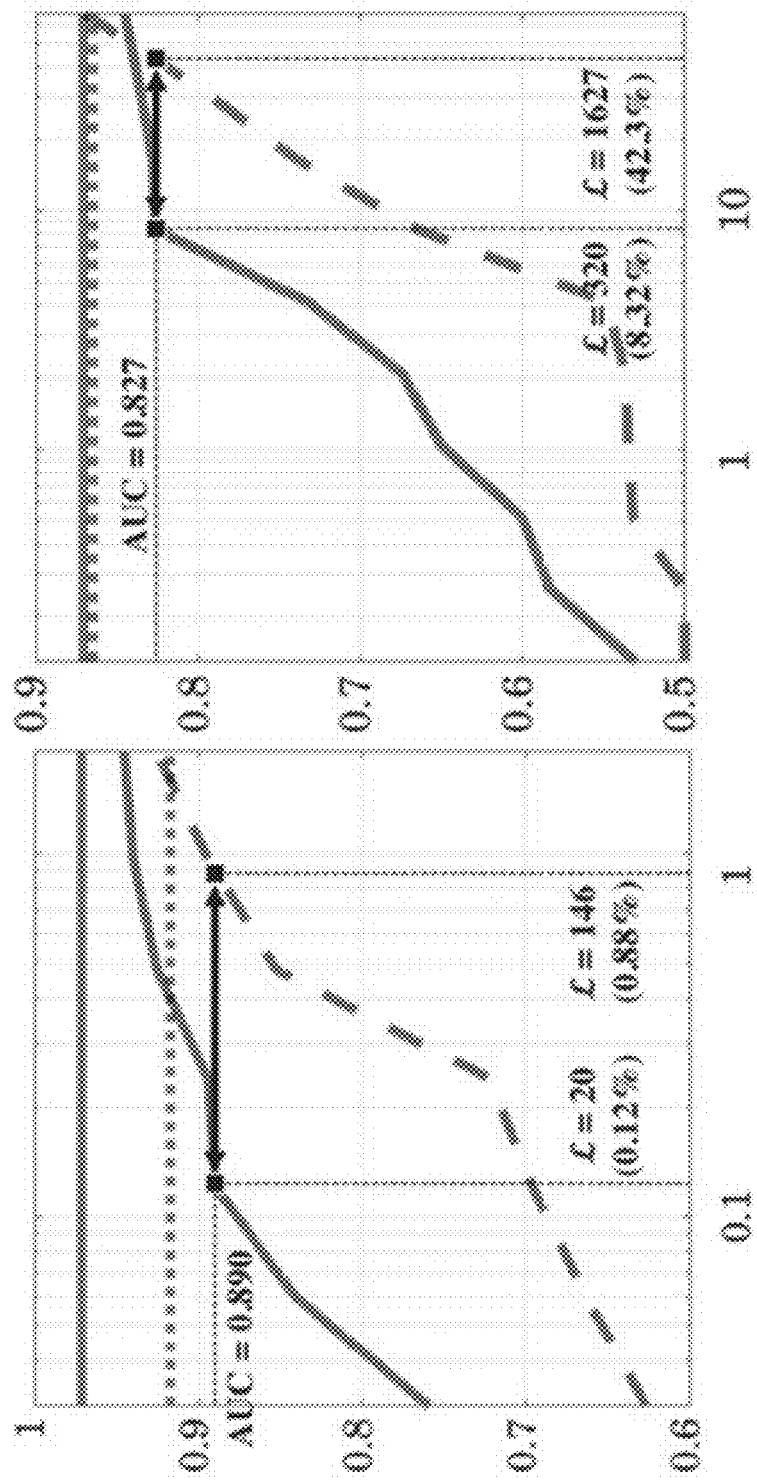

FIGS. 2K and 21L provide illustrate a reduction of annotation cost by greater than 60% when compared with random selection.

It may therefore be concluded that not all data is created equal, and thus, one important objective is to find the most essential data that effectively increases the performance of a trained deep model with as low as annotation cost as possible.

Thus, the clinical impacts of aim 1 (element 201) may be considered to be the continual learning capability of deep models which encourage data, label, and model re-use; an efficient "human-in-the-loop" procedure which assists radiologist in quickly dismissing patients with negative results, therefore dramatically reducing the burden of annotation; and an instance on-line feedback process which makes it possible for CAD systems to be self-learning and self-improving via a continual fine-tuning feedback system.

Figure 3A:
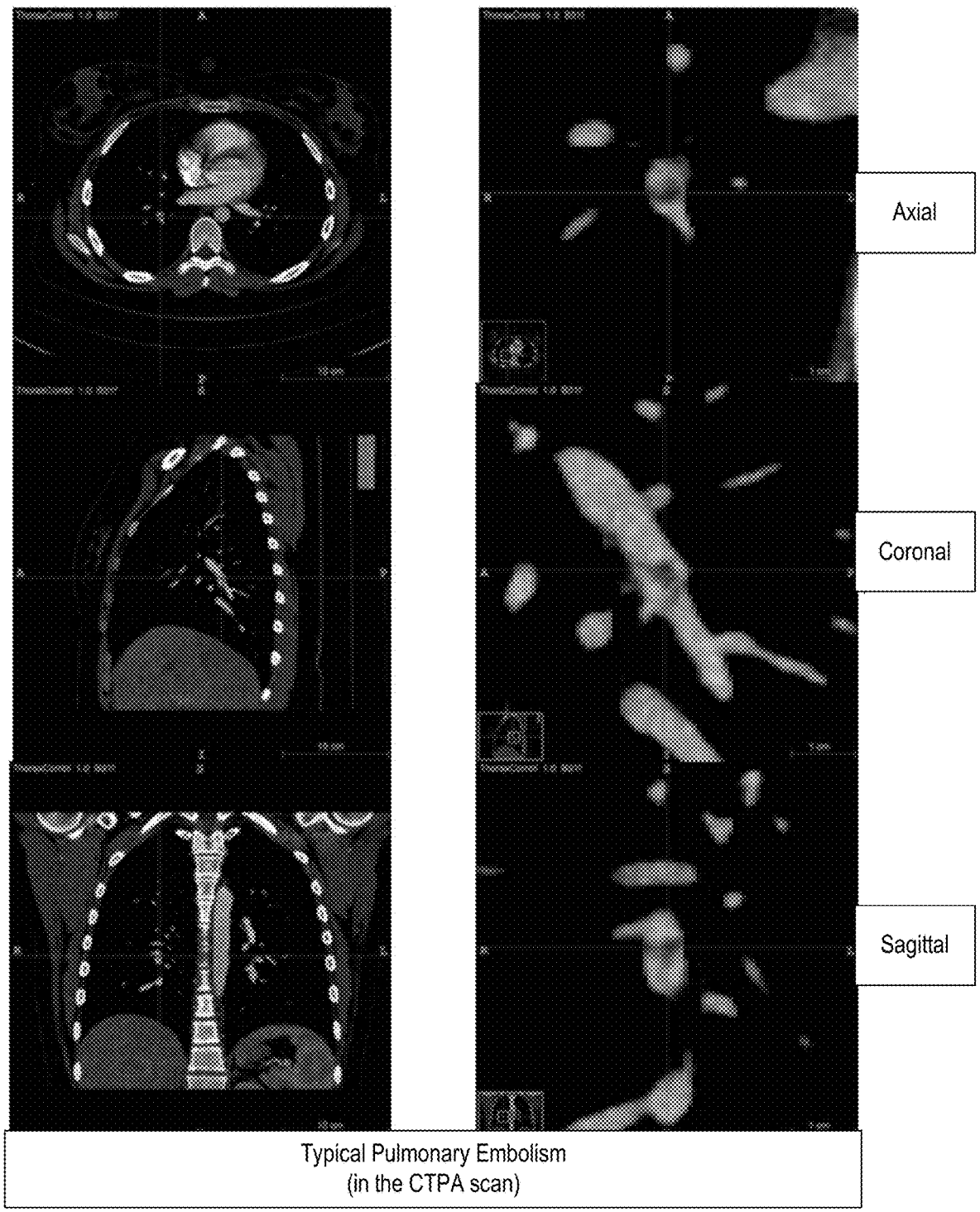
FIG. 3A depicts the typical appearance of pulmonary embolism in the CTPA scan, presented from an axial, coronal, and sagittal views, in accordance with disclosed embodiments.

FIG. 3A depicts the typical appearance of pulmonary embolism in the CTPA scan, presented from an axial, coronal, and sagittal views.

Figure 3B:
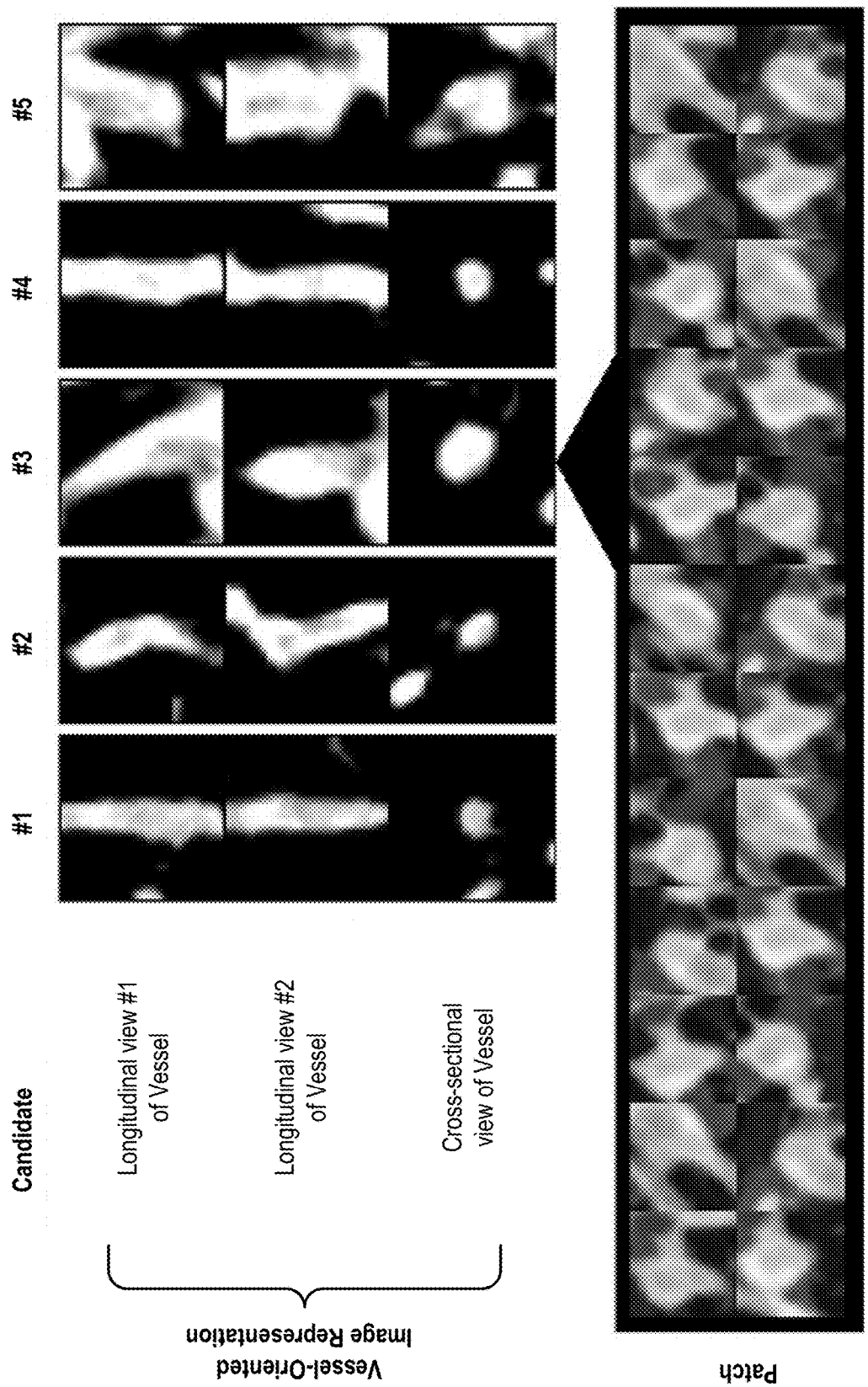
FIG. 3B depicts five different pulmonary embolism candidates in the vessel-oriented image representation, in accordance with disclosed embodiments.

FIG. 3B depicts five different pulmonary embolism candidates in the vessel-oriented image representation.

The CTPA scan of pulmonary embolism candidates were adopted because it achieves great classification accuracy and accelerates CNN training convergence.

Medical application—Case Study of PE CAD: Interest in implementing deep learning methods in computer-aided diagnosis systems has increased tremendously in the past decade due to the promising or even super-human, performance for various medical applications.

This section provides a case study for conducting a medical application that involves deep learning, from curating the structure of data and annotation, to developing the system and validating the performance. Specifically demonstrated is the annotation-efficiency of the described techniques in several key facets of the CAD system in practice. In particular, a step-by-step workflow illustrates use of the application for detecting pulmonary embolism from CTPA images. The idea of implementing deep learning methods into computer-aided diagnosis systems can be adapted to many other medical applications that require automated medical image analysis.

Pulmonary embolism: Pulmonary Embolism (PE) is a major national health problem, which is responsible for approximately 100,000-200,000 deaths annually in the United State alone, representing the third most common cause of cardiovascular death after myocardial infarction and stroke. A Pulmonary Embolism is a condition in which a thrombus (often colloquially referred to as a "blood clot" travels to the lungs, often from a lower extremity venous source, producing a blockage of the pulmonary arteries within the lungs. The mortality rate of untreated PE may approach 30% but it decreases to as low as 2% with early diagnosis and appropriate treatment CT pulmonary angiography (CTPA) is the primary means for PE diagnosis, in which a radiologist carefully traces each branch of the pulmonary artery for any suspected PEs. With the aid of the CTPA scan, PEs appear as "filling defects" within enhanced pulmonary arteries following the administration of intravenous contrast, as shown at FIG. 3A.

Unfortunately, CTPA interpretation is a time-consuming task, of which accuracy depends on human factors, such as attention span and sensitivity to the visual characteristics of PEs. Computer-aided PE detection can have a major role in improving the diagnostic capability of radiologists and decreasing the reading time of CTPA scans.

The described techniques were developed in conjunction with a computer-aided PE detection system by using an in-house dataset from ASU-Mayo which consists of 121 CTPA scans with a total of 326 emboli. The dataset provides the spatial coordinates of each emboli in the scan. The dataset is divided at the patient-level into a training set (71 patients) and a test set (50 patients). To study the robustness and generalizability of the algorithm, the system was also evaluated using 20 CTPA scans from the CAD-PE challenge.

The computer-aided PE detection system as described herein consists of two stages to detect PEs from images: (1) candidate generation and (2) false positive reduction. These two stages have also been widely used in most existing disease detection systems. In the following sections, the methodology and performance for each stage are described in greater detail.

Generating Pulmonary Embolism Candidates: The described methodologies use an unsupervised approach for candidate generation, consisting of heuristic lung segmentation and a tobogganing algorithm. In a chest CTPA scan, lungs appear darker than their surrounding. To segment lungs from the scan, processing first clips voxel intensity values using a threshold of −400, resulting in a binary volume wherein the lungs and other dark regions appear white. Then, a closing operation is performed to fill all dark holes in the white area.

To exclude non-lung areas, a 3D connected component analysis is performed and further processing removes the components with small volumes or a large length ratio between the major and minor axes. The purpose of segmenting the lungs is to reduce the computational time and the number of false positives for the toboggan algorithm. Since peripheral PEs only appear in pulmonary arteries, there is no need to search for PE candidates outside the lungs. The tobogganing algorithm is then applied only to the lung area, generating the PE candidate coordinates that are then used to crop sub-volumes from the CTPA scan.

This procedure of candidate generation is directly applied to an available PE candidate generator to produce the dataset, resulting in a total of 8,585 PE candidates, in which 863 were true positives and 7,722 were false positives. There are 326 unique emboli annotated in the dataset utilized. Since multiple detections can be generated from a large PE the number of true positives is greater than the number of unique emboli. Analysis from prior techniques results in a sensitivity of 93% with, on average, 65.8 false positives per patient for the entire candidate generation stage.

Reducing Pulmonary Embolism false positives: The previous stage generates coordinates that indicate where the PE candidate is located. Processing crops sub-volumes based on the location, so that the PE candidate will appear in the center of each sub-volume. The sub-volume has a physical size of 20×20×20 mm and then resized into 64×64×64 pixel.

To conduct a fair comparison with the prior studies candidate-level AUC (Area Under the ROC Curve) is computed for classifying true positives and false positives. Therefore, the disclosed methodology advances techniques previously utilized and yields significant performance gains in three aspects (see Table 5.1 as presented at FIG. 1D).

1. Extending VOIR into the 3D version. In general, emboli can affect pulmonary arteries in any orientation, exhibiting a significant variation in PE appearance (see FIG. 3A). This complicates the classification task and hinders the effective utilization of deep learning methods. To implement vessel alignment, principal component analysis (PCA) is first applied to voxel intensities for estimating the vessel's orientation. Scan planes are then rotated into alignment with the vessel longitudinal axis, resulting in images with standardized appearance, wherein emboli consistently appear as elongated structures in the longitudinal vessel view and as circular structures in the cross-sectional view (refer to FIG. 3B). This interpolation scheme guided by the vessel axis has the effect of maximally revealing the filling defects thereby facilitating PE diagnosis for both radiologists and computers. Note that VOIR is implemented in both 2D and 3D, demonstrating that the vessel-oriented image representation exceeds the regular image representation.

2. Utilizing three-dimensional models and data. While adopting 3D models to process 3D volumetric data may appear to be a natural choice, it occurs a substantial computational cost, lack of sufficient data, and risk of overfitting. As a result, several alternative strategies were proposed to reformat 3D applications into 2D problems. For instance, formulated regular 2D inputs by extracting adjacent axial slices (refer to as 2D slice-based input). A more advanced strategy is to extract axial, coronal, and sagittal slices from volumetric data (referred to as 2.5D orthogonal input). These reformatted 2D solutions can generate large number of data and benefit from 2D pre-trained ImageNet. However, 2D solutions inevitably sacrifice the rich spatial information in 3D volumetric data and large capacity of 3D models. As the computer power increased and pre-trained 3D models developed recent years, the interest is shifting back to 3D techniques, with several emerging evidences indicating that 3D applications are better to be addressed in 3D. The experimental results provided here also suggest that, with the same initialization and vessel orientation, 3D volume-based inputs offer higher performance than 2.5D orthogonal inputs, which in turn work better than 2D slice-based inputs.

3. Initializing models with Models Genesis. Training a deep model from scratch is difficult because it requires a large amount of labeled training data and a great deal of expertise to ensure proper convergence. Fine-tuning Models ImageNet has become the most practical adoption for deep learning applications in medical imaging to ease the training procedure On the other hand, Models ImageNet may give suboptimal initialization in the medical imaging domain as they were pre-trained from only natural images; it is associated with a large domain gap for medical images. Models Genesis is pre-trained in the same domain to reduce this domain gap. The Models Genesis 2D utilized here offers similar performance to Models ImageNet. This result is encouraging because the Models Genesis 2D was developed without using any manual annotation, while Models ImageNet requires more than fourteen million annotated images. More importantly, Models ImageNet only provide 2D models, which cannot handle 3D data directly, while Models Genesis can be pre-trained in both 2D and 3D manner. The results provided show that Models Genesis secure great performance gain (10% improvement without VOIR and 4% with VOIR) in comparison with Models ImageNet. It may therefore be concluded that Models Genesis consistently outperform models learning from scratch and achieve the best performance when using 3D VOIR sub-volumes as input.

Figure 3C:
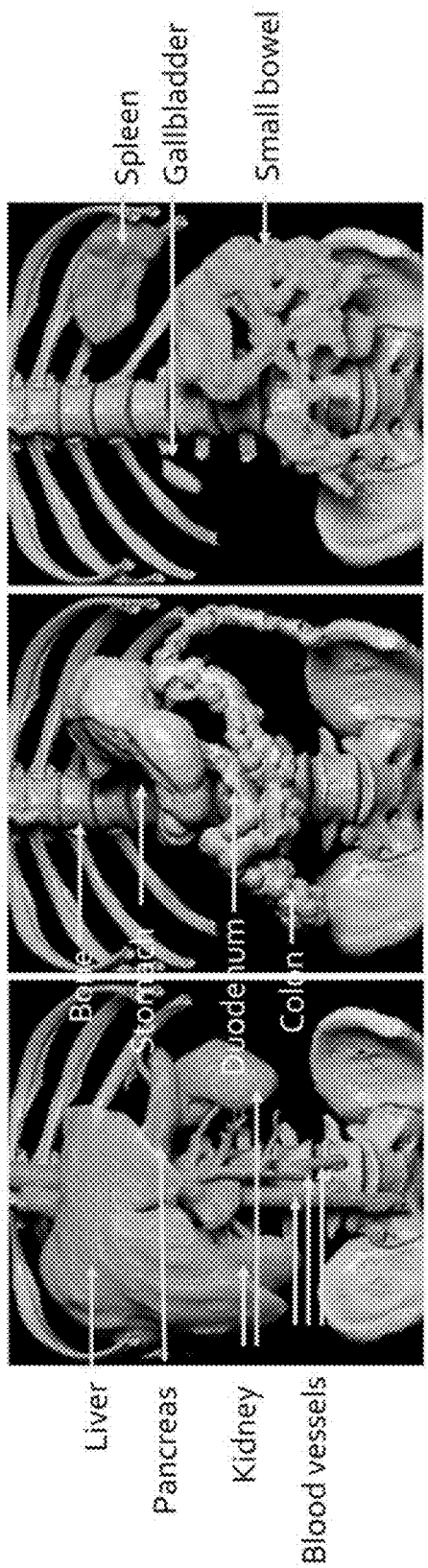
FIG. 3C illustrates the use of segmentation to partition an image into multiple segments to ease analysis of the trained deep model, in accordance with disclosed embodiments.
Figure 3C:
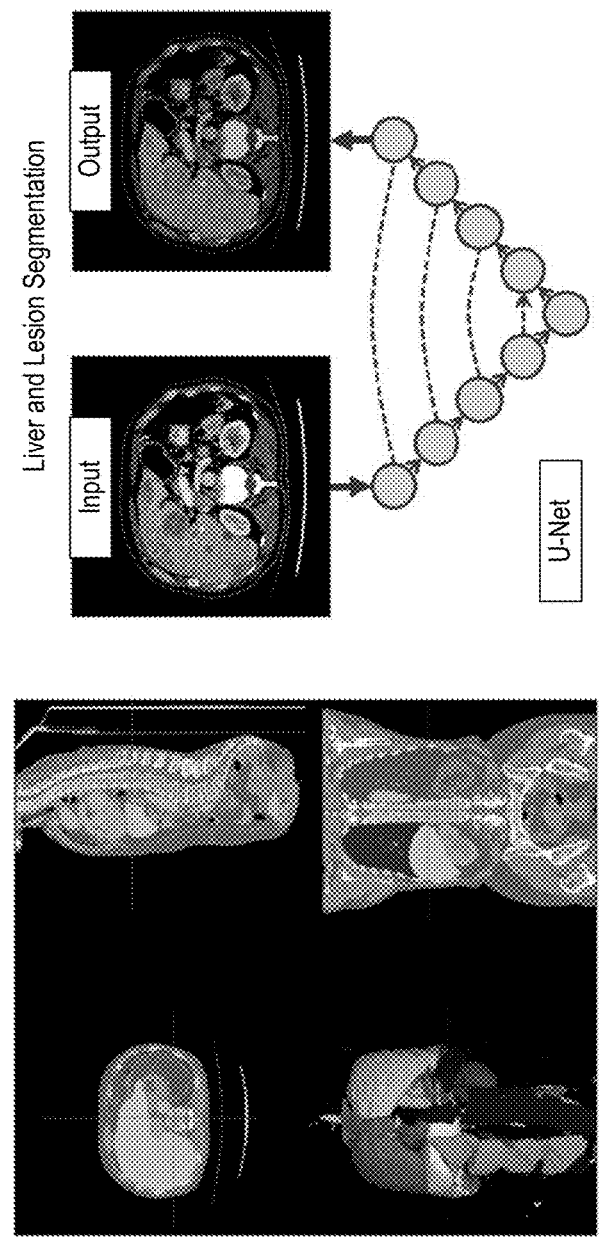

FIG. 3C illustrates the use of segmentation to partition an image into multiple segments to ease analysis of the trained deep model. The most popular architecture for image segmentation is the U-Net, named so because it has a shape that looks like a large "U." The input is the medical image and the output is the segmentation mask of the garget object. The encoder of the U-Net maps from image space to deep latent features and the decoder maps the latent features back into the segmentation mask. As shown here, the model operates to extract different level of image features. By aggregating multi-scale features it is possible to yield a powerful model for image segmentation, which considers not only level 4 features, but also considers level 3, 2, and 1 image features.

Figure 3D:
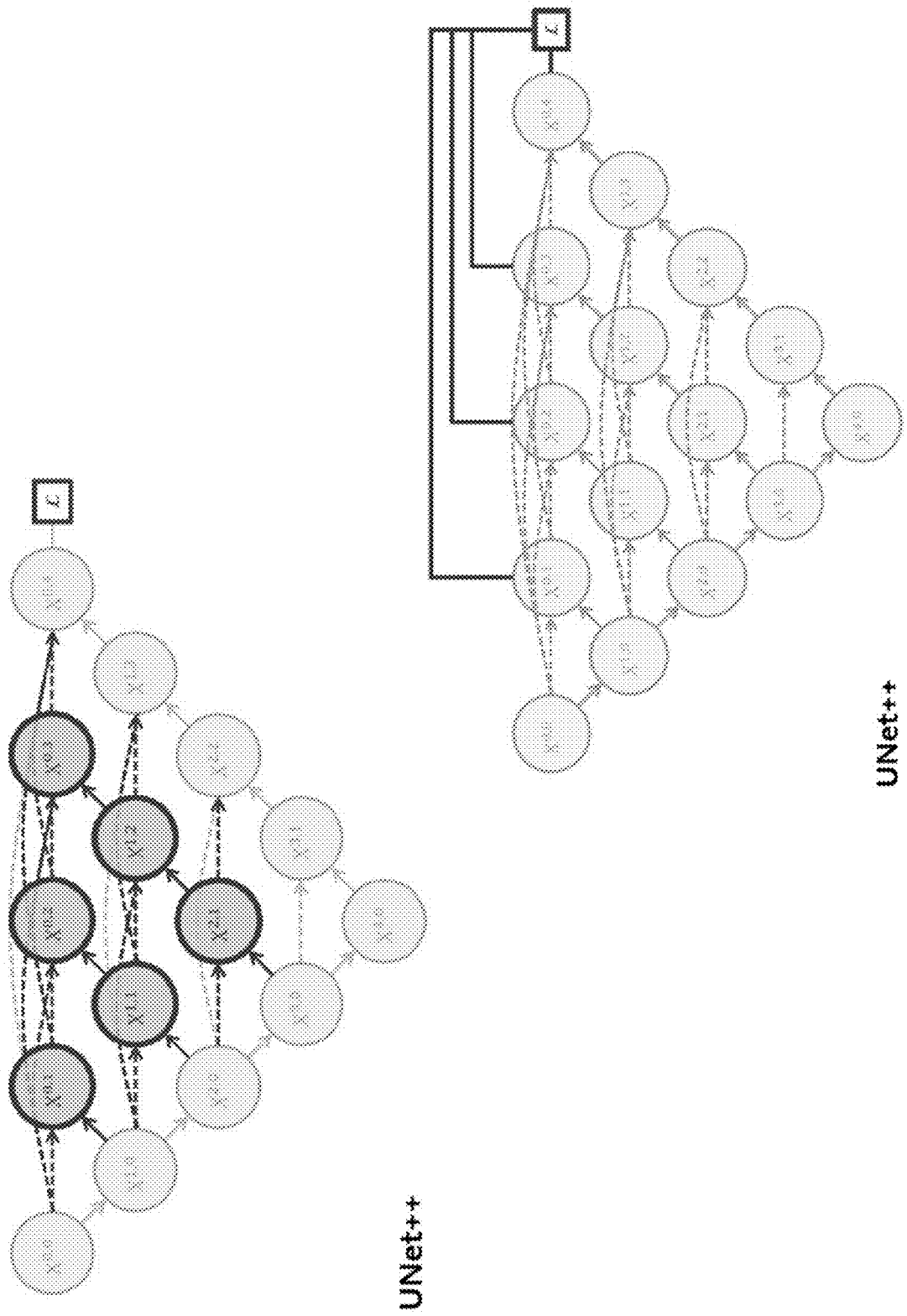

FIGS. 3D and 3E illustrate the use of a UNet++ model for improved segmentation accuracy. As shown here, through the redesign of skip connections, it is possible to aggregate multi-scale features. The depicted UNet++ provides an advanced and improved architecture over the original U-Net model, referred to as UNet++ because it provides two notable innovations. Firstly, the skip connections are redesigned so as to encourage different levels of image feature aggregation and secondly, to introduce deep supervision into the model. This is in contrast with the original U-Net architecture, in which the UNet++ provides additional supervision for every level of image features so as to achieve higher segmentation accuracy. With reference to FIG. 3E, it may be observed that each node is independent from the remaining parts of the model during the testing phase, and yet, contributes during the training phase.

Figure 3F:
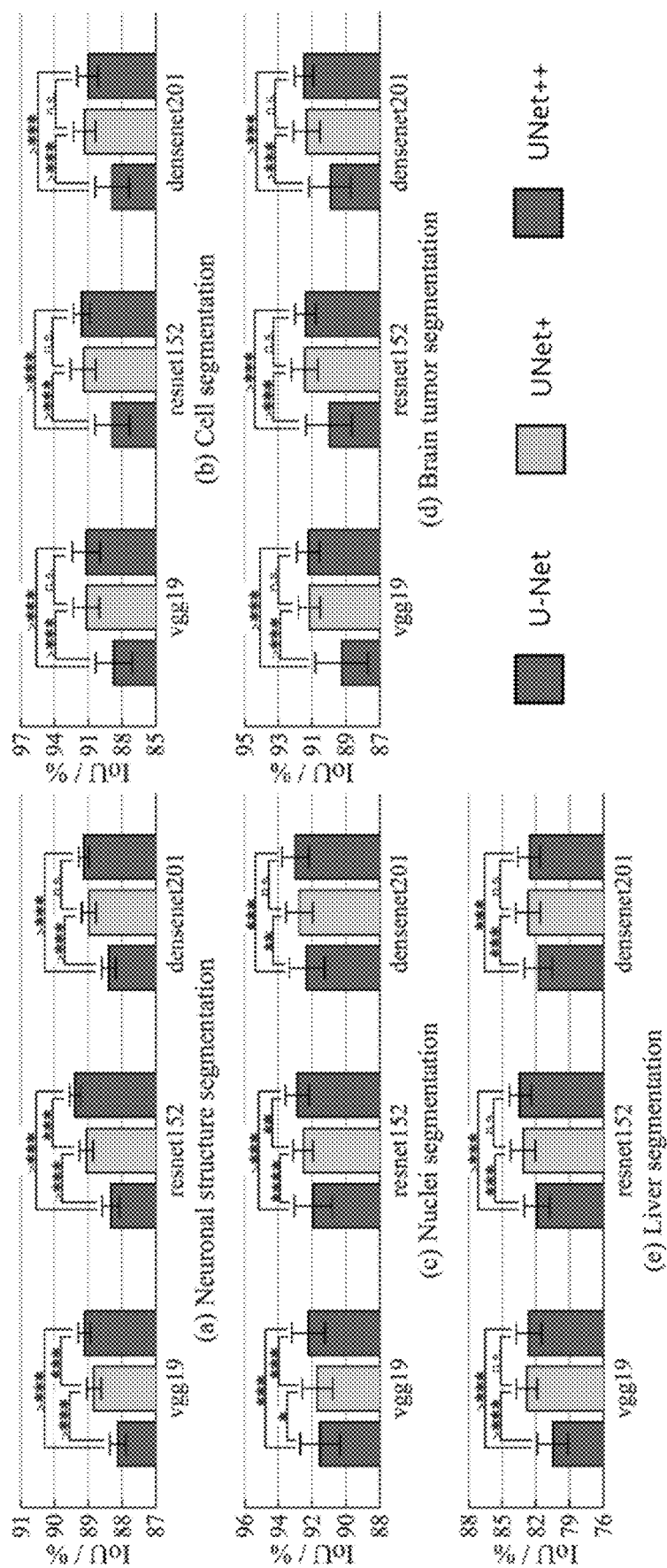
FIG. 3F shows the improvement in performance as contributed by the UNet++ model over prior known techniques.

FIG. 3F shows the improvement in performance as contributed by the UNet++ model over prior known techniques. As may be observed here, UNet++ significantly improves disease and organ segmentation over prior known techniques in support of aim 2 (element 202). Evaluated on five image segmentation tasks, including neuronal structure segmentation, cell and nuclei segmentation, brain tumor and liver segmentation, the Unet++ structure proves through statistical analysis that the model significantly outperforms the original U-Net on every task.

Figure 3G:
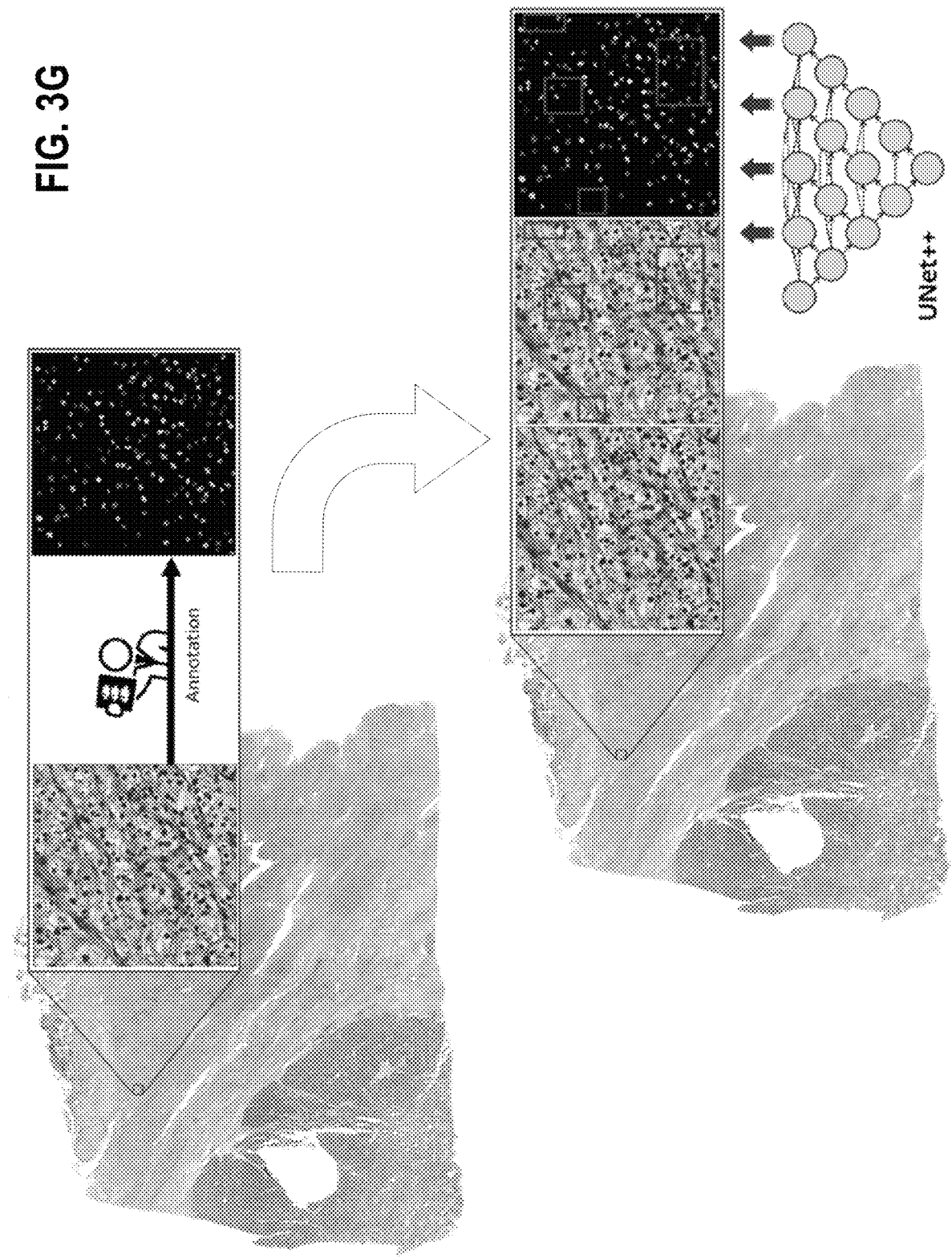
FIG. 3G depicts the use of existing annotation techniques optimized to utilize the advanced UNet++ architecture, in accordance with disclosed embodiments.

FIG. 3G depicts the use of existing annotation techniques optimized to utilize the advanced UNet++ architecture. Active learning may be further optimized by leveraging the unique architectural design of the UNet++ architecture as is depicted here. In so doing, rather than annotating all of the objects in the entire image, processing is made more efficient by selecting the most important regions for human experts to annotate, with the rest to be done by the machine. This optimized procedure is made possible through the use of the unique architecture design of UNet++ because each of the four branches in the Unet++ can give an annotation suggestion for each pixel in the image simultaneously, thus improving upon prior known techniques. With prior techniques, it was necessary for the human experts have to draw contours for each and every nuclei so as to segment nuclei from an image, which is an extremely time-consuming process.

The resulting deep neural network learns visual representation through multiple semantic levels. By fully integrating each and every level of representation, more precise and comprehensive results may be attained in support of aim 2 (element 202).

Intertwining the visual representation provides image segmentation that can help compute clinically more accurate and desirable imaging bio-markers or precise measurement. And through the use of model pruning, it is further possible to exert important impacts on deploying computer-aided diagnosis (CAD) systems to mobile devices capable of executing on ordinary desktops and laptops in conventional physician and clinical practices.

Figure 4A:
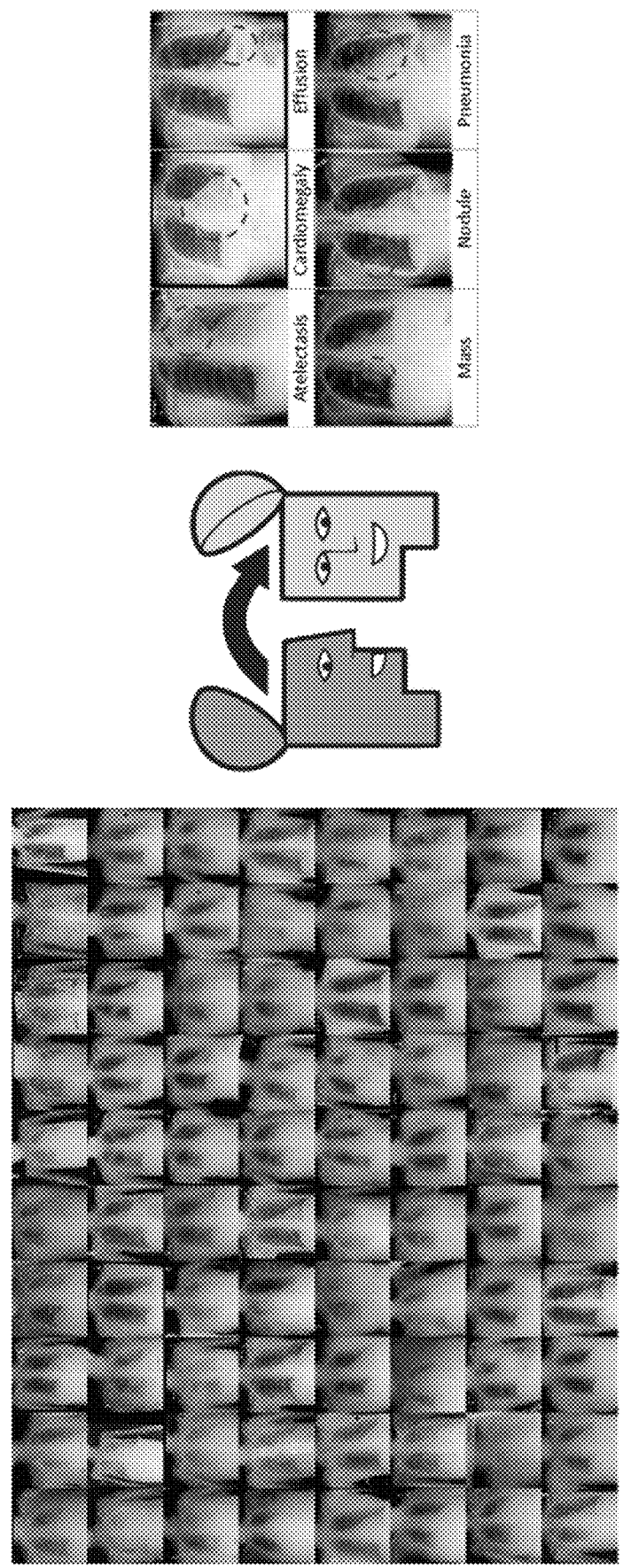
FIG. 4A depicts the process of extracting generic knowledge directly from un-annotated images, in accordance with described embodiments.

FIG. 4A depicts the process of extracting generic knowledge directly from un-annotated images, in accordance with described embodiments. In particular, in addition to the use of annotated images as described previously, it is also important to recognize the power of unlabeled images in support of aim 3 (element 203). Deep model processing can transfer these generic knowledge to many other imaging tasks so as to address the problem of how to utilize potentially millions of input images without the benefit of systematic annotation.

Figure 4B:
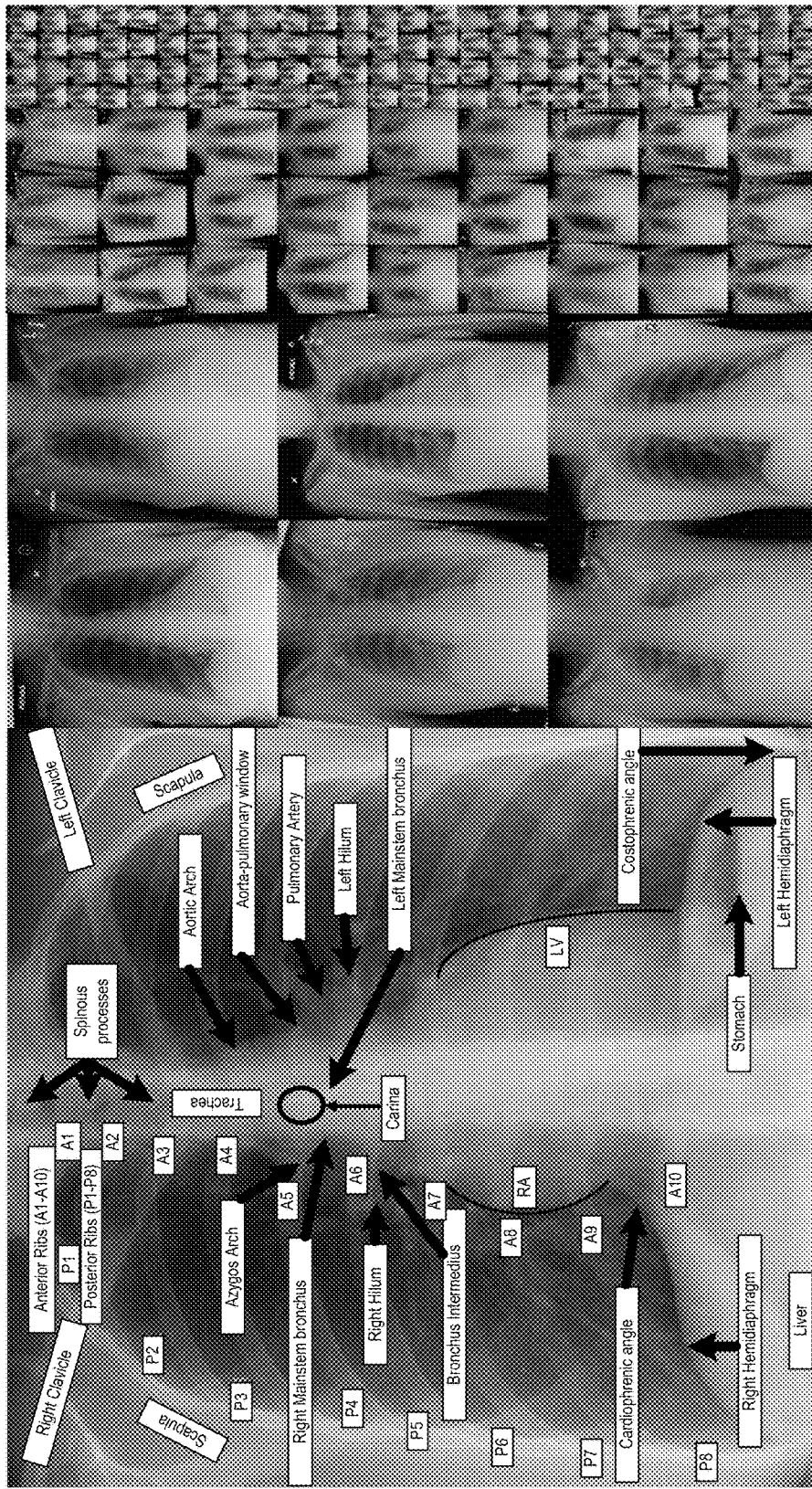
FIG. 4B depicts that medical images are embedded with consistent and recurring anatomical structure which, through the use of such information, it is possible to empower deep models with generic and transferable image representation built upon the consistent and recurrent anatomy, in accordance with disclosed embodiments.

FIG. 4B depicts that medical images are embedded with consistent and recurring anatomical structure which, through the use of such information, it is possible to empower deep models with generic and transferable image representation built upon the consistent and recurrent anatomy.

Figure 4C:
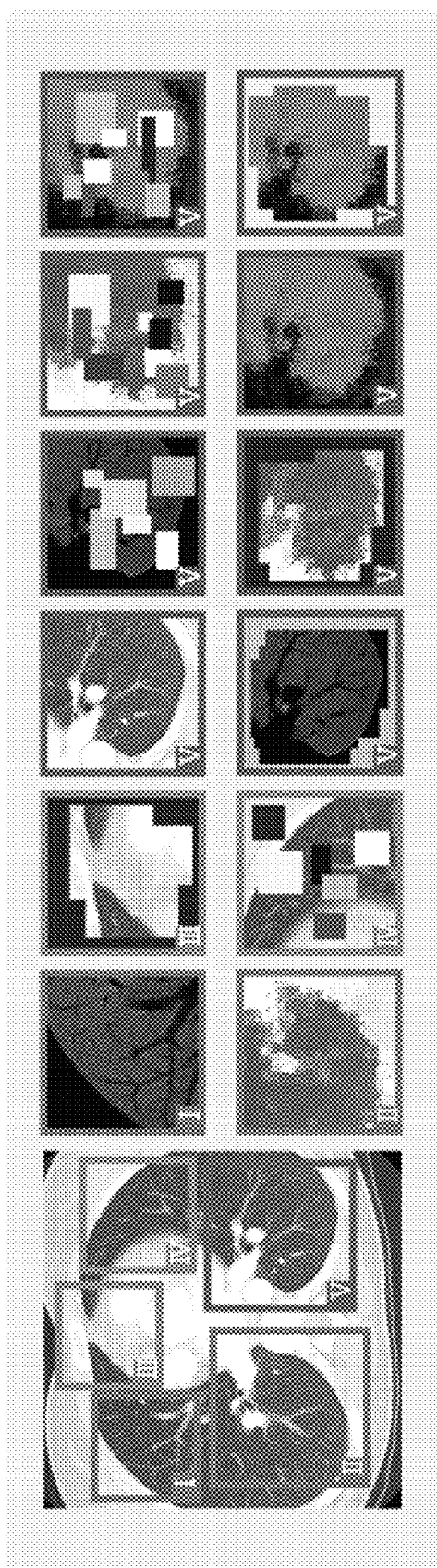
FIG. 4C depicts an image restoration task which helps the model to learn image representation, in accordance with disclosed embodiments.
Figure 4C:
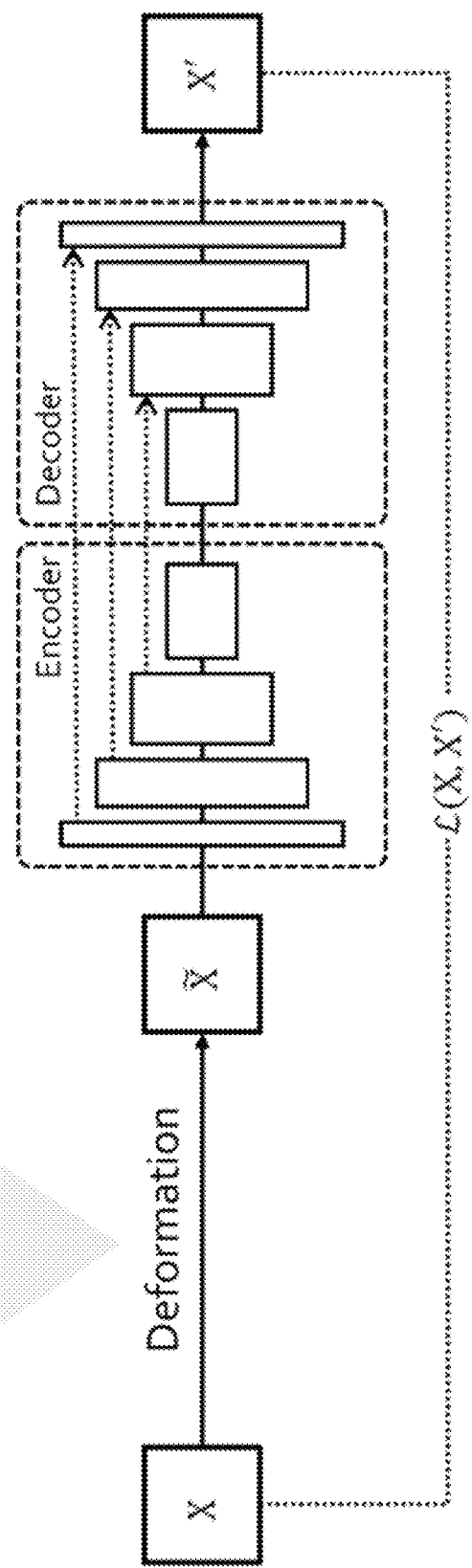

FIG. 4C depicts an image restoration task which helps the model to learn image representation. The proposed framework depicted here is designed as a simple image restoration task in which, given an image, the image is first deformed and then fed into a model to let the model learn how to restore the transformed image back into the original image. To deform the image, four different image transformation approaches are utilized, each allowing the model to learn from different perspectives. For example, the model can learn organ appearance, organ texture and local boundaries, and organ spatial layout and geometry, and many more. By permitting learning from multiple perspectives, the process is better enabled to build generic and transferable models support of aim 3 (element 203). The process learns representation directly from images without any human manual annotation and leads to powerful target models for many medical imaging applications through the process of transfer learning. In such a way, a trained model has is able to achieve the same accuracy as prior known techniques while reducing at least 30% of the annotation cost over prior methods.

The clinical impacts of aim 3 (element 203) are therefore observed to include transfer learning which can greatly reduce the cost and effort required to build a dataset and to retrain the model. For instance, rather than building a model from scratch, which demands numerous data and label acquisition, a smaller dataset can be used to efficiently fine-tune the existing model. Additionally, the generic pre0-trained models serve as a primary source of transfer learning for many medical imaging applications, thus leading to accelerated training and improved overall performance, thus potentially leading to the Holy Grail of Models Genesis, effective across diseases, organs, and modalities.

Figure 5A:
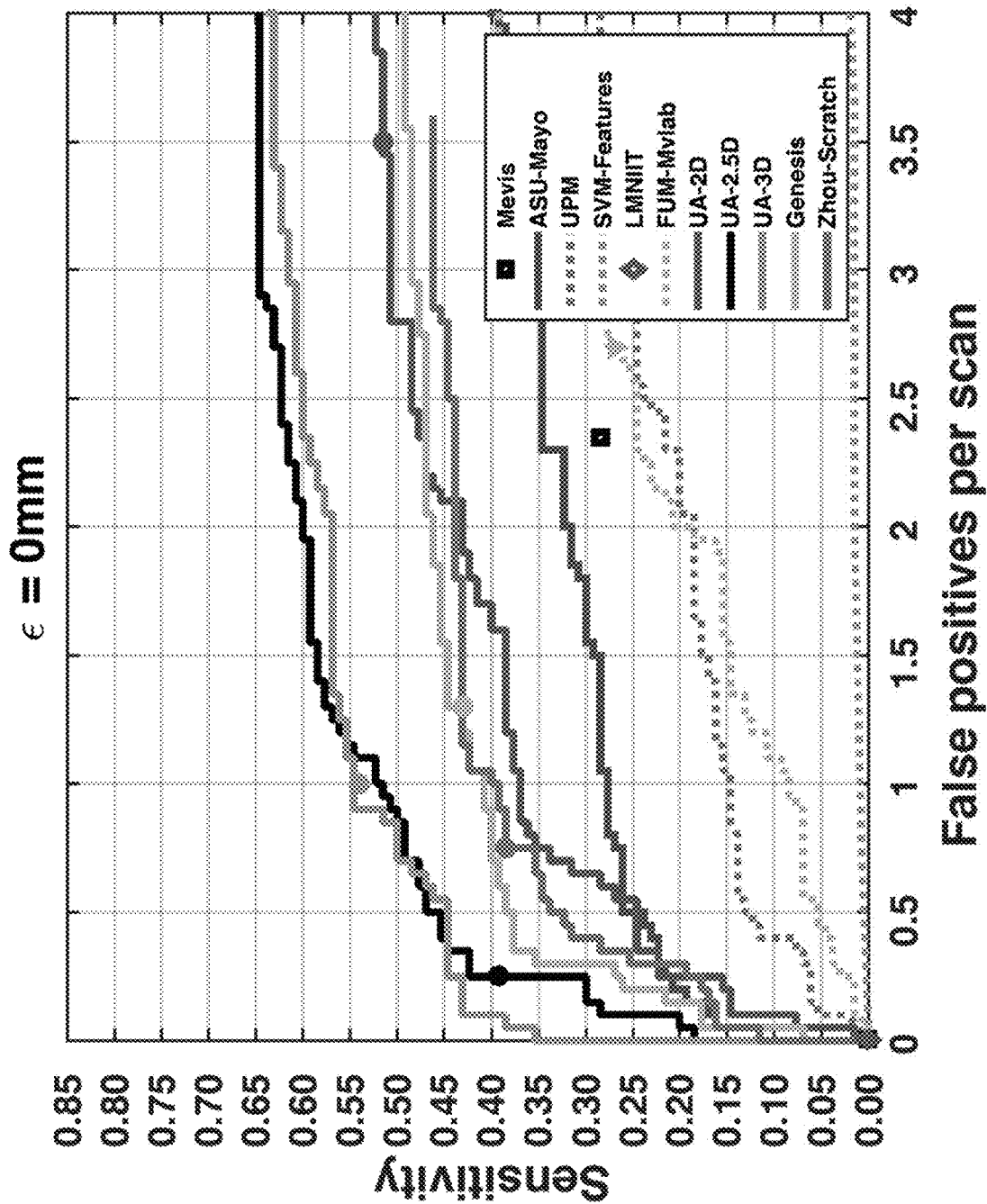
FIGS. 5A, 5B, and 5C compare the top participating teams of the CAD-PE challenge, in accordance with disclosed embodiments.
Figure 5B:
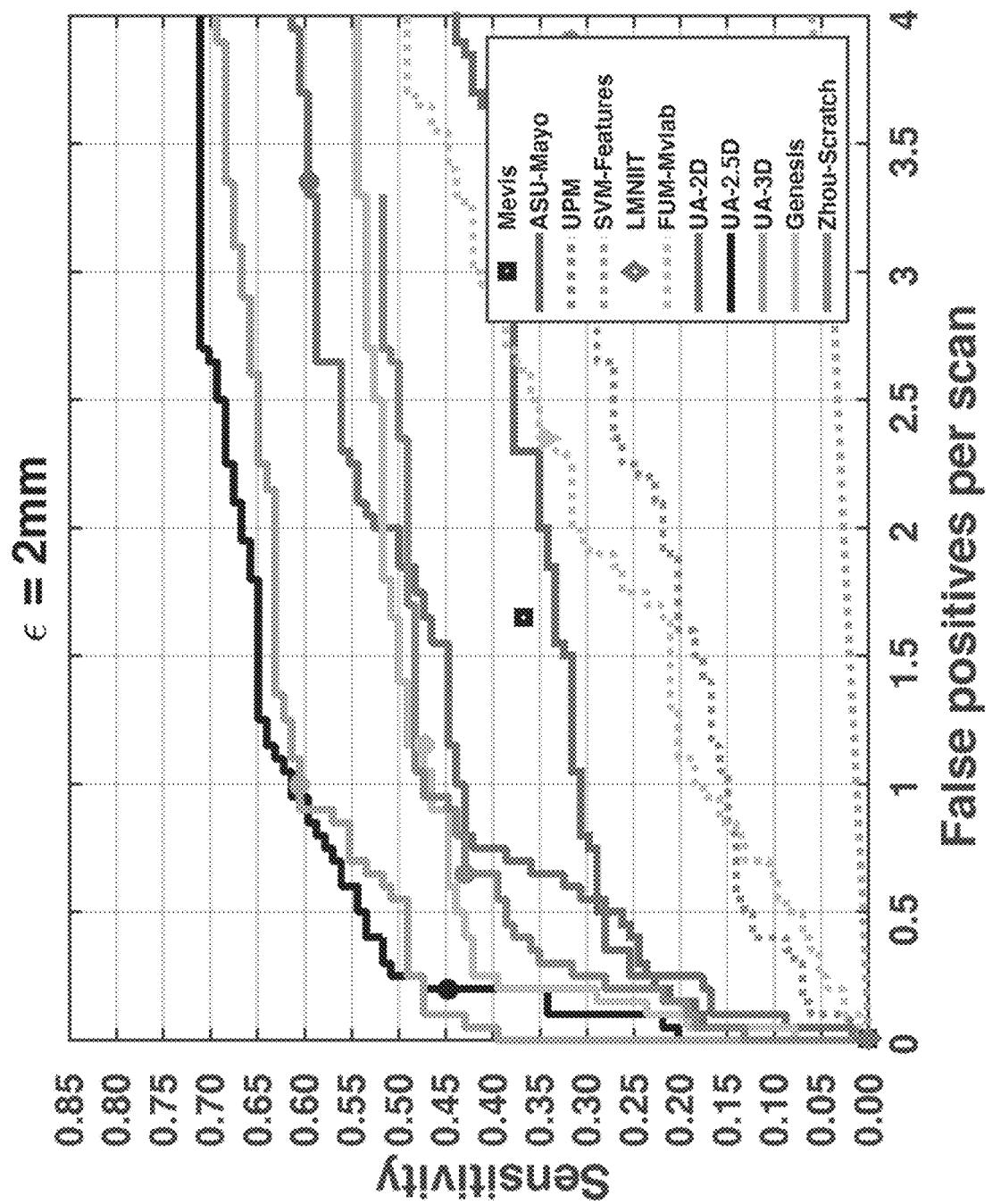
Figure 5C:
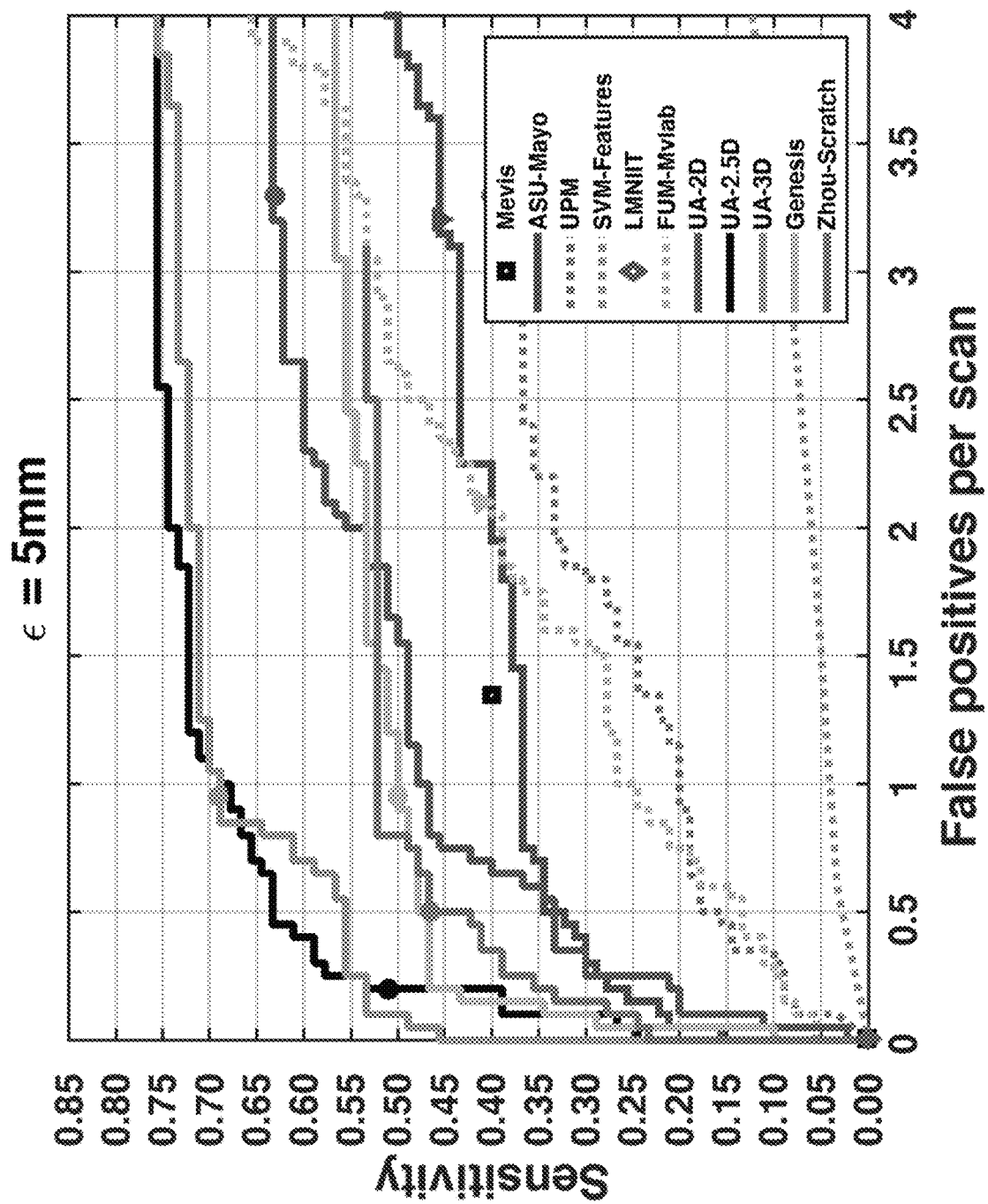

FIGS. 5A, 5B, and 5C compare the top participating teams of the CAD-PE challenge. For each method, the Free-Response Operating Characteristic (FROC) curves are plotted. The PE CAD methodology as described herein was directly evaluated on the 20 CTPA test scans, without using any training scans provided by the challenge. The term e denotes the localization error. That is, a detection is considered a true positive as long as the detection falls within $\varepsilon$ distance from the ground truth for PE. The performance at $\varepsilon=0$ mm provides greater benefits for clinical applications than at 2 mm and 5 mm. As reported, the PE CAD methodology (e.g., Genesis) is ranked third among the participating teams, achieving a sensitivity of 46% at 2 false positives per scan ($\varepsilon=0$ mm). This sensitivity is substantially higher than any previous method, which holds a sensitivity of 33% (ASU-Mayo), highlighting the importance of 3D VOIR and Models Genesis for PE detection. Note that the leading solutions (UA-2.5D and UA-3D) have not only been trained on the 20 training scans, but also had access to an extended training dataset with 51 additional CTPA scans. Therefore, use of the PE CAD methodology is reasonably competitive when compared with previously known state-of-the-art techniques.

Comparing with the state-of-the-art: To further examine the robustness of the described PE CAD system and supporting methodologies, results from the PE-CAD challenge are considered within which the disclosed system and methodology was used. All participating teams were allowed 20 training scans provided by the challenge to develop their systems, and the final performance was evaluated on the additional 20 unseen scans. As shown in FIGS. 5A, 5B, and 5C the CAD system (Genesis) is ranked third among the participating teams. The top two winners of the challenge, UA-3D and UA-2.5D, have utilized an extended training set released by the challenge organizers; therefore, their systems are significantly better than others. On the other hand, for the sake of the experiments described herein, the unseen test scans were utilized to evaluate the disclosed system, which was developed even without using the 20 training scans from the challenge. As seen, the performance of the described system is fairly robust to the different datasets. Considering the potential domain gap between the PE-CAD challenge and the in-house dataset used here, it is further anticipated that a better performance will be realized once the disclosed system is adapted into the PE-CAD training set in the future. The ASU-Mayo plot was the previous submission by the same inventors of the described methodology, which used the VOIR approach to yield a consistent, compact, and discriminative image representation to improve the perception of PE.

The current system has made three advancements: (1) extending VOIR to the 3D version, (2) utilizing three-dimensional models and data, and (3) initializing models with Models Genesis. Consequently, the enhanced system achieves a significantly higher sensitivity of 46% at 2 false positives per scan ($\varepsilon=0$ mm) increasing the sensitivity by over 10% than the previous system.

Discussion & Conclusion—The current state of clinical PE CAD: The computer-aided pulmonary embolism detection is an illustrative example of how deep learning methods have been integrated into clinical image interpretation. With an estimated 180,000 deaths per year in the United States, the rapidly increasing CTPA examinations far exceed the availability of subspecialty trained cardiopulmonary radiologists To address the un-met need for interpretation, general radiologists are also assigned to look through some of the examinations.

Accurately interpreting CTPA examinations requires significant training and experience, so the discordance between cardiopulmonary and general radiologists may exceed 25% if they interpret the same examination Due to inaccurate interpretations, including false-negative studies (failure to detect emboli) and false-positive studies (diagnosing emboli that are not present, or "over-diagnosis"), there is a significant risk of morbidity and mortality for patients.

Deep learning methods have been developed to assist radiologists with the task of PE detection and exclusion.

Several studies suggest that radiologists who use current CAD systems can improve the sensitivity from approximately 77-94% to 92-98%.

One particular system, developed by AIDOC medical (Tel Aviv, Israel), has recently been adopted by Mayo Clinic. Once a CTPA examination is transferred from the CT scanner to radiologists for interpretation, the system will perform the task of PE detection and exclusion in the backend. This system runs "silently" in the background and determines results as either negative or positive for PE. If positive, a pop-up window will localize the embolus for radiologist confirmation.

A study by the AIDOC algorithm showed a sensitivity of 92.7% on a per-patient basis with a false positive rate of 3.8%, or 0.12 false-positive detection. Most notably, the average processing time for the algorithm was 152 seconds, but typically this processing occurs while the data is being transferred from the CT scanner to the picture archiving communication system. Thus, the images are not completely available for radiologists to review immediately. An additional 25 seconds was required for case uploading.

In practice, the AIDOC system analysis is either complete and ready for review when the study is opened by the radiologist, or the case is being actively processed. The examination is open for interpretation and the results are commonly available before the radiologist completes the review of the study. Such a PE CAD system cannot substitute the doctor (nor was it designed to), but definitely it makes radiologists better and faster decision makers, playing a supporting and final interpretative role in medical diagnosis.

Conclusion and broader impacts: The introduction of deep learning methods in clinical medicine, particularly diagnostic imaging, has rapidly stimulated many medical applications in recent years. As described here, several important characteristics of medical images and pressing clinical needs are reviewed to highlight their strengths and limitations. Accordingly, the techniques we devised were mainly inspired by these imaging characteristics, while the medical applications we chose were deeply motivated by the clinical needs.

Furthermore, the end-to-end CAD system for pulmonary embolism detection is presented as an example of how deep learning methods address clinical problems. It is further illustrated that the annotation efficiency in several key facets of the system and the PE CAD system's robustness has been demonstrated in an open challenge. Numerous other deep learning applications are already available to assist radiologists with interpreting a wide variety of disorders from images, functioning as a "second reader." These applications hold promise, both for providing increased accuracy through enhanced detection and specificity, and additionally for mitigating workloads experienced by radiologists due to the rise of advanced imaging techniques.

Conclusion and Future Premise

Towards annotation-efficient deep learning: Despite the super-human performance of deep learning methods in a few medical applications, its prohibitively high annotation costs raise doubts about their feasibility of applying to those medical specialties that lack such magnitude of annotations. This paper systematically introduces techniques for developing annotation-efficient deep learning that enable models to (1) smartly identify the most significant subjects to be annotated, (2) effectively aggregate multi-scale image features to maximize the potential of existing annotations, and (3) directly extract medical knowledge from images without manual annotation.

Practice of the disclosed embodiments provide contributions in computer-aided diagnosis that support many aspects of medical image interpretation, including disease detection, classification, and segmentation. The experimental results on twelve distinct medical applications demonstrate that with a small part of the dataset annotated, deep learning methods can be delivered that approximate or even outperform those that require annotating the entire dataset. This observation is encouraging and significant because it addresses the problem of limited annotated data, which is the main obstacle standing between deep learning methods and their clinical impact.

The devised methodologies are advantageous on over-represented diseases with abundant existing annotations and also shed new light on many more underrepresented diseases with the deep learning marvel, dramatically reducing annotation costs while maintaining high performances. More importantly, by advocating for open access, open data, and open source, such techniques stand to greatly benefit the research community.

Eight out of the twelve medical applications were taken from publicly available medical imaging benchmarks, ensuring the reproducibility of the results. Further, the codes and models were released to the public, making three developed techniques (ACFT, UNet++, and Models Genesis) open science to stimulate collaborations among the research community and to help translate these technologies to clinical practice. The ACFT, UNet++, and Models Genesis models presented by the inventors have been quickly adopted by the research community and reviewed by some of the most prestigious journals and conferences in the field, served as competitive baselines, and enlightened the development of more advanced approaches.

Moreover, although the described techniques were initially derived from the medical imaging context, their annotation-efficiency and generalizability have been demonstrated by independent research groups from alternative fields, such as text classification, vehicle type recognition, streaming recommendation system, etc. Lessoned from computer vision, annotation is one of the most significant cornerstones for algorithm development and validation. Annotation-efficient deep learning facilitates quick, iterative improvements of the algorithm, but large, diverse, annotated datasets remain necessary for performance testing. In addition to the sufficient population of patients, it is desirable to also evaluate how the performance generalizes to other medical images acquired from different devices, conditions, and sites before eventually adopting the techniques into the clinical practice. Therefore, the increasing annotation demands are anticipated to continue to present serious obstacles due to the lack of budget, time, and expertise. Big data is an inevitable trend in the future and with the increasing imaging studies rising workloads of radiologists, and growing needs for technologies, the age of big data may be embraced. The purpose of annotation-efficient deep learning is not to strangle the throat of annotating per see, but rather, to speed up creating such annotated datasets to enable high-performance deep learning methods with a minimal set of human efforts.

Towards the learning objective of computer vision: As one of the most important subjects in AI, computer vision enables computers to identify, perceive, and recognize people, places, and things, and ultimately imitate natural vision. The current state of computer vision is vulnerable to attack, un-adaptable to new surroundings, and incapable of life-long learning. To match natural vision, the journey has only just begun. Is annotation needed to develop human-like computer vision? The necessity, formation, and quantity of annotation is fundamentally dependent on the learning objective, specifically: What should the computer learn?

An established learning objective can determine whether or not to collect manual annotation and, if yes, what is the type of the annotation. For example, the learning objective of classifying 14 diseases requires the annotator to tell the types of diseases in the image; the learning objective of segmenting lung nodule requires the annotator to outline the boundary of each nodule.

Defining the learning objective for specific imaging tasks is straightforward, but the learning objective for the task of matching natural vision is still inconclusive. This has led to spiraling debates on the necessity of acquiring manual annotation for developing computer vision to match natural vision. In essence, the debates are about the learning objective of computer vision. The earliest attempts to develop computer vision involved the idea that a visual concept (e.g., cat) can be described and predicted by several attributes (e.g., round face, chubby body, two pointy ears, and a long tail). If any object carries these preset attributes, the computer can identify cats from many images. While more advanced and sophisticated attributes arise, the underlying learning objective behind these approaches remains similar, such as identifying these descriptive attributes from the image.

However, by using these approaches, computers can make many simple mistakes, such as when (1) the objects are overlapping, (2) the object's position and shape are distorted, or (3) the object is conceptually difficult to define. The attribute-based approaches lack reliability, as countless concepts demand excessive manual intervention for their definition and numerous variations that can eliminate the rule of conceptual modeling. To move away from extensive attribute engineering, researchers have sought to automate feature learning for object recognition. Inspired by cognitive science and neuroscience, prior techniques have developed an algorithm called deep neural networks that makes automated feature learning possible, but its strengths were not appreciated until the availability of big image datasets. At the beginning of 2007, a large-scale image dataset was created, with the curators believing that the development of reliable computer vision systems requires a lot of human annotated examples.

Imagine a child's eyes as a pair of biological cameras, and they take one image about every 200 milliseconds. By age three, the child would have seen a tremendous number of real-world images. This observation promoted multiple large-scale, systematic-labeled datasets in the last few years. Deep neural networks trained with these datasets have enabled enormous advances in computer vision, leading to amazing results on some real-world tasks. Additionally, in academic settings, deep neural networks almost always outperform alternative attribute-based approaches on benchmark tasks. Combining large datasets, deep neural networks, and powerful computers, categorical supervised learning emerged as a new learning paradigm, where the learning objective for computers is to minimize the error between computer predictions and human labels.

Here, humans play a very important role in training computers in this learning paradigm because humans must provide all categorical labels for the dataset. Although training deep neural networks using categorical supervised learning is very effective, there are three inherent restrictions: (1) computers can only differentiate the specific categories given by humans, but not beyond; (2) computers can perform poorly on real-world images outside the dataset; and, most importantly, (3) the resulting computer vision is much less general, flexible, and adaptive than natural vision.

Categories and concepts in the real world can be far more comprehensive than those given in the benchmark datasets. It is because the categories in the real world are non-orthogonal (e.g., cat and tiger vs. cat and plane), imbalanced (e.g., long-tail distribution for most classes), and exponential (e.g., classes with hierarchical sub-classes). Since a computer is unable to learn categories beyond what has been given, the annotating work can keep going forever, and the resultant computer vision would always be tied with specific categories. The categorical supervised learning paradigm is essentially the same as attribute-based learning, where categories serve as attributes to help computers understand the world.

The major concern is not the challenge to annotate an adequate number of images but rather the fact that learning paradigms are fundamentally asymmetrical between computer vision and natural vision, in which the former is currently built upon categorical labels while the latter is developed from images without any label. Human babies and animals establish vision naturally without direct supervision, such that in nature, there is no dictionary of concepts available, and yet, they nevertheless learn these through real-world experiences and interactions.

Although the top-down categorization based on a linguistic definition can help develop task-specific computer vision systems, it might be unnecessary for a general-purpose visual system. To deal with the enormous complexity of natural images and obtain the rich understanding of visual scenes that the human achieves, today science still yearns to know the underlying objective of natural vision. The dissimilarity between natural vision and current computer vision suggests alternative learning paradigms. Self-supervised learning is an interesting reflection on the general thoughts on learning representation in a way similar to natural vision. This learning paradigm has existed for some time, but its power historically has lagged behind the state-of-the-art categorical supervised learning. However, the recent pace of progress in self-supervised learning has increased dramatically and led to visual representation that approaches even surpasses the representation learned from supervised categorization.

Self-supervised learning is hoped to ultimately replace the ubiquitous categorical supervised learning in advanced computer vision going forward. Unlike categorical supervised learning, a computer does not have to learn orthogonal, balanced, and finite categories from human annotation; instead, it learns by studying properties of real-world images. Self-supervision promises to get away from top-down categorization and enable continuous life-long learning. Self-supervised learning has been said to be the "key to human-level intelligence." The line of research on self-supervision is more closely investigating the objective of natural vision development.

As a learner interacts with the environment, one of the most common objectives is to survive, to avoid either being attacked or starving, which has led to two major research avenues in self-supervision: (1) learning a predictive model to fill in the blank and (2) learning a contrastive model to distinguish multiple views. First, to prevent being attacked or killed, a learner should develop meaningful expectations about the world, coming up with a hypothesis of the world and then verifying it.

As a result, the predictive model predicts some hidden information (e. g., color, future events, or contexts of an image) to perceive prior knowledge and physical properties in nature, such as the sky being blue or a running beast approaching you. Second, to ensure survival, a learner is expected to distinguish objects (e.g., determining food edibility based on color, shape, texture, etc.). It should be noted that distinguishing is different from categorizing because the distinction can separate things even if they belong to the same category. Consequently, instead of categorization, the contrastive model compares images that have undergone strong data augmentation to learn image representation, which is resilient to various view changes.

In the context of the disclosed embodiments, a similar principle was followed to develop general-purpose computer vision. Specifically, to not define anything. While learning algorithms are continually changing as better methods are developed, one trend that is not going away is the move towards increased levels of automation. Thus, the inventors sought out a way to let computers autonomously interact with images and capture visual representation keeping away from manually defining attributes, categories, etc. Automated feature learning will save time, build generic models, create meaningful features, and encourage learning from diverse data sources. As of now, compared with natural vision, the current state of self-supervision is incomplete in at least three ways.

First, the choice of augmented views is supervised by humans. Data augmentation is widely used for training both predictive and contrastive models due to its simplicity and efficiency. A predictive model restores the original images from the transformed ones through data augmentation; a contrastive model distinguishes the same image from different views generated from data augmentation. However, humans must pre-define a set of data augmentation specific to each task because some augmentations can make a task ambiguous, unsolvable, or trivial, leading to degenerate learning. Here there are several examples, including: cropping patches from images can occlude the target object; permutating color is mostly not applicable to grayscale images; predicting rotation angles in medical images can be trivial due to the consistent anatomical structure. Many recent works appear to automate data augmentation in self-supervised learning, one of which is to use videos rather than images. Humans learn from a sequence of meaningful images instead of a large number of non-related still images because videos naturally associate with different continuous views. Another way is to use generated images so that bottleneck features can manipulate the image context to ensure existence of the target object.

Second, the choice of model architectures is supervised by humans. In the existing literature, methods are generally developed to learn the weights (parameters) of a fixed architecture without using labels, and these weights are evaluated by transferring to a target supervised task. Prior techniques explored the possibility of using such methods to learn architecture without using labels. The neural architecture search seems to relax the manual design, but the search space heavily relies on humans. There are three challenges associated with the existing approaches. In particular, (i) the neural connection can never be found if it is not included in the original search space, given that the search space limits what neural architecture can be discovered; (ii) the searching will terminate into a fixed architecture if it meets a local minimum, conversely, the neural connection in human brains is dynamically evolving throughout the lifespan; (iii) vast computational resources are required for the neural architectural search, while the resultant architecture cannot guarantee superior to human-engineered architectures. In addition, although convolutional neural networks are currently dominant in most imaging tasks, another architecture called transformer was proven more powerful to encode long-term dependencies among data, therefore exceeding in analyzing sequences of data such as language and video.

Third, the choice of pretext tasks is supervised by humans. That being said, a wide range of learning schemes with varying learning objectives are currently designed by humans, such as predicting rotation, augmentation, color, etc. But the fact is, science remains unsure how exactly natural vision is developed, as humans are the users, not the designers. It is possible that pre-defined learning schemes, either filling in blanks or contrasting views, could dilute the power of self-supervised learning. Given an image, human vision is developed by multi-tasking, such as depth estimation, motion prediction, orientation perception, object detection, etc. The types of these tasks are not pre-defined but driven by underlying objective. We have given special prominence to the objective that drives a learner to develop vision because it is the learning objective that mostly makes such diverse types of tasks for us to learn, even though sometimes our supervisors (parents, teachers, primers) suggest some specific tasks for us. Instead of devising many pretext tasks, the real mission is to figure out the true objective beyond vision, which comes up with a research field called learning to learn or meta learning. According to the concept of meta learning, a learner itself must be exposed to a large number of tasks and tested on their ability to learn new tasks. Thus, humans do not have to design which tasks to solve, and instead, computers make up their own game to develop computer vision.

As revealed in a historical review, it remains an open problem to construct a complete, unified learning objective of computer vision using one concise equation. In the past decades, we have made exciting progresses by discovering partial learning objectives that make computers accomplish specific tasks and developing the critical components that collectively simulate natural vision. We are heading towards the direction where the advancements in computer vision rely on less and less manual annotation to secure comprehensive visual knowledge from images.

Figure 6:
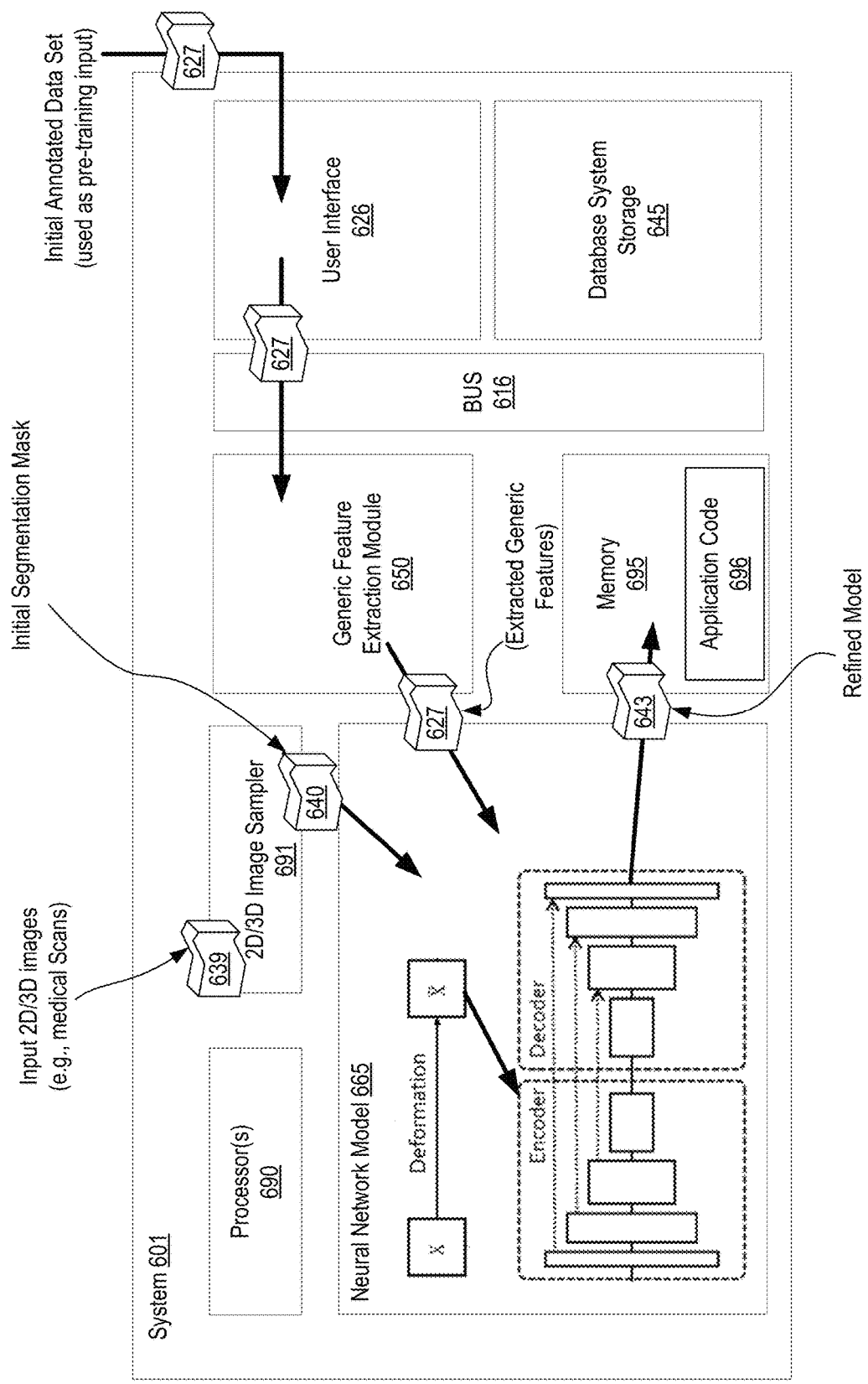
FIG. 6 shows a diagrammatic representation of a system within which embodiments may operate, be installed, integrated, or configured, in accordance with one embodiment.

FIG. 6 shows a diagrammatic representation of a system 601 within which embodiments may operate, be installed, integrated, or configured. In accordance with one embodiment, there is a system 601 having at least a processor 690 and a memory 695 therein to execute implementing application code 696. Such a system 601 may communicatively interface with and cooperatively execute with the benefit of remote systems, such as a user device sending instructions and data, a user device to receive as an output from the system 601 a semantics-enriched pre-trained model having a trained encoder-decoder structure with generic feature extraction and refinement operations as performed by the system 601, or systems within a networked or within a client-server environment, etc.

According to the depicted embodiment, the system 601, includes the processor 690 and the memory 695 to execute instructions at the system 601. The system 601 as depicted here is specifically customized and configured to implement advancements towards annotation-efficient deep learning in computer-aided diagnosis, in which trained deep models are then utilized for the processing of medical imaging.

According to a particular embodiment, system 601 is further configured to execute instructions via the processor for learning annotation-efficient deep learning from non-labeled medical images to generate a trained deep-learning model by applying a multi-phase model training process. Such a process includes at least: pre-training a model by executing a one-time learning procedure using an initial annotated image dataset 627; iteratively re-training the model by executing a fine-tuning learning procedure using newly available annotated images without re-using any images from the initial annotated image dataset; selecting a plurality of most representative samples related to images of the initial annotated image dataset and the newly available annotated images by executing an active selection procedure based on the which of a collection of un-annotated images exhibit either a greatest uncertainty or a greatest entropy; extracting generic image features (via the generic feature extraction module 650) from the initial annotated image dataset, the newly available annotated images, and the plurality of most representative samples selected; updating the model using the generic image features extracted via processing through the neural network model 665 to produce a refined model 643 based on the extracted generic features 627; and outputting the model as the trained deep-learning model for use in analyzing a patient medical image which is not included in any training image for the trained deep-learning model.

Bus 616 interfaces the various components of the system 601 amongst each other, with any other peripheral(s) of the system 601, and with external components such as external network elements, other machines, client devices, cloud computing services, etc. Communications may further include communicating with external devices via a network interface over a LAN, WAN, or the public Internet.

Figure 7:
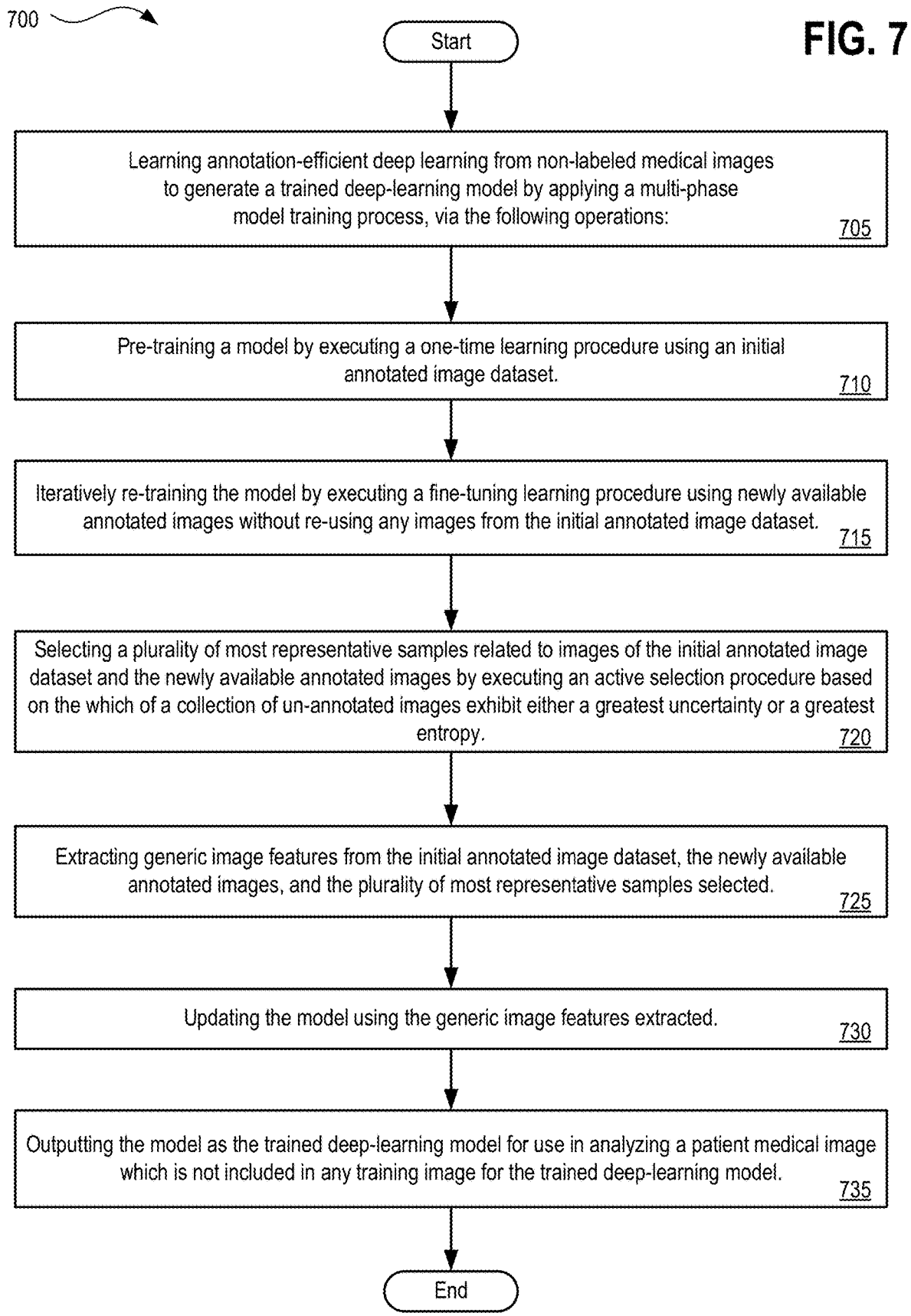
FIG. 7 depicts a flow diagram illustrating a method for implementing advancements towards annotation-efficient deep learning in computer-aided diagnosis, in which trained deep models are then utilized for the processing of medical imaging, in accordance with disclosed embodiments.

FIG. 7 depicts a flow diagram illustrating a method 700 for implementing advancements towards annotation-efficient deep learning in computer-aided diagnosis, in which trained deep models are then utilized for the processing of medical imaging, in accordance with disclosed embodiments. Method 700 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 601 (see FIG. 6) and the machine 801 (see FIG. 8) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 700 depicted at FIG. 7, there is a method performed by a system specially configured for the learning of annotation-efficient deep learning from non-labeled medical images to generate a trained deep-learning model by applying a multi-phase model training process. Such a system may be configured with at least a processor and a memory to execute specialized instructions which cause the system to perform the following operations:

At block 705, processing logic learns annotation-efficient deep learning from non-labeled medical images to generate a trained deep-learning model by applying a multi-phase model training process, by performing the operations that follow.

At block 710, processing logic pre-trains a model by executing a one-time learning procedure using an initial annotated image dataset.

At block 715, processing logic iteratively re-trains the model by executing a fine-tuning learning procedure using newly available annotated images without re-using any images from the initial annotated image dataset.

At block 720, processing logic selects a plurality of most representative samples related to images of the initial annotated image dataset and the newly available annotated images by executing an active selection procedure based on the which of a collection of un-annotated images exhibit either a greatest uncertainty or a greatest entropy.

At block 725, processing logic extracts generic image features from the initial annotated image dataset, the newly available annotated images, and the plurality of most representative samples selected.

At block 730, processing logic updates the model using the generic image features extracted.

At block 735, processing logic outputs the model as the trained deep-learning model for use in analyzing a patient medical image which is not included in any training image for the trained deep-learning model.

According to another embodiment of method 700, pre-training the model comprises adopting weights from one or more other models having been pre-trained using ImageNet.

According to another embodiment of method 700, pre-training the model comprises adopting a generic CNN having previously been directly pre-trained from annotated medical images.

According to another embodiment, method 700 further includes: computing an uncertainty measure for each of the images based on disagreements amongst multiple trained models.

According to another embodiment of method 700, images from the collection of un-annotated images that exhibit a greatest uncertainty correspond to those images having the greatest computed uncertainty measure among the collection of un-annotated images.

According to another embodiment, method 700 further includes: computing an entropy measure for each of the images by (i) capturing multiple patches from a sample image among the collection of un-annotated images and (ii) measuring diversity over the multiple patches augmented from the same sample image to calculate the entropy measure based on one or more of Gaussian distance, standard deviation, variance, or divergence amongst the patches for the sample image.

According to another embodiment of method 700, images from the collection of un-annotated images that exhibit a greatest entropy correspond to those images having the greatest computed uncertainty measure among the collection of un-annotated images.

According to another embodiment of method 700, applying the multi-phase model training process, further includes: executing a deep supervision procedure by combining predictions from varying resolutions of feature maps within a network of the model to increase conversion rates of the model.

According to another embodiment of method 700, executing the deep supervision procedure further comprises enforcing intermediate layers of the network to learn discriminative features within training images for the model.

According to another embodiment of method 700, extracting the generic image features from the initial annotated image dataset, the newly available annotated images, and the plurality of most representative samples selected, includes: executing a transfer learning procedure to learn representations directly from the un-annotated images without human intervention.

According to another embodiment, method 700 further includes: generating a prediction for the patient medical image indicating the presence or absence of disease; and outputting the predication to a user interface.

According to a particular embodiment, there is a non-transitory computer-readable storage media having instructions stored thereupon that, when executed by a system having at least a processor and a memory therein, the instructions cause the system to learn annotation-efficient deep learning from non-labeled medical images to generate a trained deep-learning model, by performing operations including: pre-training a model by executing a one-time learning procedure using an initial annotated image dataset; iteratively re-training the model by executing a fine-tuning learning procedure using newly available annotated images without re-using any images from the initial annotated image dataset; selecting a plurality of most representative samples related to images of the initial annotated image dataset and the newly available annotated images by executing an active selection procedure based on the which of a collection of un-annotated images exhibit either a greatest uncertainty or a greatest entropy; extracting generic image features from the initial annotated image dataset, the newly available annotated images, and the plurality of most representative samples selected; updating the model using the generic image features extracted; and outputting the model as the trained deep-learning model for use in analyzing a patient medical image which is not included in any training image for the trained deep-learning model.

FIG. 8 illustrates a diagrammatic representation of a machine 801 in the exemplary form of a computer system, in accordance with one embodiment, within which a set of instructions, for causing the machine/computer system 801 to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 801 includes a processor 802, a main memory 804 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 818 (e.g., a persistent storage device including hard disk drives and a persistent database and/or a multi-tenant database implementation), which communicate with each other via a bus 830. Main memory 804 includes a generic feature extractions for use in refinement 824 as well as a set of original input images 825 which constitutes at least the initial annotated dataset, as well as a deformer with an encoder and decoder 823 operating within a CNN via which to perform further processing and refinement of the pre-trained model. Main memory 804 and its sub-elements are further operable in conjunction with processing logic 826 and processor 802 to perform the methodologies discussed herein.

Processor 802 represents one or more specialized and specifically configured processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 802 may also be one or more special-purpose processing devices such as an application-specific integrated circuit (ASIC), a field programmable gate array (FPGA), a digital signal processor (DSP), network processor, or the like. Processor 802 is configured to execute the processing logic 826 for performing the operations and functionality which is discussed herein.

The computer system 801 may further include a network interface card 808. The computer system 801 also may include a user interface 810 (such as a video display unit, a liquid crystal display, etc.), an alphanumeric input device 812 (e.g., a keyboard), a cursor control device 813 (e.g., a mouse), and a signal generation device 816 (e.g., an integrated speaker). The computer system 801 may further include peripheral device 836 (e.g., wireless or wired communication devices, memory devices, storage devices, audio processing devices, video processing devices, etc.).

The secondary memory 818 may include a non-transitory machine-readable storage medium or a non-transitory computer readable storage medium or a non-transitory machine-accessible storage medium 831 on which is stored one or more sets of instructions (e.g., software 822) embodying any one or more of the methodologies or functions described herein. The software 822 may also reside, completely or at least partially, within the main memory 804 and/or within the processor 802 during execution thereof by the computer system 801, the main memory 804 and the processor 802 also constituting machine-readable storage media. The software 822 may further be transmitted or received over a network 820 via the network interface card 808.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
a memory to store instructions;
a processor to execute the instructions stored in the memory;
wherein the system is specially configured to learn annotation-efficient deep learning from non-labeled medical images to generate a trained deep-learning model by applying a multi-phase model training process, comprising:
pre-training a model by executing a one-time learning procedure using an initial annotated image dataset;
iteratively re-training the model by executing a fine-tuning learning procedure using newly available annotated images without re-using any images from the initial annotated image dataset;
selecting a plurality of most representative samples related to images of the initial annotated image dataset and the newly available annotated images by executing an active selection procedure based on the which of a collection of un-annotated images exhibit either a greatest uncertainty or a greatest entropy;
extracting generic image features from the initial annotated image dataset, the newly available annotated images, and the plurality of most representative samples selected;
updating the model using the generic image features extracted; and
outputting the model as the trained deep-learning model for use in analyzing a patient medical image which is not included in any training image for the trained deep-learning model.

2. The system of claim 1, wherein pre-training the model comprises adopting weights from one or more other models having been pre-trained using ImageNet.

3. The system of claim 1, wherein pre-training the model comprises adopting a generic CNN having previously been directly pre-trained from annotated medical images.

4. The system of claim 1, further comprising:
computing an uncertainty measure for each of the images based on disagreements amongst multiple trained models; and
wherein images from the collection of un-annotated images that exhibit a greatest uncertainty correspond to those images having the greatest computed uncertainty measure among the collection of un-annotated images.

5. The system of claim 1, further comprising:
computing an entropy measure for each of the images by (i) capturing multiple patches from a sample image among the collection of un-annotated images and (ii) measuring diversity over the multiple patches augmented from the same sample image to calculate the entropy measure based on one or more of Gaussian distance, standard deviation, variance, or divergence amongst the patches for the sample image; and
wherein images from the collection of un-annotated images that exhibit a greatest entropy correspond to those images having the greatest computed uncertainty measure among the collection of un-annotated images.

6. The system of claim 1, wherein applying the multi-phase model training process, further comprises:
executing a deep supervision procedure by combining predictions from varying resolutions of feature maps within a network of the model to increase conversion rates of the model.

7. The system of claim 6, wherein executing the deep supervision procedure further comprises enforcing intermediate layers of the network to learn discriminative features within training images for the model.

8. The system of claim 1, wherein extracting the generic image features from the initial annotated image dataset, the newly available annotated images, and the plurality of most representative samples selected, comprises:
executing a transfer learning procedure to learn representations directly from the un-annotated images without human intervention.

9. The system of claim 1, further comprising:
generating a prediction for the patient medical image indicating the presence or absence of disease; and
outputting the predication to a user interface.

10. Non-transitory computer-readable storage media having instructions stored thereupon that, when executed by a system having at least a processor and a memory therein, the instructions cause the system to learn annotation-efficient deep learning from non-labeled medical images to generate a trained deep-learning model, by performing operations including:
pre-training a model by executing a one-time learning procedure using an initial annotated image dataset;
iteratively re-training the model by executing a fine-tuning learning procedure using newly available annotated images without re-using any images from the initial annotated image dataset;
selecting a plurality of most representative samples related to images of the initial annotated image dataset and the newly available annotated images by executing an active selection procedure based on the which of a collection of un-annotated images exhibit either a greatest uncertainty or a greatest entropy;
extracting generic image features from the initial annotated image dataset, the newly available annotated images, and the plurality of most representative samples selected;
updating the model using the generic image features extracted; and
outputting the model as the trained deep-learning model for use in analyzing a patient medical image which is not included in any training image for the trained deep-learning model.

11. The non-transitory computer-readable storage media of claim 10, wherein pre-training the model comprises one of:
adopting weights from one or more other models having been pre-trained using ImageNet; or
adopting a generic CNN having previously been directly pre-trained from annotated medical images.

12. The non-transitory computer-readable storage media of claim 10:
wherein the most representative samples having the greatest uncertainty are determined by computing an uncertainty measure for each of the images based on disagreements amongst multiple trained models, wherein images from the collection of un-annotated images that exhibit a greatest uncertainty correspond to those images having the greatest computed uncertainty measure among the collection of un-annotated images; and
wherein the most representative samples having the greatest entropy are determined by computing an entropy measure for each of the images by (i) capturing multiple patches from a sample image among the collection of un-annotated images and (ii) measuring diversity over the multiple patches augmented from the same sample image to calculate the entropy measure based on one or more of Gaussian distance, standard deviation, variance, or divergence amongst the patches for the sample image, wherein images from the collection of un-annotated images that exhibit a greatest entropy correspond to those images having the greatest computed uncertainty measure among the collection of un-annotated images.

13. The non-transitory computer-readable storage media of claim 10, wherein applying the multi-phase model training process, further comprises:
executing a deep supervision procedure by combining predictions from varying resolutions of feature maps within a network of the model to increase conversion rates of the model; and
wherein executing the deep supervision procedure further comprises enforcing intermediate layers of the network to learn discriminative features within training images for the model.

14. The non-transitory computer-readable storage media of claim 10, wherein extracting the generic image features from the initial annotated image dataset, the newly available annotated images, and the plurality of most representative samples selected, comprises:
executing a transfer learning procedure to learn representations directly from the un-annotated images without human intervention.

15. The non-transitory computer-readable storage media of claim 10, wherein executing the instructions causes the system to perform operations further comprising:
generating a prediction for the patient medical image indicating the presence or absence of disease; and
outputting the predication to a user interface.

16. A method performed by a system having at least a processor and a memory therein to execute instructions for learning annotation-efficient deep learning from non-labeled medical images to generate a trained deep-learning model, wherein the method comprises:
pre-training a model by executing a one-time learning procedure using an initial annotated image dataset;
iteratively re-training the model by executing a fine-tuning learning procedure using newly available annotated images without re-using any images from the initial annotated image dataset;
selecting a plurality of most representative samples related to images of the initial annotated image dataset and the newly available annotated images by executing an active selection procedure based on the which of a collection of un-annotated images exhibit either a greatest uncertainty or a greatest entropy;
extracting generic image features from the initial annotated image dataset, the newly available annotated images, and the plurality of most representative samples selected;
updating the model using the generic image features extracted; and
outputting the model as the trained deep-learning model for use in analyzing a patient medical image which is not included in any training image for the trained deep-learning model.

17. The method of claim 16, wherein pre-training the model comprises one of:
adopting weights from one or more other models having been pre-trained using ImageNet; or adopting a generic CNN having previously been directly pre-trained from annotated medical images.

18. The method of claim 16:
wherein the most representative samples having the greatest uncertainty are determined by computing an uncertainty measure for each of the images based on disagreements amongst multiple trained models, wherein images from the collection of un-annotated images that exhibit a greatest uncertainty correspond to those images having the greatest computed uncertainty measure among the collection of un-annotated images; and
wherein the most representative samples having the greatest entropy are determined by computing an entropy measure for each of the images by (i) capturing multiple patches from a sample image among the collection of un-annotated images and (ii) measuring diversity over the multiple patches augmented from the same sample image to calculate the entropy measure based on one or more of Gaussian distance, standard deviation, variance, or divergence amongst the patches for the sample image, wherein images from the collection of un-annotated images that exhibit a greatest entropy correspond to those images having the greatest computed uncertainty measure among the collection of un-annotated images.

19. The method of claim 16, wherein applying the multi-phase model training process, further comprises:
executing a deep supervision procedure by combining predictions from varying resolutions of feature maps within a network of the model to increase conversion rates of the model; and
wherein executing the deep supervision procedure further comprises enforcing intermediate layers of the network to learn discriminative features within training images for the model.

20. The method of claim 16, wherein executing the instructions causes the system to perform operations further comprising:
generating a prediction for the patient medical image indicating the presence or absence of disease; and
outputting the predication to a user interface.

* * * * *